US012773449B2

(12) United States Patent
Rao et al.

(10) Patent No.: US 12,773,449 B2
(45) Date of Patent: Oct. 27, 2026

(54) BACTERIOPHAGE-BASED, NEEDLE AND ADJUVANT-FREE, MUCOSAL COVID-19 VACCINE

(71) Applicant: The Catholic University of America, Washington, DC (US)

(72) Inventors: Venigalla B. Rao, Washington, DC (US); Jingen Zhu, Washington, DC (US)

(73) Assignee: The Catholic University of America, Washington, DC (US)

( * ) Notice: Subject to any disclaimer, the term of this patent is extended or adjusted under 35 U.S.C. 154(b) by 753 days.

(21) Appl. No.: 18/138,183

(22) Filed: Apr. 24, 2023

(65) Prior Publication Data

US 2023/0355738 A1 Nov. 9, 2023

Related U.S. Application Data

(60) Provisional application No. 63/334,823, filed on Apr. 26, 2022.

(51) Int. Cl.

| | |
|---|---|
| ***A61K 39/00*** | (2006.01) |
| ***A61K 39/12*** | (2006.01) |
| ***A61K 39/385*** | (2006.01) |
| ***A61K 48/00*** | (2006.01) |
| ***A61P 37/04*** | (2006.01) |
| ***C12N 15/63*** | (2006.01) |

(52) U.S. Cl.

CPC .............. *A61K 39/12* (2013.01); *A61P 37/04* (2018.01); *A61K 2039/543* (2013.01); *A61K 2039/545* (2013.01); *A61K 2039/575* (2013.01)

(58) Field of Classification Search

CPC ...... C12N 2795/00; C12N 2770/20034; A61K 39/40; A61K 39/0258; A61K 39/12

See application file for complete search history.

(56) References Cited

U.S. PATENT DOCUMENTS

2019/0309312 A1 10/2019 Ylera

FOREIGN PATENT DOCUMENTS

WO 2021/252450 A1 12/2021
WO 2022/023850 A1 2/2022

OTHER PUBLICATIONS

Corbett, K. S., et al. SARS-CoV-2 mRNA vaccine design enabled by prototype pathogen preparedness. Nature 586, 567-571 (2020).
Bos, R., et al. Ad26 vector-based COVID-19 vaccine encoding a prefusion-stabilized SARS-CoV-2 Spike immunogen induces potent humoral and cellular immune responses. npj Vaccines 5, 91 (2020).
Kalnin, K. V., et al. Immunogenicity and efficacy of mRNA COVID-19 vaccine MRT5500 in preclinical animal models. npj Vaccines 6, 61 (2021).
Sadarangani, M., et al. Immunological mechanisms of vaccine-induced protection against COVID-19 in humans. Nature Reviews Immunology 21, 475-484 (2021).
DiPiazza, A. T., et al. COVID-19 vaccine mRNA-1273 elicits a protective immune profile in mice that is not associated with vaccine-enhanced disease upon SARS-CoV-2 challenge. Immunity 54, 1869-1882 (2021).
Grifoni, A., et al. Targets of T cell responses to SARS-CoV-2 coronavirus in humans with COVID-19 disease and unexposed individuals. Cell 181, 1489-1501 (2020).
Zheng, H-Y., et al. Elevated exhaustion levels and reduced functional diversity of T cells in peripheral blood may predict severe progression in COVID-19 patients. Cellular & molecular immunology 17, 541-543 (2020).
Zheng, H-Yi., et al. Longitudinal transcriptome analyses show robust T cell immunity during recovery from COVID-19. Signal transduction and targeted therapy 5, 294 (2020).
Chen, G., et al. Clinical and immunological features of severe and moderate coronavirus disease 2019. The Journal of clinical investigation 130, 2620-2629 (2020).
Xiong, Y., et al. Transcriptomic characteristics of bronchoalveolar lavage fluid and peripheral blood mononuclear cells in COVID-19 patients. Emerging microbes & infections 9, 761-770 (2020).
Braun, J., et al. SARS-CoV-2-reactive T cells in healthy donors and patients with COVID-19. Nature 587, 270-274 (2020).
Chandrashekar, A., et al. SARS-CoV-2 infection protects against rechallenge in rhesus macaques. Science 369, 812-817 (2020).
Lambert, P-H., et al. Consensus summary report for CEPI/BC Mar. 12-13, 2020 meeting: assessment of risk of disease enhancement with COVID-19 vaccines. Vaccine 38, 4783-4791 (2020).
Hotez, P. J., et al. The potential role of Th17 immune responses in coronavirus immunopathology and vaccine-induced immune enhancement. Microbes and infection 22, 165-167 (2020).

(Continued)

*Primary Examiner* — Barry A Chestnut

(74) *Attorney, Agent, or Firm* — Ajay A. Jagtiani; Miles & Stockbridge P.C.

(57) ABSTRACT

A bacteriophage T4-based, multivalent/multicomponent, needle and adjuvant-free, mucosal vaccine by engineering spike trimers on capsid exterior and nucleocapsid protein in the interior is disclosed herein. Intranasal administration of this T4-COVID vaccine induces higher virus neutralization antibody titers against multiple variants, balanced Th1/Th2 antibody and cytokine responses, stronger $CD4^+$ and $CD8^+$ T cell immunity, and higher secretory IgA titers in sera and bronchoalveolar lavage with no effect on the gut microbiota, compared to vaccination of mice intramuscularly. The vaccine is stable at ambient temperature, induce apparent sterilizing immunity, and provide complete protection against original SARS-COV-2 strain and its Delta variant with minimal lung histopathology. This mucosal vaccine is an excellent candidate for boosting immunity of immunized and/or as a second-generation vaccine for the unimmunized population. This needle-free platform could be used to develop effective vaccines against many other respiratory infectious pathogens including Flu and any future emerging epidemic and pandemic pathogens.

44 Claims, 16 Drawing Sheets
(16 of 16 Drawing Sheet(s) Filed in Color)

Specification includes a Sequence Listing.

(56) References Cited

OTHER PUBLICATIONS

Shibabaw, T. Inflammatory cytokine: IL-17A signaling pathway in patients present with COVID-19 and current treatment strategy. Journal of inflammation research 673-680 (2020).
Ma, W-T., et al. The protective and pathogenic roles of IL-17 in viral infections: friend or foe?. Open biology 9, 190109 (2019).
Tesmer, L. A., et al. Th17 cells in human disease. Immunological reviews 223, 87-113 (2008).
Anipindi, V. C., et al. IL-17 production by γδ+ T cells is critical for inducing Th17 responses in the female genital tract and regulated by estradiol and microbiota. ImmunoHorizons 3, 317-330 (2019).
Guo, X., et al. CD4+ and CD8+ T cell- and IL-17-mediated protection against Entamoeba histolytica induced by a recombinant vaccine. Vaccine 29, 772-777 (2011).
Khader, S. A., et al. IL-23 and IL-17 in the establishment of protective pulmonary CD4+ T cell responses after vaccination and during *Mycobacterium tuberculosis* challenge. Nature immunology 8, 369-377 (2007).
Counoupas, C., et al. Mucosal delivery of a multistage subunit vaccine promotes development of lung-resident memory T cells and affords interleukin-17-dependent protection against pulmonary tuberculosis. npj Vaccines 5, 105 (2020).
Priebe, G. P., et al. IL-17 is a critical component of vaccine-induced protection against lung infection by lipopolysaccharide-heterologous strains of Pseudomonas aeruginosa. The Journal of Immunology 181, 4965-4975 (2008).
Edgar, R. C. UPARSE: highly accurate OTU sequences from microbial amplicon reads. Nature methods 10, 996-998 (2013).
Caporaso, J. G., et al. QIIME allows analysis of high-throughput community sequencing data. Nature methods 7, 335-336 (2010).
Quast, C., et al. The SILVA ribosomal RNA gene database project: improved data processing and web-based tools. Nucleic acids research 41, D590-D596 (2012).
Jończyk, E., et al. The influence of external factors on bacteriophages. Folia microbiologica 56, 191-200 (2011).
Endl, E., et al. Analysis of cell cycle-related Ki-67 and p120 expression by flow cytometric BrdUrd-Hoechst/7AAD and immunolabeling technique. Cytometry: The Journal of the International Society for Analytical Cytology 29, 233-241 (1997).
Penit, C. In vivo thymocyte maturation. BUdR labeling of cycling thymocytes and phenotypic analysis of their progeny support the single lineage model. Journal of immunology (Baltimore, Md.: 1950) 137, 2115-2121 (1986).
Kilgore, P. B., et al. A new generation needle-and adjuvant-free trivalent plague vaccine utilizing adenovirus-5 nanoparticle platform. npj Vaccines 6, 21 (2021).
Kilgore, P. B., et al. Combinatorial Viral Vector-Based and Live Attenuated Vaccines without an Adjuvant to Generate Broader Immune Responses to Effectively Combat Pneumonic Plague. Mbio 12, e03223-21 (2021).
Tiner, B. L., et al. Immunisation of two rodent species with new live-attenuated mutants of Yersinia pestis CO92 induces protective long-term humoral- and cell-mediated immunity against pneumonic plague. npj Vaccines 1, 1-12 (2016).
Tao, P., et al. Engineering of Bacteriophage T4 Genome Using CRISPR-Cas9. ACS Synthetic Biology 6, 1952-1961 (2017).
Liu, Y., et al. Covalent modifications of bacteriophage genome confer a degree of resistance to bacterial CRISPR systems. Journal of Virology 94, e01630-20 (2020).
Alu et al., "Intranasal COVID-19 vaccines: From bench to bed", EBioMedicine, Epub, vol. 76, Article No. 103841; pp. 1-16 (2022).
Zhu et al. "A bacteriophage-based, highly efficacious, needle and adjuvant-free, mucosal COVID-19 vaccine", bioRxiv, preprint version, pp. 1-59 (2022).
Zhu et al., "A universal bacteriophage T4 nanoparticle platform to design multiplex SARS-CoV-2 vaccine candidates by CRISPR engineering", Science Advances, vol. 7, Article No. eabh 1547; pp. 1-18 (2021).
Search Report and Written Opinion received in PCT Application No. PCT/IB2023/054229 mailed Aug. 17, 2023.
Tregoning, J. S., et al. Progress of the COVID-19 vaccine effort: viruses, vaccines and variants versus efficacy, effectiveness and escape. Nature Reviews Immunology 21, 626-636 (2021).
Hassan, A. O., et al. A Single-Dose Intranasal ChAd Vaccine Protects Upper and Lower Respiratory Tracts against SARS-CoV-2. Cell 183, 169-184 (2020).
Callaway, E., et al. How to redesign COVID vaccines so they protect against variants. Nature 590, 15-16 (2021).
Mercado, N. B., et al. Single-shot Ad26 vaccine protects against SARS-CoV-2 in rhesus macaques. Nature 586, 583-588 (2020).
Tiboni, M., et al. Nasal vaccination against SARS-CoV-2: Synergistic or alternative to intramuscular vaccines? International journal of pharmaceutics 603, 120686 (2021).
Zhu, J., et al. A universal bacteriophage T4 nanoparticle platform to design multiplex SARS-CoV-2 vaccine candidates by CRISPR engineering. Science advances 7, eabh1547 (2021).
Keeble, A. H., et al. Approaching infinite affinity through engineering of peptide-protein interaction. Proceedings of the National Academy of Sciences of the United States of America 116, 26523-26533 (2019).
Tao, P., et al. Bacteriophage T4 nanoparticles for vaccine delivery against infectious diseases. Advanced drug delivery reviews 145, 57-72 (2018).
Yao, H., et al. Molecular Architecture of the SARS-CoV-2 Virus. Cell 183, 730-738 (2020).
Hou, Y. J., et al. SARS-CoV-2 Reverse Genetics Reveals a Variable Infection Gradient in the Respiratory Tract. Cell 182, 429-446 (2020).
Van Belleghem, J. D., et al. Interactions between Bacteriophage, Bacteria, and the Mammalian Immune System. Viruses 11, 10 (2019).
Barr, J. J., et al. Bacteriophage adhering to mucus provide a non-host-derived immunity. Proceedings of the National Academy of Sciences of the United States of America 110, 10771-10776 (2013).
Barr, J. J., et al. Subdiffusive motion of bacteriophage in mucosal surfaces increases the frequency of bacterial encounters. Proceedings of the National Academy of Sciences 112, 13675-13680 (2015).
Rubin, R., Trying to block SARS-CoV-2 transmission with intranasal vaccines. Jama 326, 1661-1663 (2021).
Focosi, D., et al. Mucosal vaccines, sterilizing immunity, and the future of sars-cov-2 virulence. Viruses 14, 187 (2022).
Ku, M. W., et al. Intranasal vaccination with a lentiviral vector protects against SARS-CoV-2 in preclinical animal models. Cell host & microbe 29, 236-249 (2021).
Afkhami, S., et al. Respiratory mucosal delivery of next-generation COVID-19 vaccine provides robust protection against both ancestral and variant strains of SARS-CoV-2. Cell 185, 896-915 (2022).
Sterlin, D., et al. IgA dominates the early neutralizing antibody response to SARS-CoV-2. Science translational medicine 13, eabd2223 (2021).
Mistry, P., et al. SARS-CoV-2 variants, vaccines, and host immunity. Frontiers in immunology 12, 5400 (2022).
Castro, F., et al. Interferon-gamma at the crossroads of tumor immune surveillance or evasion. Frontiers in immunology 9, 847 (2018).
Sette, A., et al. Adaptive immunity to SARS-CoV-2 and COVID-19. Cell 184, 861-880 (2021).
Krammer, F., SARS-CoV-2 vaccines in development. Nature 586, 516-527 (2020).
Macpherson, A. J., et al. The immune geography of IgA induction and function. Mucosal immunology 1, 11-22 (2008).
Su, F., et al. Induction of mucosal immunity through systemic immunization: Phantom or reality? Human vaccines & immunotherapeutics 12, 1070-1079 (2016).
Asahi-Ozaki, Y., et al. Secretory IgA antibodies provide cross-protection against infection with different strains of influenza B virus. Journal of medical virology 74, 328-335 (2004).
Renegar, K. B., et al. Role of IgA versus IgG in the Control of Influenza Viral Infection in the Murine Respiratory Tract. The Journal of Immunology 173, 1978-1986 (2004).

(56) References Cited

OTHER PUBLICATIONS

Lapuente, D., et al. Protective mucosal immunity against SARS-CoV-2 after heterologous systemic prime-mucosal boost immunization. Nature communications 12, 1-14 (2021).
Ruck, C. E., et al. Vaccine interactions with the infant microbiome: Do they define health and disease? Frontiers in Pediatrics 8, 565368 (2020).
Chen, J., et al. The intestinal microbiota and improving the efficacy of COVID-19 vaccinations. Journal of Functional Foods 87, 104850 (2021).
Tegally, H., et al. Detection of a SARS-CoV-2 variant of concern in South Africa. Nature 592, 438-443 (2021).
Ahmad, L., Implication of SARS-CoV-2 immune escape spike variants on secondary and vaccine breakthrough infections. Frontiers in immunology 12, 4563 (2021).
Liu, Y., et al. The reproductive number of the Delta variant of SARS-CoV-2 is far higher compared to the ancestral SARS-CoV-2 virus. Journal of Travel Medicine 28, taab124 (2021).
King, R. G., et al. Single-dose intranasal administration of AdCOVID elicits systemic and mucosal immunity against SARS-CoV-2 and fully protects mice from lethal challenge. Vaccines 9, 881 (2021).
Van Doremalen, N., et al. Intranasal ChAdOx1 nCoV-19/AZD1222 vaccination reduces shedding of SARS-CoV-2 D614G in rhesus macaques. BioRxiv (2021).
An, D., et al. Protection of K18-hACE2 mice and ferrets against SARS-CoV-2 challenge by a single-dose mucosal immunization with a parainfluenza virus 5-based COVID-19 vaccine. Science Advances 7, eabi5246 (2021).
Park, J.-G., et al. Immunogenicity and protective efficacy of an intranasal live-attenuated vaccine against SARS-CoV-2. Science 24, 102941 (2021).
Sun, W., et al. A Newcastle disease virus expressing a stabilized spike protein of SARS-CoV-2 induces protective immune responses. Nature communications 12, 1-14 (2021).
Simpson, C. R., et al. First-dose ChAdOx1 and BNT162b2 COVID-19 vaccines and thrombocytopenia, thromboembolic and hemorrhagic events in Scotland. Nature medicine 27, 1290-1297 (2021).
Van, H., et al. Bronchoalveolar lavage of murine lungs to analyze inflammatory cell infiltration. JoVE (Journal of Visualized Experiments) 123, e55398 (2017).
Salonen, A., et al. Comparative analysis of fecal DNA extraction methods with phylogenetic microarray: effective recovery of bacterial and archaeal DNA using mechanical cell lysis. Journal of microbiological methods 81, 127-134 (2010).
Yu, Z., et al. Improved extraction of PCR-quality community DNA from digesta and fecal samples. Biotechniques 36, 808-812 (2004).
Hildebrand, F., et al. LotuS: an efficient and user-friendly OTU processing pipeline. Microbiome 2, 1-7 (2014).
Sallusto, F. Heterogeneity of human CD4+ T cells against microbes. Annual review of immunology 34, 317-334 (2016).
Rauch, S., et al. mRNA vaccine CVnCoV protects non-human primates from SARS-CoV-2 challenge infection. Biorxiv Dec. 2020 (2020).
Lipsitch, M., et al. Cross-reactive memory T cells and herd immunity to SARS-CoV-2. Nature Reviews Immunology 20, 709-713 (2020).
Sahin, U., et al. COVID-19 vaccine BNT162b1 elicits human antibody and TH1 T cell responses. Nature 586, 594-599 (2020).
Vogel, A. B., et al. A prefusion SARS-CoV-2 spike RNA vaccine is highly immunogenic and prevents lung infection in non-human primates. BioRxiv Sep. 2020 (2020).
Vogel, A. B., et al. BNT162b vaccines are immunogenic and protect non-human primates against SARS-CoV-2. bioRxiv Dec. 2020 (2020).

BACTERIOPHAGE-BASED, NEEDLE AND ADJUVANT-FREE, MUCOSAL COVID-19 VACCINE

CROSS-REFERENCE TO RELATED APPLICATIONS

This application claims benefit of priority of U.S. Provisional Patent Application No. 63/334,823 entitled, "A BACTERIOPHAGE-BASED, HIGHLY EFFICACIOUS, NEEDLE AND ADJUVANT-FREE, MUCOSAL COVID-19 VACCINE," filed Apr. 26, 2022. The entire contents and disclosures of these patent applications are incorporated herein by reference in their entirety.

This application makes reference to U.S. patent application Ser. No. 17/548,629, entitled "UNIVERSAL BACTERIOPHAGE T4 NANOPARTICLE PLATFORM TO DESIGN MULTIPLEX SARS-COV-2 VACCINE CANDIDATES BY CRISPR ENGINEERING," filed Dec. 13, 2021, which in turn claims priority to U.S. Provisional Patent Application No. 63/126,047, entitled "UNIVERSAL BACTERIOPHAGE T4 NANOPARTICLE PLATFORM TO DESIGN MULTIPLEX SARS-COV-2 VACCINE CANDIDATES BY CRISPR ENGINEERING," filed Dec. 16, 2020. The entire contents and disclosures of these patent applications are incorporated herein by reference.

GOVERNMENT INTEREST STATEMENT

This invention was made with the United States government support under NIAID/NIH Grant Nos. 3R01AI095366-07S1 (subaward: 1100992-100) AI111538, and AI081726, awarded by the National Institutes of Health and NSF Grant No. MCB-0923873, awarded by the National Science Foundation. The government has certain rights in the invention.

SEQUENCE LISTING

The application contains a Sequence Listing which has been submitted electronically in XML format and is hereby incorporated by reference in its entirety. Said. XML copy, created on Apr. 14, 2023, is named "109007-24392US01 xml" and is 53,784 bytes in size. The sequence listing contained in this .XML file is part of the specification and is hereby incorporated by reference herein in its entirety.

BACKGROUND

Field of the Invention

The present disclosure relates to generally to a bacteriophage-based, needle and adjuvant-free, mucosal COVID-19 vaccine.

Background of the Invention

The mRNA-and adenovirus-based SARS-COV-2 vaccines are effective in preventing COVID-19. However, a need exists for no needle-free mucosal vaccines authorized for human administration.

SUMMARY

According to first broad aspect, the present disclosure provides a protein-basedprotein-based vaccine comprising: a bacteriophage, an antigen, and a nucleoprotein. The antigen is attached to an outer capsid protein of the bacteriophage. The nucleoprotein is packaged inner capsid protein of the bacteriophage. The protein-basedprotein-based vaccine is a mucosal vaccine. The protein-basedprotein-based vaccine is needle and adjuvant-free.

According to a second broad aspect, the present disclosure provides a bacteriophage-based vaccine comprising: a bacteriophage, a spike protein, and a nucleoprotein. The bacteriophage is decorated with the spike protein on the surface of capsid protein of the bacteriophage. The nucleoprotein is hard-wired by human engineering and packed inner capsid protein. The bacteriophage-based vaccine is a mucosal vaccine. The bacteriophage-based vaccine is needle and adjuvant-free.

According to a third broad aspect, the present disclosure provides a device for administering a protein-basedprotein-based vaccine comprising recombinant phage into an intranasal passageway of a subject. The device comprises a therapeutically effective amount of the protein-basedprotein-based vaccine. The protein-basedprotein-based vaccine at least stops or partially reverses an infection disease.

According to a fourth broad aspect, the present disclosure provides a method of administering a protein-basedprotein-based vaccine comprising administering a protein-basedprotein-based vaccine comprising recombinant phage via intranasal passageway of a subject. A device comprises a therapeutically effective amount of the protein-basedprotein-based vaccine. The protein-basedprotein-based vaccine at least stops or partially reverses an infection disease. The protein-basedprotein-based vaccine comprises a bacteriophage, an antigen, and a nucleoprotein. The antigen is attached to outer capsid protein of the bacteriophage. The nucleoprotein is packaged inner capsid protein of the bacteriophage. The protein-basedprotein-based vaccine is a mucosal vaccine. The protein-basedprotein-based vaccine is needle and adjuvant-free.

According to a fifth broad aspect, the present disclosure provides a method of manufacturing a bacteriophage-based vaccine comprises decorating a spike protein on a surface of a capsid protein of a bacteriophage and hard-wiring a nucleoprotein by human engineering and packing an inner capsid protein of the bacteriophage. The bacteriophage-based vaccine is a mucosal vaccine. The bacteriophage-based vaccine is needle and adjuvant-free.

According to a sixth broad aspect, the present disclosure provides a kit comprising a therapeutically effective amount of a protein-basedprotein-based vaccine. The protein-basedprotein-based vaccine comprising: a bacteriophage, an antigen, and a nucleoprotein. The antigen is attached to an outer capsid protein of the bacteriophage. The nucleoprotein is packaged inner capsid protein of the bacteriophage. The protein-basedprotein-based vaccine is a mucosal vaccine. The protein-basedprotein-based vaccine is needle and adjuvant-free and at least stops or partially reverses an infection disease.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Definitions

Figures 1A, 1B, 1C:
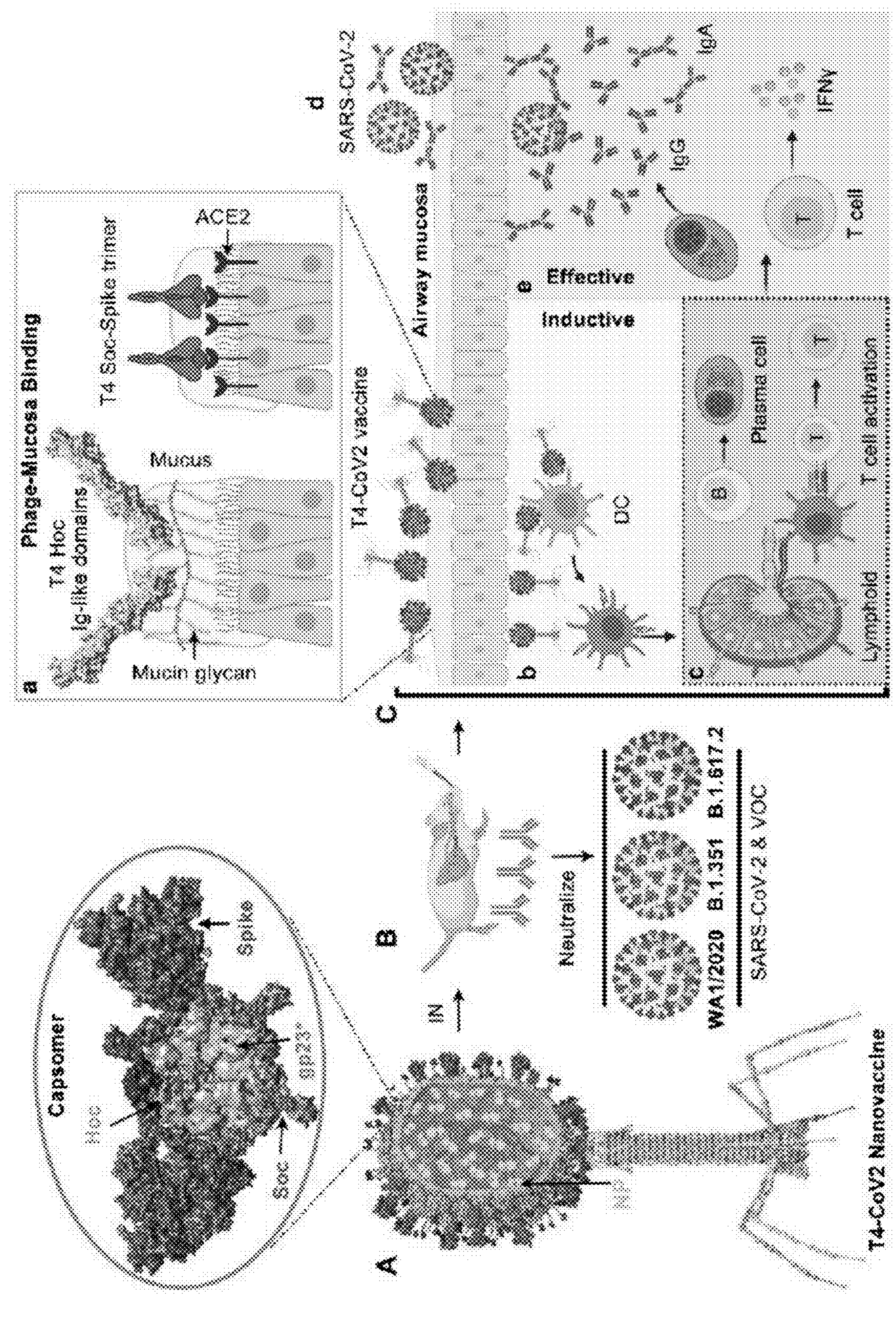
FIGS. 1A-1C illustrate T4-CoV-2 (also designated as T4-CoV2) intranasal (i.n. or also designated as IN) vaccination and mechanisms of protection according to one embodiment of the present disclosure.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY 4TH ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, the directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor. For purposes of the present disclosure, the phase "administration of a vaccine" refers to introduce a vaccine into a body of an animal or a human being. As is understood by an ordinary skilled person, it can be done in a variety of manners. For example, administration of a vaccine may be done intramuscularly, subcutaneously, intravenously, intranasally, intradermaly, intrabursally, in ovo, ocularly, orally, intra-tracheally or intra-bronchially, as well as combinations of such modalities. The dose of the vaccine may vary with the size of the intended vaccination subject.

For purposes of the present disclosure, the term "a value" or "property" is "based" on a particular value, property, the satisfaction of a condition, or other factor, if that value is derived by performing a mathematical calculation or logical decision using that value, property or other factor.

For purposes of the present disclosure, the term "adjuvant" refers to a composition comprised of one or more substances that enhances the immune response to an antigen (s). The mechanism of how an adjuvant operates is not entirely known. Some adjuvants are believed to enhance the immune response by slowly releasing the antigen, while other adjuvants are strongly immunogenic in their own right and are believed to function synergistically.

For purposes of the present disclosure, the term "ambient temperature" or "room temperature" refers to a temperature of from about 20° C. to about 25° C.

For purposes of the present disclosure, the term "amino acid" refers to the molecules composed of terminal amine and carboxylic acid functional groups with a carbon atom between the terminal amine and carboxylic acid functional groups sometimes containing a side chain functional group attached to the carbon atom (e.g. a methoxy functional group, which forms the amino acid serine). Typically, amino acids are classified as natural and non-natural. Examples of natural amino acids include glycine, alanine, valine, leucine, isoleucine, proline, phenylananine, tyrosine, tryptophan, serine, threonine, cysteine, methionine, asparagine, glutamine, lysine, arginine, histidine, aspartate, and glutamate, among others. Examples of non-natural amino acids include L-3, 4-dihydroxyphenylalanine, 2-aminobutyric acid, dehydralanine, g-carboxyglutamic acid, carnitine, gamma-aminobutyric acid, hydroxyproline, and selenomethionine, among others. In the context of this specification it should be appreciated that the amino acids may be the L-optical isomer or the D-optical isomer.

For purposes of the present disclosure, the term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten).

For purposes of the present disclosure, the term "array" refers to in vitro binding of a protein on a bacteria phage. For example, a Soc fusion protein, a protein fused with a small outer capsid protein Soc of a bacteriophage T4, may be arrayed by incubating Hoc-Soc-T4 phage particles with the Soc fusion protein to allow the Soc fusion protein to bind on Hoc-Soc-T4 phage particles.

For purposes of the present disclosure, the terms "bacteriophages" and "phages" are used interchangeably. These terms refer to a virus or a viral particle that can infect bacteria.

For purposes of the present disclosure, the term "bacteriophage-based vaccine" refers to a type of vaccine that utilizes bacteriophages as a delivery system for immunogenic components to induce an immune response in the host.

For purposes of the present disclosure, the term "bind", the term "binding", and the term "bound" refers to any type of chemical or physical binding, which includes but is not limited to covalent binding, hydrogen binding, electrostatic binding, biological tethers, transmembrane attachment, cell surface attachment and expression.

For purposes of the present disclosure, the term "biomolecule" refers to the conventional meaning of the term biomolecule, i.e., a molecule produced by or found in living cells, e.g., a protein, a carbohydrate, a lipid, a phospholipid, a nucleic acid, etc.

For purposes of the present disclosure, the term "capsid" and the term "capsid shell" refers to a protein shell of a virus comprising several structural subunits of proteins. The capsid encloses the nucleic acids of the virus. Capsids are broadly classified according to their structures. The majority of viruses have capsids with either helical or icosahedral structures.

For purposes of the present disclosure, the term "capsule" refers to a gelatinous envelope enclosing an active substance. Capsules may be soft-shelled capsules (softgels) or hard-shelled capsules. Capsules can be designed to remain intact for some hours after ingestion in order to delay absorption. They may also contain a mixture of slow- and fast-release particles to produce rapid and sustained absorption in the same dose.

For purposes of the present disclosure, the term "comprising", the term "having", the term "including," and variations of these words are intended to be open-ended and mean that there may be additional elements other than the listed elements.

For purposes of the present disclosure, the term "domain" and the term "protein domain" refer to a distinct functional or structural unit in a protein. Usually, a protein domain is responsible for a particular function or interaction, contributing to the overall role of a protein. Domains may exist in a variety of biological contexts, where similar domains can be found in proteins with different functions.

For purposes of the present disclosure, the term "dosage" refers to the administering of a specific amount, number, and frequency of doses over a specified period of time. Dosage implies duration. A "dosage regimen" is a treatment plan for administering a drug over a period of time.

For purposes of the present disclosure, the term "dosage form" and the term "unit dose" refer to an individual dose of a pharmaceutical product. Dosage forms may comprise a mixture of active drug components and nondrug components (excipients), along with other non-reusable material that may not be considered either ingredient or packaging.

For purposes of the present disclosure, the term “dose” refers to a specified amount of medication taken at one time.

For purposes of the present disclosure, the term “drug” refers to a material that may have a biological effect on a cell, including but not limited to small organic molecules, inorganic compounds, polymers such as nucleic acids, peptides, saccharides, or other biologic materials, nanoparticles, etc.

For purposes of the present disclosure, the term “effective amount” or “effective dose” or grammatical variations thereof refers to an amount of an agent sufficient to produce one or more desired effects. The effective amount may be determined by a person skilled in the art using the guidance provided herein.

For purposes of the present disclosure, the term “engineered” refers to being made by biological engineering.

For purposes of the present disclosure, the term “enhance” and the term “enhancing” refer to increasing or prolonging either in potency or duration of a desired effect. By way of example, “enhancing” the effect of therapeutic agents singly or in combination refers to the ability to increase or prolong, either in potency, duration and/or magnitude, the effect of the agents on the treatment of a disease, disorder or condition. When used in a patient, amounts effective for this use will depend on the severity and course of the disease, disorder or condition, previous therapy, the patient’s health status and response to the drugs, and the judgment of the treating physician.

For purposes of the present disclosure, the term “epitope” refers to a molecular region on the surface of an antigen capable of eliciting an immune response and combining with the specific antibody produced by such a response. It is also called “antigenic determinant.” T cell epitopes are presented on the surface of an antigen-presenting cell, where they are bound to MHC molecules.

For purposes of the present disclosure, the term “expression” and the term “gene expression” refer to a process by which information from a gene or a fragment of DNA is used in the synthesis of a functional gene product. A gene which encodes a protein will, when expressed, be transcribed and translated to produce that protein.

For purposes of the present disclosure, the term “fluid” refers to a liquid or a gas.

For purposes of the present disclosure, the term “fragment” of a molecule such as a protein or nucleic acid refers to a portion of the amino acid or nucleotide sequence.

For purposes of the present disclosure, the term “fuse” refers to join together physically, or to make things join together and become a single thing.

For purposes of the present disclosure, the term “fusion polypeptide” or the term “fusion protein” refers to a polypeptide or a protein created through the joining of two or more genes that originally coded for separate proteins. Translation of this fusion gene results in a single or multiple polypeptides with functional properties derived from each of the original proteins. Usually, a fusion protein has at least two heterologous polypeptides covalently linked, either directly or via an amino acid linker. The heterologous polypeptides forming a fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. These terms encompass conservatively modified variants, polymorphic variants, alleles, mutants, subsequences, interspecies homologs, and immunogenic fragments of the antigens that make up the fusion protein. In present disclosure, “fusion protein” and “recombinant protein” are interchangeable. Fusion proteins of the disclosure may also comprise additional copies of a component antigen or immunogenic fragment thereof. Recombinant fusion proteins are created artificially by recombinant DNA technology for use in biological research or therapeutics.

For purposes of the present disclosure, the term “gene” refers to a nucleic acid (e.g., DNA or RNA) sequence that comprises coding sequences necessary for the production of an RNA or a polypeptide or its precursor.

For purposes of the present disclosure, the term “i.n.” refers to intranasal.

For purposes of the present disclosure, the term “i.m.” refers to intramuscular.

For purposes of the present disclosure, the term “immune response” refers to a specific response elicited in an animal. An immune response may refer to cellular immunity (CMI); humoral immunity or may involve both. The present disclosure also contemplates a response limited to a part of the immune system. Usually, an “immunological response” includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

For purposes of the present disclosure, the term “immunity” refers to a state of resistance of a subject animal including a human to an infecting organism or substance. It will be understood that an infecting organism or substance is defined broadly and includes parasites, toxic substances, cancer cells and other cells as well as bacteria and viruses.

For purposes of the present disclosure, the term “immunization dose” refers to the amount of antigen or immunogen needed to precipitate an immune response. This amount will vary with the presence and effectiveness of various adjuvants. This amount will vary with the animal and the antigen, immunogen and/or adjuvant. The immunization dose is easily determined by methods well known to those skilled in the art, such as by conducting statistically valid host animal immunization and challenge studies.

For purposes of the present disclosure, the term “immunogen,” the term “immunogenic composition,” or the term “immunological composition” refers to a substance or material (including antigens) that is able to induce an immune response alone or in conjunction with an adjuvant. Both natural and synthetic substances may be immunogens.

For purposes of the present disclosure, the term “immunogenicity” refers to the ability to of a particular substance, such as an antigen or epitope, to provoke an immune response in the body of a human or animal. In other words, immunogenicity is the ability to induce a humoral and/or cell-mediated immune responses.

For purposes of the present disclosure, the term “individual” refers to an individual mammal, such as a human being.

For purposes of the present disclosure, the term “ligand” refers to a substance, such as a small molecule, that forms a complex with a biomolecule to serve a biological purpose. In protein-ligand binding, the ligand is usually a signaltriggering molecule, binding to a site on a target protein. Ligand binding to a receptor protein (receptor) alters the receptor's chemical conformation (three-dimensional shape). The conformational state of a receptor determines its functional state. Ligands include substrates, inhibitors, activators, and neurotransmitters.

For purposes of the present disclosure, the term "lipid" refers to hydrophobic or amphiphilic molecules, including but not limited to biologically derived lipids such as phospholipids, triacylglycerols, fatty acids, cholesterol, or synthetic lipids such as surfactants, organic solvents, oils, etc.

For purposes of the present disclosure, the term "multivalent" refers to a vaccine containing more than one antigen whether from the same species (i.e., different isolates of *Mycoplasma hyopneumoniae*), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

For purposes of the present disclosure, the term "mutation" refers to a change in the polypeptide sequence of a protein or in the nucleic acid sequence.

For purposes of the present disclosure, the term "needle-free" refers to any method of vaccine or drug administration that does not involve the use of needles or injections. By way of example only, a needle-free may be, but is not limited to: intranasal, oral, sublingual, and buccal.

For purposes of the present disclosure, the term "nucleoprotein" refers to a structural protein that plays a crucial role in the virus's life cycle. For example, the nucleoprotein binds to the viral RNA genome, forming a ribonucleoprotein complex (RNP). This complex is critical for protecting the viral RNA, facilitating its replication, and assisting in the assembly of new viral particles within the host cell. By way of example only, the nucleoprotein is highly conserved among coronaviruses, making it a potential target for diagnostics, therapeutics, and vaccine development.

For purposes of the present disclosure, the term "nutraceutical" refers to compounds and compositions that are useful in both the nutritional and pharmaceutical field of application. Thus, nutraceutical compositions of the present disclosure may be used as supplement to food and beverages, and as pharmaceutical formulations for enteral or parenteral application which may be solid formulations such as capsules or tablets, or liquid formulations, such as solutions or suspensions.

For purposes of the present disclosure, the term "parenteral route" refers to the administration of a composition, such as a drug in a manner other than through the digestive tract. Parenteral routes include routes such as intravenous, intra-arterial, transdermal, intranasal, sub-lingual and intraosseous, etc. For example, intravenous is also known as I.V., which is giving directly into a vein with injection. As the drug directly goes into the systemic circulation, it reaches the site of action resulting in the onset the action.

For purposes of the present disclosure, the term "pharmaceutical composition" refers to a product comprising one or more active ingredients, and one or more other components such as carriers, stabilizers, diluents, dispersing agents, suspending agents, thickening agents, and/or excipients, etc. A pharmaceutical composition includes enough of the active object compound to produce the desired effect upon the progress or condition of diseases and facilitates the administration of the active ingredients to an organism. Multiple techniques of administering the active ingredients exist in the art including, but not limited to: topical, ophthalmic, intraocular, periocular, intravenous, oral, aerosol, parenteral, and administration. By "pharmaceutically acceptable," it is meant the carrier, diluent or excipient must be compatible with the other ingredients of the formulation and not deleterious to the recipient thereof, i.e., the subject.

For purposes of the present disclosure, the term "pharmaceutically acceptable" refers to a compound or drug approved or approvable by a regulatory agency of a federal or a state government, listed or listable in the U.S. Pharmacopeia or in other generally recognized pharmacopeia for use in mammals, including humans.

For purposes of the present disclosure, the term "pharmaceutically acceptable carrier" refers to a carrier that comprises pharmceutically acceptable materials. Pharmaceutically acceptable carriers include, but are not limited to saline solutions and buffered solutions. Pharmaceutically acceptable carriers are described for example in Gennaro, Alfonso, Ed., Remington's Pharmaceutical Sciences, 18th Edition 1990. Mack Publishing Co., Easton, Pa., a standard reference text in this field. Pharmaceutical carriers may be selected in accordance with the intended route of administration and the standard pharmaceutical practice.

For purposes of the present disclosure, the term "p.i." refers to post infection.

For purposes of the present disclosure, the term "protein" refers to a biomolecule that comprises amino acid residues joined together by peptide bonds.

For purposes of the present disclosure, the term "purified" refers to the component in a relatively pure state, e.g. at least about 90% pure, or at least about 95% pure, or at least about 98% pure.

For purposes of the present disclosure, the term "stimulate," the term "immuno-stimulate" refers to induce the activation or increase the activity of any components in an immune system. For example, T cell activation requires at least two signals to become fully activated. The first occurs after engagement of the T cell antigen-specific receptor (TCR) by the antigen-major histocompatibility complex (MHC), and the second by subsequent engagement of co-stimulatory molecules. Once stimulated, the T cells will recognize the antigen or vaccine used during stimulation or activation of the T cells.

For purposes of the present disclosure, the term "subject" and the term "patient" refers to an entity which is the object of treatment, observation, or experiment. By way of example only, a "subject" or "patient" may be, but is not limited to: a human, a mammal, a reptile, a bird, a fish, an amphibian, and an invertebrate.

For purposes of the present disclosure, the term "subunit" refers to a separate polypeptide chain that makes a certain protein which is made up of two or more polypeptide chains joined together. In a protein molecule composed of more than one subunit, each subunit can form a stable folded structure by itself. The amino acid sequences of subunits of a protein can be identical, similar, or completely different.

For purposes of the present disclosure, the term "T4 bacteriophage" refers to a species of bacteriophages that infects *Escherichia coli* bacteria.

For purposes of the present disclosure, the terms "T4-CoV-2", "T4 CoV-2 vaccine", and "T4-CoV-2 vaccination" are used interchangeably. These terms refer to an optimal COVID-19 vaccine candidate.

For purposes of the present disclosure, the term "tablet" refers to a pharmaceutical dosage form. A tablet comprises a mixture of active substances and excipients, usually in powder form, pressed or compacted from a powder into a solid dose. The excipients can include diluents, binders or granulating agents, glidants and lubricants to ensure efficient tableting; disintegrants to promote tablet break-up in the digestive tract; sweeteners or flavors to enhance taste; and pigments to make the tablets visually attractive. A polymer coating is often applied to make the tablet smoother and easier to swallow, to control the release rate of the active ingredient, to make it more resistant to the environment (extending its shelf life), or to enhance the tablet's appearance. The disintegration time can be modified for a rapid effect or for sustained release. For example, Some tablets are designed with an osmotically active core, surrounded by an impermeable membrane with a pore in it. This allows the drug to percolate out from the tablet at a constant rate as the tablet moves through the digestive tract. Tablets can also be coated with sugar, varnish, or wax to disguise the taste. A tablet may also have one or more layers. A tablet may be mini tablet, a meltable table, chewable tablet, an effervescent tablet or an orally disintegrating tablet.

For purposes of the present disclosure, the term "target" refers to a living organism or a biological molecule to which some other entity, like a ligand or a drug, is directed and/or binds. For example, "target protein" may a biological molecule, such as a protein or protein complex, a receptor, or a portion of a biological molecule, etc., capable of being bound and regulated by a biologically active composition such as a pharmacologically active drug compound.

For purposes of the present disclosure, the term "therapeutically effective amount" and the term "treatment-effective amount" refers to the amount of a drug, compound or composition that, when administered to a subject for treating a disease or disorder, or at least one of the clinical symptoms of a disease or disorder, is sufficient to affect such treatment of the disease, disorder, or symptom. A "therapeutically effective amount" may vary depending, for example, on the compound, the disease, disorder, and/or symptoms of the disease or disorder, severity of the disease, disorder, and/or symptoms of the disease or disorder, the age, weight, and/or health of the subject to be treated, and the judgment of the prescribing physician. An appropriate amount in any given instance may be readily ascertained by those skilled in the art or capable of determination by routine experimentation.

For purposes of the present disclosure, the term "treating" or the term "treatment" of any disease or disorder refers to arresting or ameliorating a naturally occurring condition (for example, as a result of aging), disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to slowing the progression of a condition, inhibiting the disease or disorder, either physically, (e.g., stabilization of a discernible symptom), physiologically, (e.g., stabilization of a physical parameter), or both, and to inhibiting or slowing the progression of at least one physical parameter which may or may not be discernible to the subject. In some embodiments of the present disclosure, the terms "treating" and "treatment" refer to delaying the onset of the progression of the disease or disorder or at least one or more symptoms thereof in a subject who may be exposed to or predisposed to a disease or disorder even though that subject does not yet experience or display symptoms of the disease or disorder. The term "treatment" as used herein also refers to any treatment of a subject, such as a human condition or disease, and includes: (1) inhibiting the disease or condition, i.e., arresting the development or progression of the disease or condition, (2) relieving the disease or condition, i.e., causing the condition to regress, (3) stopping the symptoms of the disease, and/or (4) enhancing the conditions desired.

For purposes of the present disclosure, the term "vaccine" refers to a biological compound that improves immunity to a particular disease. A vaccine typically contains an agent that resembles a disease-causing microorganism (microbe), such as virus, bacteria, fungus, etc. Traditionally, it is often made from weakened or killed forms of the microbe, its toxins, or one of its surface proteins. The agent injected into a human or animal body stimulates the body's immune system to recognize the agent as foreign, destroy it, and keep a record of it, so that the immune system can more easily recognize and destroy any of these microorganisms that it later encounters.

For purposes of the present disclosure, the term "variant" refers to a subtype of a microorganism that is genetically distinct from a main strain, but not sufficiently different to be termed a distinct strain.

For purposes of the present disclosure, the term "vector", and "nanoparticle" are used interchangeably. These terms refer to a virus or viral particle that can be used to deliver genes or proteins.

For purposes of the present disclosure, the term "virus particle" refers to viruses and virus-like organisms.

For purposes of the present disclosure, the term "virus" refers to an infectious agent that is unable to grow or reproduce outside a host cell and that infects mammals (e.g., humans) or birds.

Description

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

The mRNA-and adenovirus-based vaccines currently used for human immunization are having a tremendous impact in tamping down the devastating COVID-19 pandemic that caused lockdown of the World and millions of deaths. Administered by intramuscular injections, these vaccines remain as the major source for the rest of the world's unvaccinated population, although other inactivated viral vaccines have also been authorized for human use. Many other vaccines are in various stages of preclinical studies and clinical trials (1). However, there are yet no needle-free mucosal vaccines authorized for human administration.

Needle-free intranasal vaccines that can elicit mucosal immunity are strategically important at this stage of the pandemic. Although the injectable vaccines are highly effective (70-95%) in preventing severe symptoms of the disease, hospitalizations of patients and deaths, they do not prevent viral acquisition or viral shedding from infected individuals. This is attributed to the lack of vaccine-induced secretory IgA (sIgA) mucosal immune responses in the respiratory airways that could prevent person to person transmission (3, 4). Therefore, risk of transmission from vaccinated subjects, who are susceptible to SARS-COV-2 infection, as seen currently on a global scale with the highly transmissible Omicron variant, remains a serious concern (5).

The mRNA-and adenovirus-based SARS-COV-2 vaccines effective in preventing COVID-19 require intramuscular injections, are targeted only to spike protein, and do not prevent viral transmission. Disclosed embodiments develop a bacteriophage T4-based, multivalent/multicomponent, needle and adjuvant-free, mucosal vaccine by engineering spike trimers on capsid exterior and nucleocapsid protein in the interior. Intranasal administration of T4-COVID vaccine induced higher virus neutralization antibody titers against multiple variants, balanced Th1/Th2 antibody and cytokine responses, stronger $CD4^+$ and $CD8^+$ T cell immunity, and higher secretory IgA titers in sera and bronchoalveolar lavage with no effect on the gut microbiota, compared to vaccination of mice intramuscularly. The disclosed vaccine is stable at ambient temperature, induce apparent sterilizing immunity, and provide complete protection against original SARS-COV-2 strain and its Delta variant with minimal lung histopathology. This mucosal vaccine is an excellent candidate for boosting immunity of immunized and/or as a second-generation vaccine for the unimmunized population.

The current vaccines developed using the spike protein encoding gene of the ancestral SARS-COV-2 strain (Wuhan-Hu-1) show progressively diminished efficacy against the subsequently emerged viral variants of concern (VOC) such as Alpha, Beta, Gamma, and Delta, and most recently Omicron and its subvariant BA.2. These variants have mutations in some of the neutralization epitopes and are more efficiently transmitted and/or more lethal. The evolutionary space for emergence of newer SARS-COV-2 variants/subvariants that are even more efficiently transmissible and also more lethal that might render the current vaccines ineffective remains a worrisome and real possibility. A vaccine platform that can incorporate additional conserved SARS-COV-2 components (such as nucleoprotein [NP] and RNA dependent RNA polymerase [RdRp]) and generate broader immune responses is therefore essential to develop more effective next-generation COVID-19 vaccines (2-3).

Considering the evolutionary path of the virus, the most desired next-generation vaccine(s) would be one that can induce strong mucosal immunity, in addition to broader systemic immunity. Additionally, platforms that are needle- and adjuvant-free and stable at ambient temperatures would greatly accelerate global distribution efforts, not only for controlling the current COVID-19 pandemic but also for any future epidemic or pandemic. Furthermore, needle-free vaccines can be administered easily and safely, and provide the best option to vaccinate children. No vaccine has yet been approved for children under 5-years, and the efficacy of the Pfizer BioNTech vaccine in the age group of 5-12 years is limited.

Disclosed embodiments recently reported (6) the development of a "universal" phage T4 vaccine design platform by Clustered Regularly Interspaced Short Palindromic Repeats (CRISPR) engineering that can rapidly generate multivalent and multicomponent vaccine candidates against any emerging or pandemic pathogen. By intramuscular injection, an optimal COVID-19 vaccine candidate (referred to as T4-CoV-2) elicited robust immunogenicity, virus neutralizing activity, and provided complete protection against ancestral SARS-COV-2 challenge in a mouse model. This is a multivalent/multicomponent vaccine consisting of a recombinant T4 phage decorated with ~100 copies of prefusion-stabilized spike ecto-domain trimers (S-trimers) on the surface of 120×86 nm virus capsid (FIG. 1A). The CHO EXPi-expressed S-trimers were covalently attached to the small outer capsid protein (Soc) of T4 through the SpyCatcher-SpyTag conjugation system (7). The vaccine also contained SARS-COV-2 NP packaged in the capsid core and a 12-amino acid (aa) peptide of the putative external domain of E protein (Ee) fused to the highly antigenic outer capsid protein (Hoc) displayed on the capsid surface. Both the NP and Ee were hard-wired into T4 genome by CRISPR engineering and incorporated into the phage nanoparticle structure during phage infection to make vaccine production easy and cost effective.

In one embodiment, a protein-basedprotein-based vaccine comprises a bacteriophage, an antigen, and a nucleoprotein. The antigen is attached to outer capsid protein of the bacteriophage. The nucleoprotein is packaged inner capsid protein of the bacteriophage.

The protein-basedprotein-based vaccine is a mucosal vaccine. The protein-basedprotein-based vaccine is needle and adjuvant-free.

In one embodiment, a bacteriophage is selected from the group consisting of Lambda phage, *Bacillus* phage Phi29, *Escherichia coli* phages T2, T3, T4, and T7, Enterobacteriaphage P22, and phage SPP1.

In one embodiment, a bacteriophage is *Escherichia coli* phage T4.

In one embodiment, an antigen is a prefusion-stabilized spike ecto-domain trimer.

In one embodiment, a bacteriophage-based vaccine comprises a bacteriophage, a spike protein, and a nucleoprotein. The bacteriophage is decorated with the spike protein on the surface of capsid protein of the bacteriophage. The nucleoprotein is hard-wired by human engineering, such as CRISPR, and packed inner capsid protein of the bacteriophage. The bacteriophage-based vaccine is a mucosal vaccine. The bacteriophage-based vaccine is needle and adjuvant-free.

In one embodiment, human engineering is CRISPR engineering.

In one embodiment, a bacteriophage-based vaccine further comprises a peptide of an E protein.

In one embodiment, a 12-amino acid peptide of a putative external domain of an E protein is fused to an outer capsid protein (Hoc) displayed on a capsid surface of the bacteriophage.

In one embodiment, a nucleoprotein, an E protein, and SpyCatcher genes are hard-wired by inserting respective expressible genes into a bacteriophage genome producing packaging nucleoprotein molecules inside the capsid, the peptide of the E protein at a tip of a Hoc fiber, and a SpyCatcher as a small outer capsid protein (Soc) fusion on the capsid surface.

In one embodiment, a Spytagged Spike Trimer purified from CHOExpi cells are conjugated to a Soc-SpyCatcher.

In one embodiment, the bacteriophage is T4 bacteriophage, and wherein the spike protein is a prefusion-stabilized spike ecto-domain trimer.

In one embodiment, spike proteins are covalently attached to a small outer capsid protein (Soc) of the bacteriophage through a SpyCatcher-SpyTag conjugation system.

In one embodiment, a device for administering a protein-basedprotein-based vaccine comprises recombinant phage into intranasal of an individual. The device comprises a therapeutically effective amount of the protein-basedprotein-based vaccine. The protein-basedprotein-based vaccine at least stops or partially reverses an infection disease.

In one embodiment, a protein-basedprotein-based vaccine is administered to a subject twice during a period of time and the subject may be selected from a human. In another embodiment, the subject may be selected from a group consisting of a mammal, a reptile, a bird, a fish, an amphibian, and an invertebrate.

In one embodiment, a protein-based vaccine is administered to a subject via an intranasal route and the subject may be selected from a human. In another embodiment, the subject may be selected from a group consisting of a mammal, a reptile, a bird, a fish, an amphibian, and an invertebrate.

In one embodiment, a protein-based vaccine is administered to a subject with a pharmaceutical carrier and wherein the subject may be selected from a human. In another embodiment, the subject may be selected from a group consisting of a mammal, a reptile, a bird, a fish, an amphibian, and an invertebrate.

In one embodiment, a protein-based vaccine is administered to a subject with a nutraceutical carrier and wherein the subject may be selected from a human. In another embodiment, the subject may be selected from a group consisting of a mammal, a reptile, a bird, a fish, an amphibian, and an invertebrate.

In one embodiment, a device may be selected from a group consisting of a container with a dropper/closure device, a squeeze bottle pump spray, and airless and preservative-free spray, and a nasal insert.

In one embodiment, a method of administering a protein-based vaccine comprises administering a protein-based vaccine comprising recombinant phage into intranasal of an individual by a device. The device may comprise a therapeutically effective amount of the protein-based vaccine. The protein-based vaccine at least stops or partially reverses an infection disease. The protein-based vaccine comprises a bacteriophage, an antigen, and a nucleoprotein. The antigen is attached to outer capsid protein of the bacteriophage. The nucleoprotein is packaged inner capsid protein of the bacteriophage. The protein-based vaccine is a mucosal vaccine. The protein-based vaccine is needle and adjuvant-free.

In one embodiment, a method of manufacturing a bacteriophage-based vaccine comprises decorating a spike protein on a surface of a capsid protein of a bacteriophage and hard-wiring a nucleoprotein by human engineering and packing an inner capsid protein of the bacteriophage. The bacteriophage-based vaccine is a mucosal vaccine. The bacteriophage-based vaccine is needle and adjuvant-free.

In one embodiment, a product made by a process comprises decorating a spike protein on a surface of a capsid protein of a bacteriophage and hard-wiring a nucleoprotein by human engineering and packing an inner capsid protein of the bacteriophage. The product is a mucosal vaccine. The product is needle and adjuvant-free.

In one embodiment, a method of treatment of a patient comprises administering a therapeutically effective amount of a protein-based vaccine to the patient suffering from an infection disease.

In one embodiment, a patient is selected from the group consisting of a human, a mammal, a reptile, a bird, a fish, an amphibian, and an invertebrate.

In one embodiment, a kit comprises a therapeutically effective amount of a protein-based vaccine. The protein-based vaccine at least stops or partially reverses an infection disease.

In one embodiment, a vaccine is delivered to a subject with at least one selected from the group consisting of a softgel, a hard capsule, a hard capsule with compounds coated differently, a tablet, a chewable tablet, and a caplet and wherein the subject is selected from the group consisting of a human, a mammal, a reptile, a bird, a fish, an amphibian, and an invertebrate.

The protective immunity of the T4-CoV-2 nanovaccine could potentially be because of the repetitive and symmetrical arrays of S-trimers on phage particles, resembling the PAMPs (pathogen-associated molecular patterns) present on human viral pathogens (8). This architecture, in some respects, might mimic the spikes displayed on the SARS-COV-2 virion (9). Therefore, we hypothesized that it is probable that such a T4-CoV-2 nanoparticle when exposed to nasal mucosal surfaces might be recognized as a natural viral intruder by the resident immune cells, stimulating strong mucosal as well as systemic immune responses (FIGS. 1B and 1C). Furthermore, the S-trimer-displayed T4-CoV-2 nanoparticle could efficiently bind to nasal epithelium that has the highest concentration of angiotensin-converting enzyme (ACE2) receptors (10). Additionally, the 155 symmetrically arranged Ig-like Hoc fibers on the T4 capsid are reported to interact with mucin glycoproteins, potentially capturing the T4-CoV-2 vaccine particles at the nasal mucosa (12, 13) (FIG. 1C, a). Such vaccine-induced mucosal responses by a virus nanoparticle vaccine are expected to be superior to the systemic immune responses generated by traditional injectable vaccines (2, 14-15). Elicitation of target-specific mucosal antibodies at the portal of entry would block virus acquisition as well as shedding of infectious virus particles and their potential transmission (16-18), which are essential attributes of a highly efficacious vaccine to end this prolonged pandemic.

In one embodiment, a bacteriophage-based vaccine has repetitive and symmetrical arrays of spike proteins on the surface of the bacteriophage, resembling pathogen-associated molecular patterns present on human viral pathogens.

Here, disclosed embodiments tested this hypothesis in a mouse model by intranasal (i.n.) inoculation of the T4-CoV-2 vaccine and compared the immune responses with those elicited by intramuscular (i. m.) injection. Remarkably, this needle- and adjuvant-free vaccination with non-infectious T4-COVID nanoparticles induced strong mucosal, humoral, and cellular immunity in BALB/c as well as human ACE2 (hACE2) transgenic mice. Importantly, these responses (after i.n. delivery) were much stronger when compared to the injected vaccine. For example, the needle-free vaccine induced stronger and broader virus neutralizing activity against both the ancestral SARS-COV-2 and two VOC (B.1.135 beta and B.1.617.2 delta), and robust T cell immunity consisting of spike/RBD (receptor-binding domain)-specific $CD4^+$ helper and effector T cells and $CD8^+$ killer T cells. Most importantly, strong mucosal secretory spike-specific IgA antibodies, and broad virus (including Omicron) neutralizing activity in the respiratory tract (FIGS. 1B and 1C) were measured in the bronchoalveolar lavage fluid (BALF) of only i.n. vaccinated mice.

The strong mucosal immunity stimulated by the needle-free, adjuvant-free, and multi-component/multivalent nanoparticle T4-CoV-2 vaccine might serve as an effective booster vaccine or as a next-generation broadly protective vaccine for the unvaccinated populations. This is particularly relevant now since there are compelling reasons for a strategic shift in COVID vaccine design from generating variant-specific injectable vaccines to intranasal vaccines that can block transmission of emerging variants. Also, inclusion of other virus components such as NP and further broadening of humoral, cellular, and mucosal immunity might provide added advantages as a "universal" corona vaccine to block the spread of future variants, or even when the COVID-19 pandemic acquires the status of an epidemic or an endemic disease. Furthermore, the T4-CoV-2 vaccine which is stable at ambient temperature can be easily manufactured and distributed at a modest cost; hence it might accelerate the current efforts to curtail further spread of this pandemic still ravaging across the globe and to potentially end it.

Figures 2A, 2U:
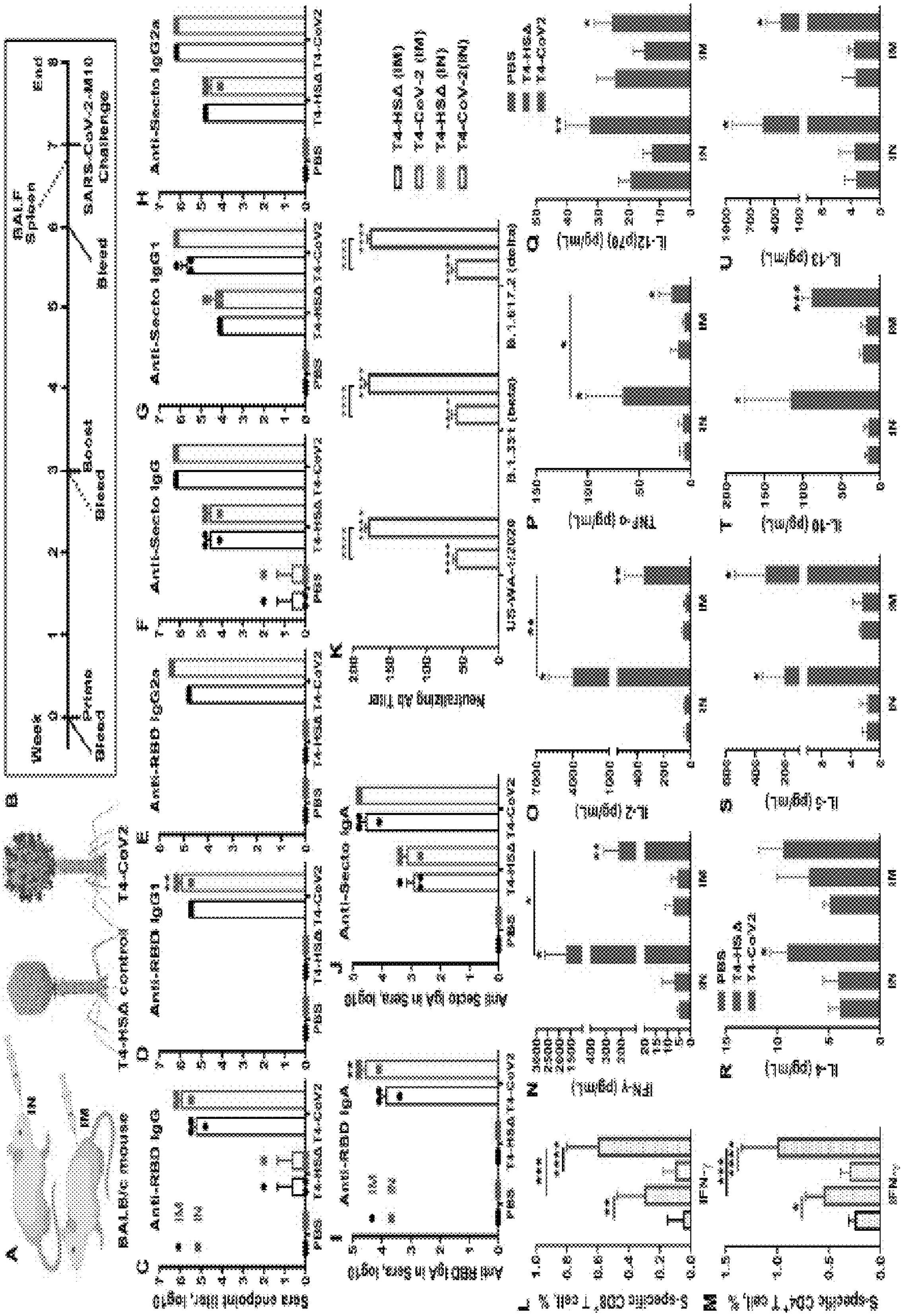
FIGS. 2A-2U illustrate intranasal (IN) immunization elicits its superior anti-spike/RBD systemic humoral and cellular responses over intramuscular (IM) immunization according to one embodiment of the present disclosure.
Figures 3A, 3B, 3C, 3D, 3E, 3F, 3G, 3H:
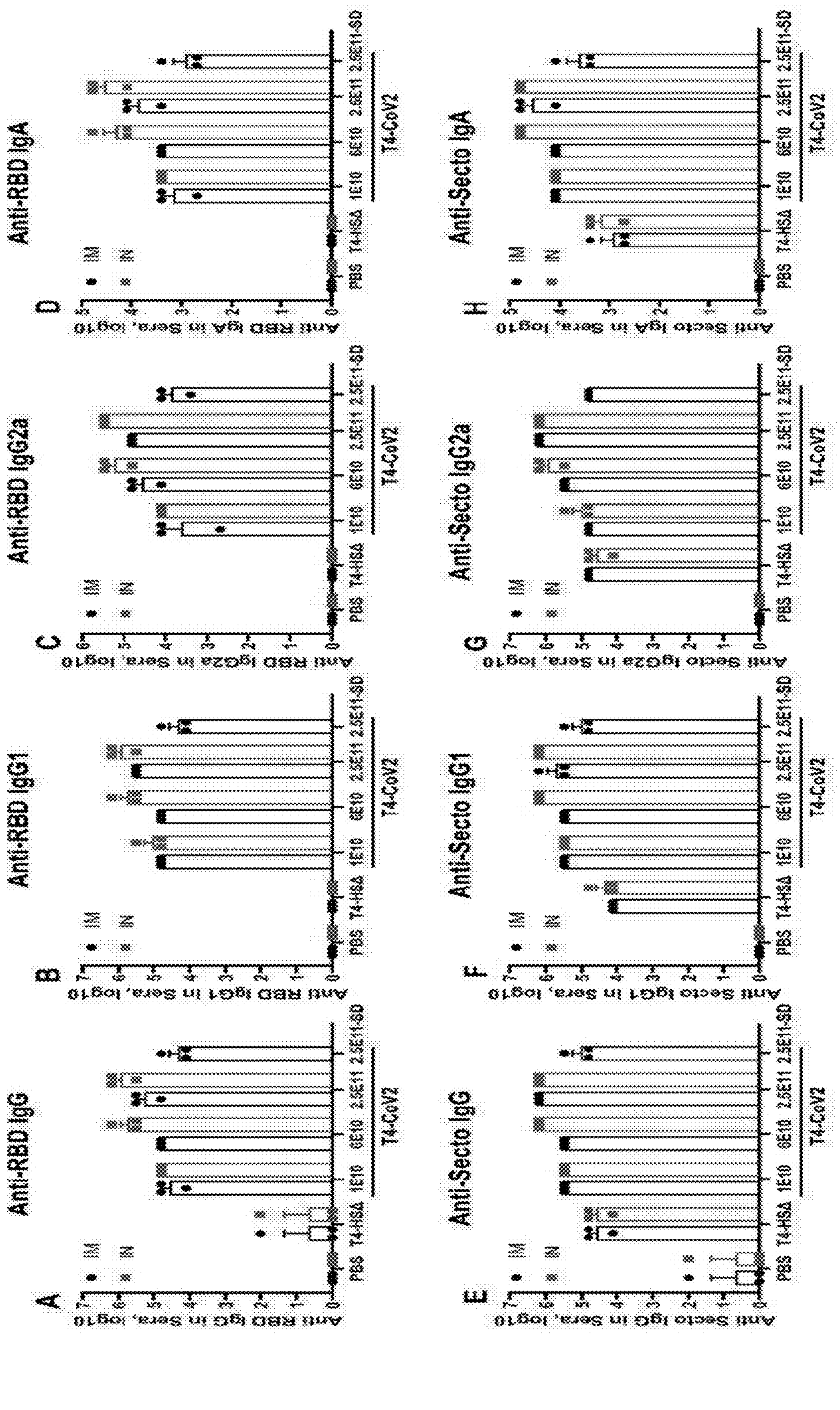
FIGS. 3A-3H illustrate anti-spike/RBD systemic humoral responses in IM and IN administrated mice using various doses of T4-CoV-2.

Needle-Free T4-CoV-2 Nanoparticle Vaccine Stimulates Stronger and More Robust Humoral and Cellular Immune Responses Against SARS-COV-2 and VOC than an Injectable Vaccine The immunogenicity of the T4-CoV-2 nanovaccine was first evaluated in 5-week-old conventional BALB/c mice. In a standard prime-boost regimen (FIGS. 2A and 2B), animals received two i.m. or i.n. doses of either the T4 phage backbone (vector control) or the T4-CoV-2 phage vaccine decorated with 20 μg (high-dose; ~$2.5\times10^{11}$ particles), 4.8 μg (medium-dose, ~$6\times10^{10}$ particles), or 0.8 μg (low-dose; ~$1\times10^{10}$ particles) of S-trimers. In a 1-dose regimen, animals received a single i.m. high dose of the T4-CoV-2 vaccine.

Antibody responses (IgG, isotypes, and IgA): To evaluate humoral antibody responses, sera were collected on day 21 for 1-dose regimen or day 42 for 2-dose regimen, 21-days after the last dose (FIG. 2B), and IgG, IgG1, and IgG2a antibodies specific to SARS-COV-2 ecto-S protein or the RBD domain were quantified by ELISA (FIGS. 2C-2H and FIGS. 3A-3H). The phosphate-buffered saline (PBS) and T4-vetor control groups, as expected, induced no significant antigen-specific antibodies, whereas the T4-CoV-2 vaccinated groups (either i.m. or i.n.) triggered high levels of IgG antibodies (FIGS. 2C and 2F). The end point titers for anti-RBD antibodies were as high as 62,500 and 312,500 for injected (i.m.) and needle-free (i.n.) vaccinated groups of mice, respectively.

High levels of both Th1 (IgG2a) and Th2 (IgG1) subtype antibodies were induced by i.m. and i.n. immunizations, demonstrating that the T4-CoV-2 vaccine triggered balanced Th1-and Th2-derived antibody responses, regardless of the route of administration (FIGS. 2D, 2E, 2G, and 2H). This is in contrast to the alum-adjuvanted subunit vaccines that show strong Th2-bias (6). The balanced immune response was also uniformly recapitulated in a dose response experiment. Nearly the same levels of Th1 and Th2 antibody responses were elicited with the medium-dose as with the high-dose, while the levels were lower (5-25-fold) with the low-dose or single-dose antigen (FIGS. 3A-3H).

Intriguingly, the T4-CoV-2 vaccine induced high levels of serum IgA antibodies when administered either by the i.m. or the i.n. route (FIGS. 2I and 2J). This is notable because IgA stimulation is not commonly observed in traditional vaccines including the current COVID-19 vaccines. Even the adenovirus-based vaccines do not elicit significant serum IgA titers (~100 background end-point titer) when injected by the i.m. route (2). Elicitation of serum IgA is considered desirable for an effective COVID-19 vaccine because IgA antibodies are reported to have anti-inflammatory activity and are more potent than IgG in neutralizing SARS-CoV-2 virus during the early phase of infection (18).

Figures 4A, 4N:
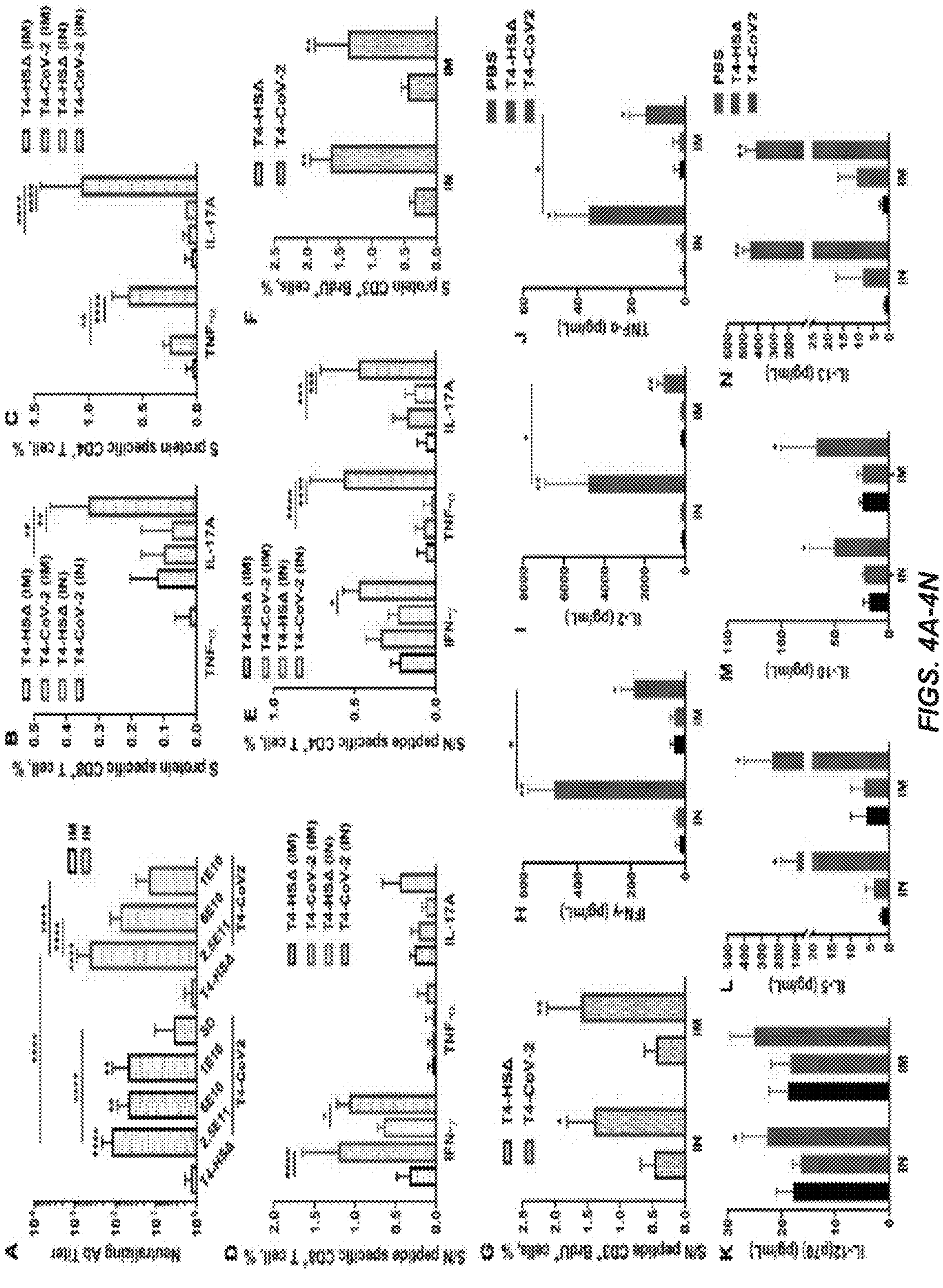
FIGS. 4A-4N illustrate neutralizing antibody and cellular immune responses in IM and IN vaccinated mice.

Virus neutralizing antibodies: To further analyze humoral immunity, the virus neutralizing activity of the elicited antibodies was determined by Vero E6 cell cytopathic assay using ancestral SARS-COV-2 US-WA-1/2020 strain, the first patient isolate obtained through the Centers for Disease Control and Prevention (CDC). As shown in FIG. 4A, the T4-CoV-2 vaccine induced strong virus neutralizing activity in complement-inactivated sera of all immunized mice. In addition, a dose dependent virus neutralizing activity was observed in the T4-CoV-2 i.n. immunized animals, while this phenomenon was not apparent in animals i.m. immunized with the T4-CoV-2 vaccine. Significantly higher virus neutralizing antibody titers were detected in mice immunized i.m. with 2 doses of the T4-CoV-2 vaccine than with a single dose immunization (FIG. 4A). Importantly, a higher virus neutralizing antibody titer (3-fold) was induced by i.n. vaccination when compared to i.m. route of high-dose immunization (FIG. 4A).

In one embodiment, a bacteriophage-based vaccine induces higher virus neutralization antibody titers against multiple variants than an intramuscular injection.

It is well known that Beta and Delta variants escape vaccine-induced immune responses (19). Intriguingly, the T4-CoV-2 vaccine elicited comparable virus neutralizing activities to ancestral SARS-COV-2 US-WA-1/2020 strain, Beta (B.1.351), and Delta (B.1.617.2) VOC (FIG. 2K). Additionally, ~2.5-fold higher virus neutralizing antibody titer against SARS-COV-2 and its VOC was elicited by i.n. vaccination when compared to i.m. route of immunization, while no detectable virus neutralizing activities were detected in T4 vector control groups (FIG. 2K).

Cell-mediated immunity: To evaluate cellular immune responses, splenocytes were harvested from mice on day 26 after the boost (FIG. 2B). Antigen-specific $CD4^+$ and $CD8^+$ T cells were identified by ex vivo restimulation with either S-trimer (FIGS. 2L and 2M; FIGS. 4B and 4C) or with SARS-COV-2 peptides spanning the S and NP proteins (FIGS. 4D and 4E). The samples were then analyzed by intracellular staining of accumulated cytokines and flow cytometry. The percentages of CD4 and CD8 T cells positive for tumor necrosis factor (TNF)-α, interferon (IFN)-γ, or interleukin 17A (IL-17A) were elevated in T4-CoV-2 immunized mice as compared to the T4 vector control group irrespective of the immunization routes and the virus-specific stimulants used (FIGS. 2L, 2M, and 4B-4E).

IFNγ is a predominant cytokine secreted by effector $CD8^+$ T cells, Th1 $CD4^+$ T cells, and NK cells (20). More specifically, with re-stimulation of splenocytes using S protein, significant levels of $IFN\gamma^+$ $CD8^+$ cells, which play a critical role in SARS-COV-2 viral clearance, were observed in i.n.-immunized mice (FIG. 2L). Additionally, significantly elevated percentages of $CD4^+$ T cells producing IFNγ and TNFα were detected in the i.n. group in comparison to the i.m. group of vaccinated mice (FIG. 2M). These data indicated an enhanced Th1-mediated immunity induced by i.n. administration of the vaccine. Of note, we did not observe significant differences between i.n. and i.m. routes of immunization regarding either the $IFN\gamma^+$ $CD8^+$ cells or the $IFN\gamma^+$ $CD4^+$ cells when restimulated with S and NP peptides (FIGS. 4D and 4E). Probably the conformational epitopes in S protein contributed to higher IFNγ levels in the i.n. group of animals. The robust T cell cytokine responses paralleled greater T cell proliferation as measured by the incorporation of BrdU (bromodeoxyuridine, an analog of thymidine), into newly synthesized DNA in both i.n. and i.m. immunized groups of animals as compared to the T4 vector control group (FIGS. 4F and 4G).

Additionally, representative Th1 and Th2 cytokines in cell supernatants of the splenocytes were analyzed by Bio-Plex platform. As can be noted, both routes of immunization triggered increased production of Th1 cytokines (IFNγ, IL-2, TNFα, and IL12-p70) (FIGS. 2N-2Q and 4H-4K) and Th2 cytokines (IL-4, IL-5, IL-10, and IL-13) (FIGS. 2R-2U and 4L-4M) compared to controls when splenocytes were stimulated with S-trimer or S-and NP-peptides. Increases in Th1 and Th2 cytokine levels by T4-CoV-2 immunization were consistent with induction of balanced Th1 and Th2 cellular immune responses, as described above. Importantly, the levels of the main Th1 cytokines, including IFNγ, IL-2, and TNFα, were significantly higher in animals immunized by the i.n. route than those in mice immunized by the i.m. route (FIGS. 2N-2P and 4H-4J). These data indicated that T4-CoV-2 i.n. immunization most likely produced more Th1-biased immune responses. The vaccine-associated enhanced respiratory disease (VAERD) has not usually occurred when strong Th1 cell responses are induced. Therefore, and considering that COVID-19 vaccine designs developed to date have attempted to elicit either a Th1-biased or a Th1/Th2-balanced cell response (21, 22), the T4-CoV-2 vaccine generated the desirable responses.

Needle-Free T4-CoV-2 Vaccination Elicits Robust Mucosal Immune Responses

It is generally recognized that intranasal vaccination leads to higher levels of sIgA antibodies at the mucosal surface with lower systemic IgG antibodies and cellular immune responses, while the opposite is true for intramuscular vaccination (5, 23-25). Remarkably however, intranasal T4-CoV-2 vaccination induced higher systemic as well as mucosal immune responses (FIGS. 2A-2U and 5A-5H). This appears to be a distinctive feature of the T4 nanoparticle vaccine.

Indeed, the needle-free T4-CoV-2 vaccine induced robust mucosal IgG and sIgA responses. These anti-RBD or anti-Spike antibody titers were determined in BALF samples of vaccinated mice, 26-days after the booster dose (FIGS. 5A-5H). Intranasally administered vaccine elicited ~25-fold higher IgG antibody levels in BALF compared to when animals were vaccinated by the i.m. route (FIGS. 5A and 5E), which also included both the Th1-biased IgG2a and Th2-biased IgG1 subtype antibodies in a balanced manner (FIGS. 5B, 5C, 5F, and 5G).

Figures 5A, 5B, 5C, 5D, 5E, 5F, 5G, 5H:
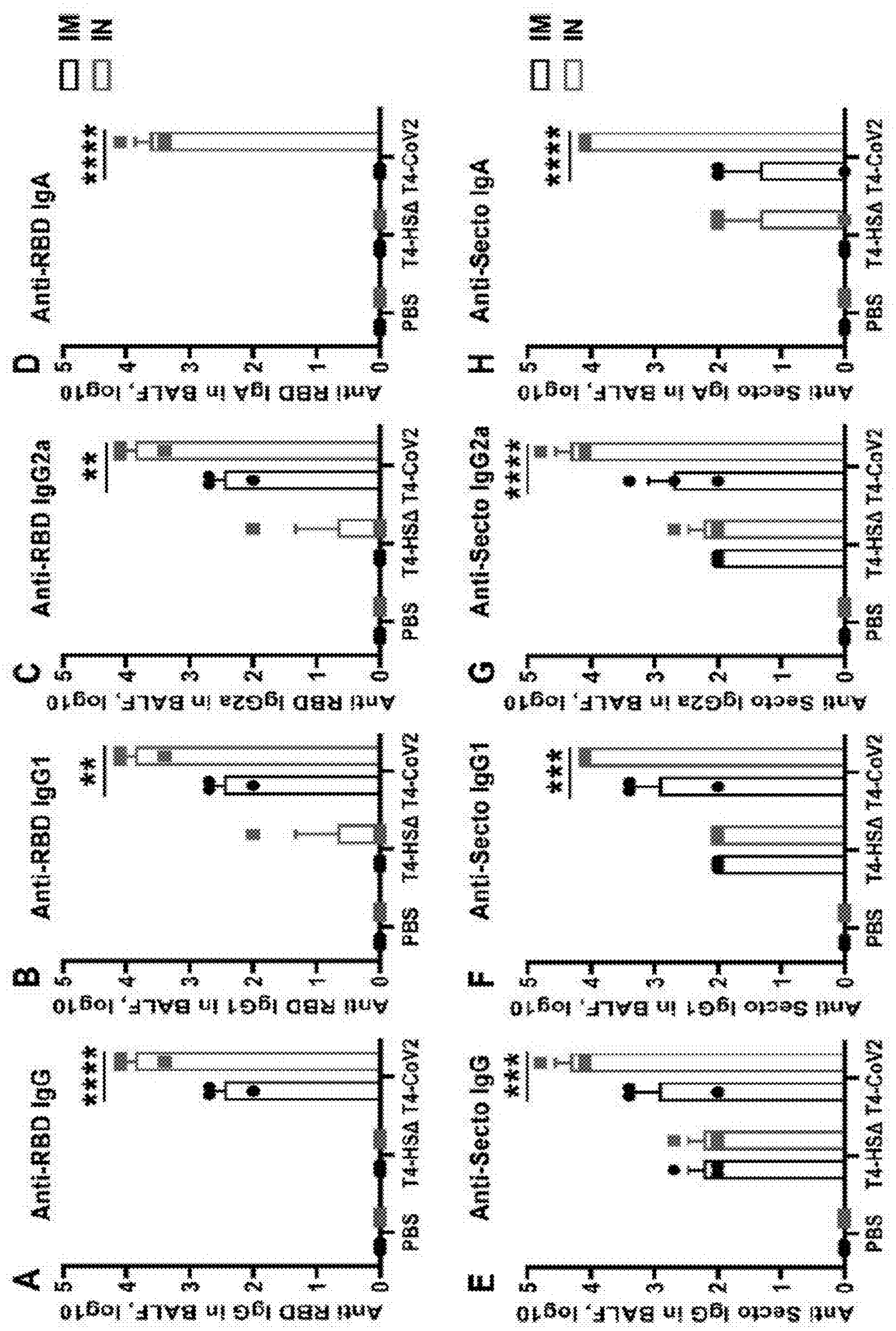
FIGS. 5A-5H illustrate T4-CoV-2 IN immunization induces robust mucosal immune responses compared to IM immunization according to one embodiment of the present disclosure.

The sIgA antibodies play a critical role in protecting mucosal surfaces against pathogens by blocking their attachment and/or entry of viruses transmitted through the respiratory tract. Thus, most significantly, high titers of mucosal sIgA antibodies were elicited by i.n. vaccination (FIGS. 5D and 5H), in addition to high levels of systemic immune responses as described above (FIGS. 2A-2U). In contrast, i.m. immunization failed to produce sIgA, which is not unexpected because i.m. vaccinations generally do not induce significant mucosal immune responses (FIGS. 5D and 5H). Since IgA antibodies are dimeric, they might have stronger SARS-COV-2 viral neutralization activity, and therefore, could confer protection at the site of exposure because mucosal surfaces of the respiratory tract, including the nasal regions and lung epithelial cells, which are the major targets for SARS-COV-2 infection (FIG. 1Ce) (26-28).

Figures 6A, 6B, 6C, 6D, 6E, 6F:
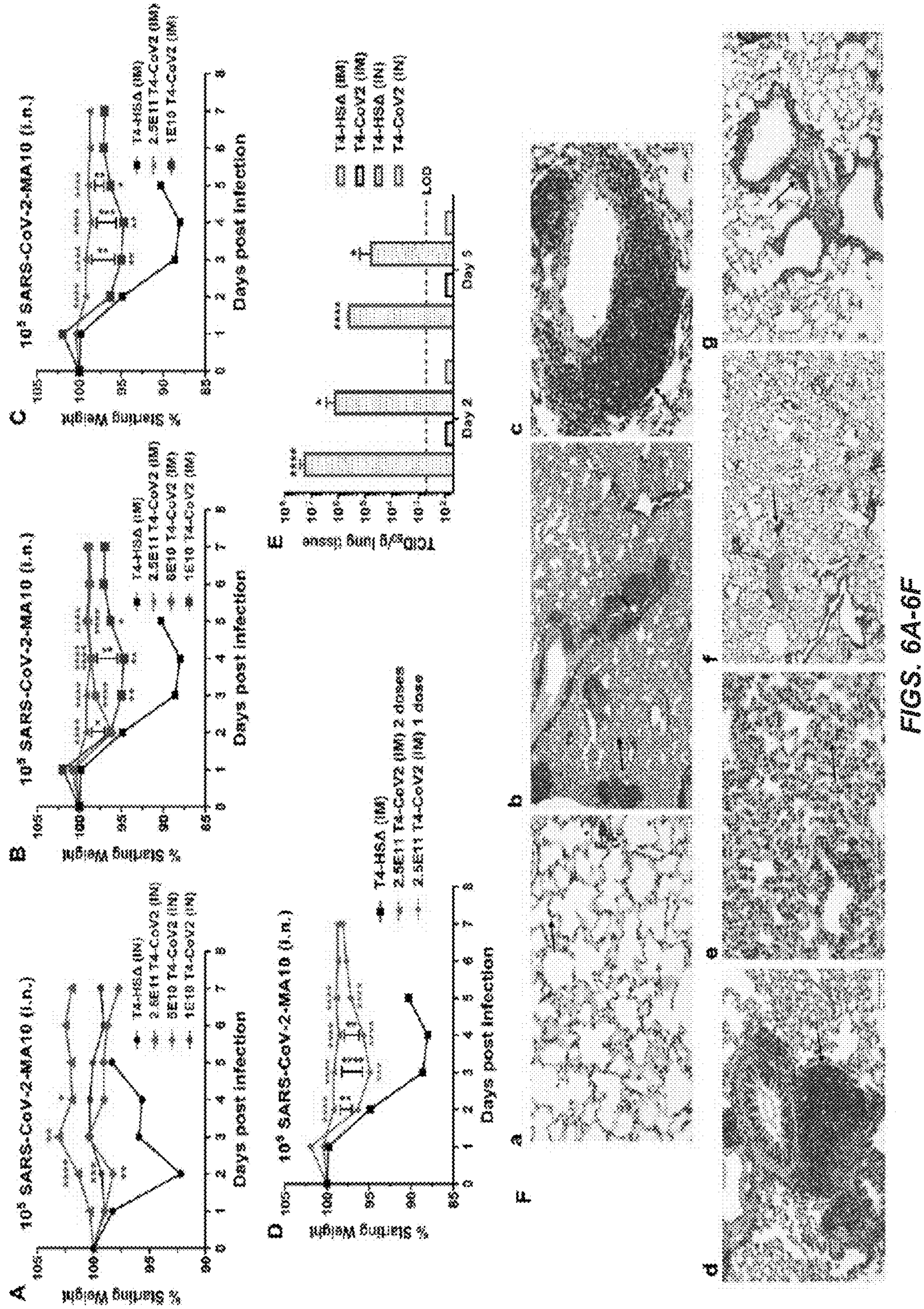
FIGS. 6A-6F illustrate needle-free T4-CoV-2 vaccine provides complete protection against SARS-COV-2 challenge according to one embodiment of the present disclosure.

Needle-Free T4-CoV-2 Vaccine Provides Complete Protection and Apparent Sterilizing Immunity Against SARS-COV-2 Challenge Animal challenge: BALB/c mice were challenged on day 28 after the last vaccine dose with the mouse adapted SARS-COV-2 strain (MA10) (FIG. 2B). As shown in FIGS. 6A-6D, the control animals that received the T4 vector exhibited a rapid weight loss soon after infection, with a maximum decrease on days 2-4 (FIGS. 6A and 6B). On the other hand, mice immunized with the T4-CoV-2 vaccine by either of the two immunization routes showed modest-to-no weight loss over the course of 7 days after challenge compared to their corresponding control groups irrespective of the number of T4-CoV-2 phage nanoparticles used for vaccination. However, the data was more impressive after i.n. immunization.

More specifically, a comparison when $1\times10^{10}$-$2.5\times10^{11}$ T4-COV-2 phage particles were used for i.n. vaccination, our data revealed that the weight loss curves among the highest ($2.5\times10^{11}$, 20 μg S-trimers), the medium ($6\times10^{10}$, 4.8 μg S-trimers), and the lowest ($1\times10^{10}$, 0.8 μg S-trimers) dose groups were almost similar statistically. Compared to the T4 vector control, a much-reduced loss in body weights were noted on day 2 post infection (p.i.) in all of the T4-CoV-2 vaccinated groups of mice with subsequent marginal, albeit minimal and statistically insignificant, fluctuations in body weight changes until day 7 (FIG. 6A).

In i.m.-immunized groups of mice with varying numbers of T4-CoV-2 phage particles, statistically significant less loss in body weights were observed from days 2-5 p.i. compared to the T4 vector control (FIG. 6B). Importantly, comparison of weight losses among animals vaccinated with the high vs medium vs low doses showed statistically significant differences on different days (FIG. 6B). Significantly less efficacy of the vaccine was apparent when the number of phage particles were reduced from $2.5\times10^{11}$ to $1\times10^{10}$ between days 3-5 (FIG. 6C). Similarly, significantly more weight loss was noticed in mice i.m. immunized with one dose of the T4-CoV-2 vaccine as compared to those receiving two doses on days 2-4 (FIG. 6D). These data were also consistent with the lower levels of immune responses elicited by i.m. vaccination when compared to i.n. vaccination.

Viral load: To further assess protective efficacy in the lungs, the infectious virus load was determined by plaque assay on days 2 and 5 p.i., the peak period of viral burden in this model. As shown in FIG. 6E, no infectious SARS-COV-2 virus could be detected in the lungs of mice immunized with the T4-CoV-2 vaccine ($2.5\times10^{10}$ phage particles) by either the i.m. or the i.n. route. Quite the opposite, very high levels of virus, ~$10^5$ to $10^7$ $TCID_{50}$/g (Tissue culture infectious disease [TCID]) of the tissue, were present on day 2 of the control mice, which decreased substantially on day 5 p.i., at which time the survived animals began to recover from infection.

Histopathology: The lung tissues obtained from the control and immunized mice (i.n. and i.m.) were subjected to H&E (hematoxylin and eosin) and MOVAT staining for histopathological analysis. The analysis was performed based on three parameters: mononuclear inflammatory infiltrate around bronchovascular bundles, interstitial inflammation, and alveolar exudate/hemorrhage (see materials and methods) and the data were statistically analyzed.

As shown in FIG. 6F, the uninfected normal lungs had delicate alveolar septa (black arrow, 40*x*) and distinct alveolar spaces (blue arrow) with no evidence of inflammation, hemorrhage, exudates, or transudates (FIG. 6Fa). On the other hand, prominent inflammatory infiltrates of bronchovascular bundles (red arrow) as well as interstitial involvement (black arrow) were noticed in the T4-vector control mice (i.n. immunized) during virus infection (FIG. 6Fb, 40*x*). More specifically, mononuclear inflammatory infiltrates were noticed around pulmonary vessel (black arrow, FIG. 6Fc, 200*x*) and around bronchovascular bundle (black arrow, FIG. 6Fd, 100*x*). Distal airways with interstitial inflammation in alveolar septa (black arrow, FIG. 6Fe) were evident. In addition, alveolar hemorrhage was also observed in other areas of the lungs.

As for the T4-COV-2 i.n. immunized mice, only mild and patchy inflammatory infiltrate of bronchovascular bundles (black arrow, FIGS. 6Ff and 6Fg, 40*x* and 100*x*, respectively) were noted after infection and the alveolar spaces and interstitium appeared normal (FIGS. 6Ff and 6Fg). Overall, the combined scores based on the above three parameters were 6.2=1.3 for the T4 vector control and 4.4=1.1 for the T4-CoV-2 vaccine i.n. immunized animals (p=0.01) when combined data on tissues after 2 and 5 days of challenge were analyzed.

The above data demonstrated that T4-CoV-2 vaccination by either route (i.m. and i.n.) completely protected mice against SARS-COV-2 challenge with no significant infectious virus detectable and marked attenuation of the inflammatory response in the lungs (based on histopathology of i.n.-immunized and infected mice). These data indicated that the T4-CoV-2 vaccine was more effective in clearing the pathogen when administered by the i.n. route and potentially could also block transmission of SARS-COV-2.

T4-CoV-2 Vaccine does not Influence the Microbiome Community in Mice

To determine if the T4-CoV-2 vaccine impacted microbiome community, DNA extracted from the fecal matter of individual mice (n=5/group) was sequenced for 16S rRNA gene on the Illumina MiSeq platform.

Figures 7A, 7B, 7C, 7D:
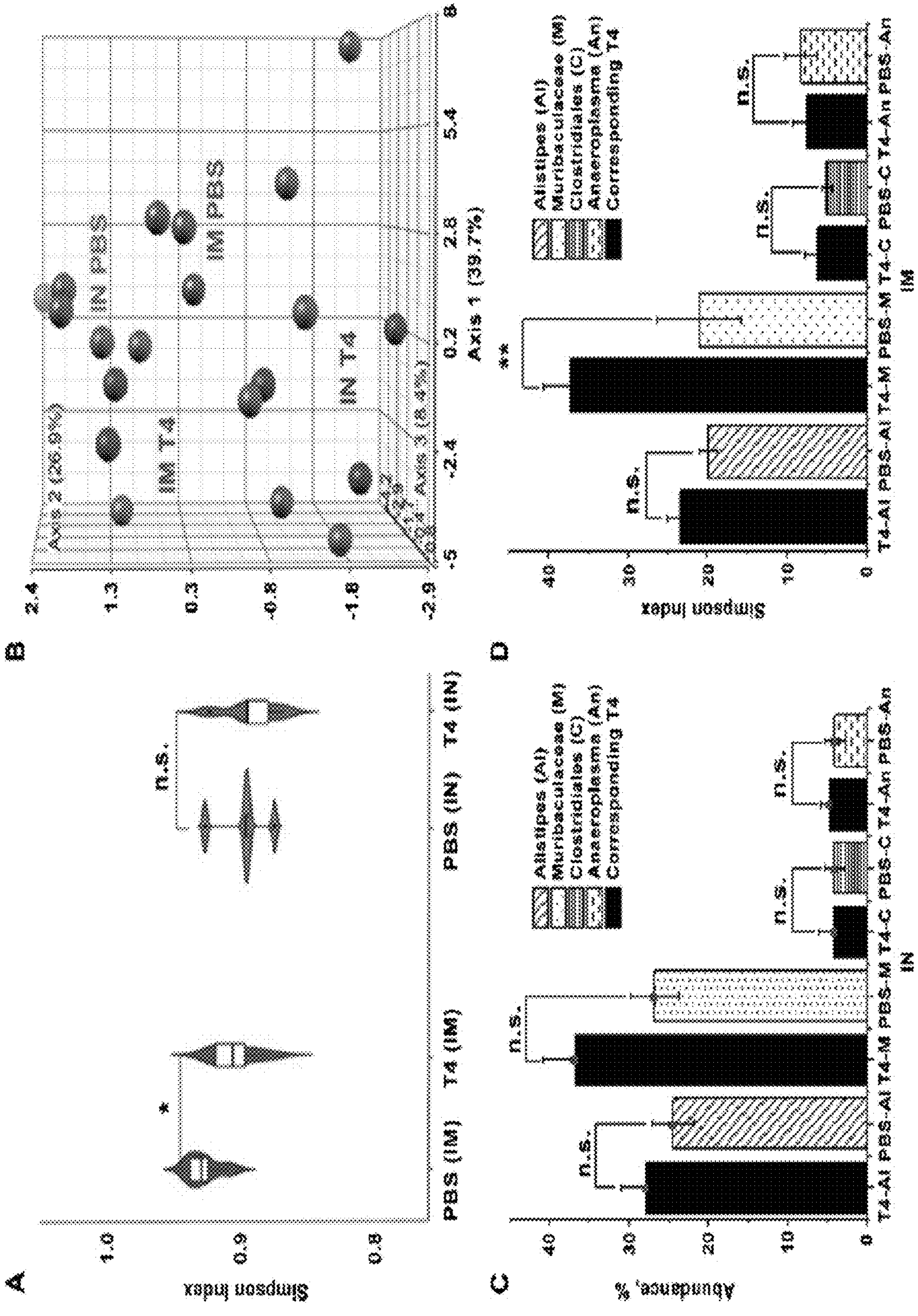
FIGS. 7A-7D illustrate T4-CoV-2 vaccine does not influence the microbiome community in mice, an effect which was more pronounced when vaccinated occurred by the IN over the IM route.

Violin plot: The violin plot in FIG. 7A showed the correlated distribution of the Simpson diversity index of microbiomes in the test groups. The measure of diversity included number and relative species abundance. As noted, the i.n. route of administration did not alter the Simpson diversity of the microbial species recovered from the PBS control versus the T4-CoV-2 vaccine groups of mice, unlike when i.m. route of vaccination was used. These results indicated that i.n. vaccination did not significantly affect the number and relative abundance of the gut microbiota.

Principal coordinate analysis (PCoA): FIG. 7B summarized individual Euclidian distance as a 3D resemblance matrix of microbial species from vaccinated and control groups when immunizations occurred by the i.n. or the i.m. route. The data indicated that the relative distances based on the number between species during both routes of immunization were similar, but there was a significant difference in species diversity when immunization occurred via the i.m. route (PBS control versus T4-CoV-2 groups). However, this was not the case during i.n. route for immunization as there was lack of significant differences among species.

Specific effect on the bacterial genera of the microbiome: FIGS. 7C and 7D showed abundance of the gut microbiota during i.n. and i.m. administration of the T4-CoV-2 vaccine and the PBS control. The Tukey mean comparison method between the test and control groups for the top four genera (Alistipes, Muribaculaceae, Clostridiales, and Anaeroplasma) indicated no significant differences in the gut microbiota even though there were few differences in numbers (e.g., for Alistipes and Muribaculaceae) when vaccine was administered by the i.n. route (FIG. 7C). However, a significant difference in the Muribaculaceae genus was noted when T4-CoV-2 vaccine was delivered by the i.m. route (FIG. 7D). These same differences were observed among the Bacteroidetes phylum indicating that i.m. administration of the T4-CoV-2 vaccine had a more significant impact on the gut microbiota. These trends were also reflective upstream of the hierarchy from families to the phylum of the recovered gut microbiota. Post-vaccination microbiota perturbation was previously reported by Ruck et al., 2020 during early microbial and immunological maturation stages in humans (29). Similarly, a systematic review by Chen et al., 2021 identified postvaccination dysbiosis as a significant problem in developing cellular immunity in COVID-19 vaccines, which can be corrected by introducing prebiotics and probiotics oral supplements after vaccination (30). However, notably, the T4-based COVID-19 vaccine administered by the i.n. route seemed to circumvent this effect on the microbiota.

Figures 8A, 8T:
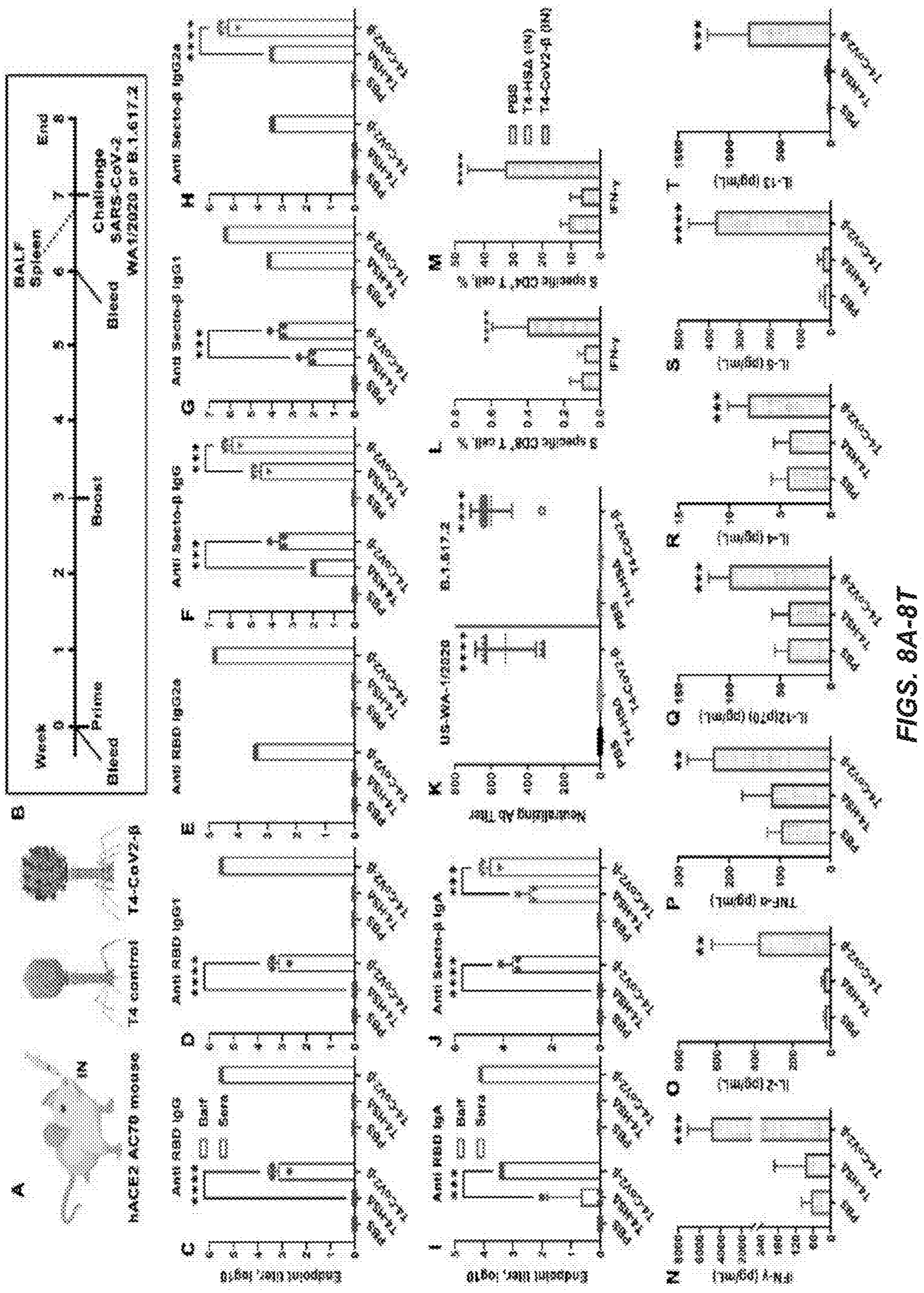
FIGS. 8A-8T illustrate T4-CoV-2 IN vaccination stimulates robust mucosal and systemic humoral and cellular immune responses in human ACE2 (hACE2) transgenic mice according to one embodiment of the present disclosure.
Figures 9A, 9B, 9C, 9D:
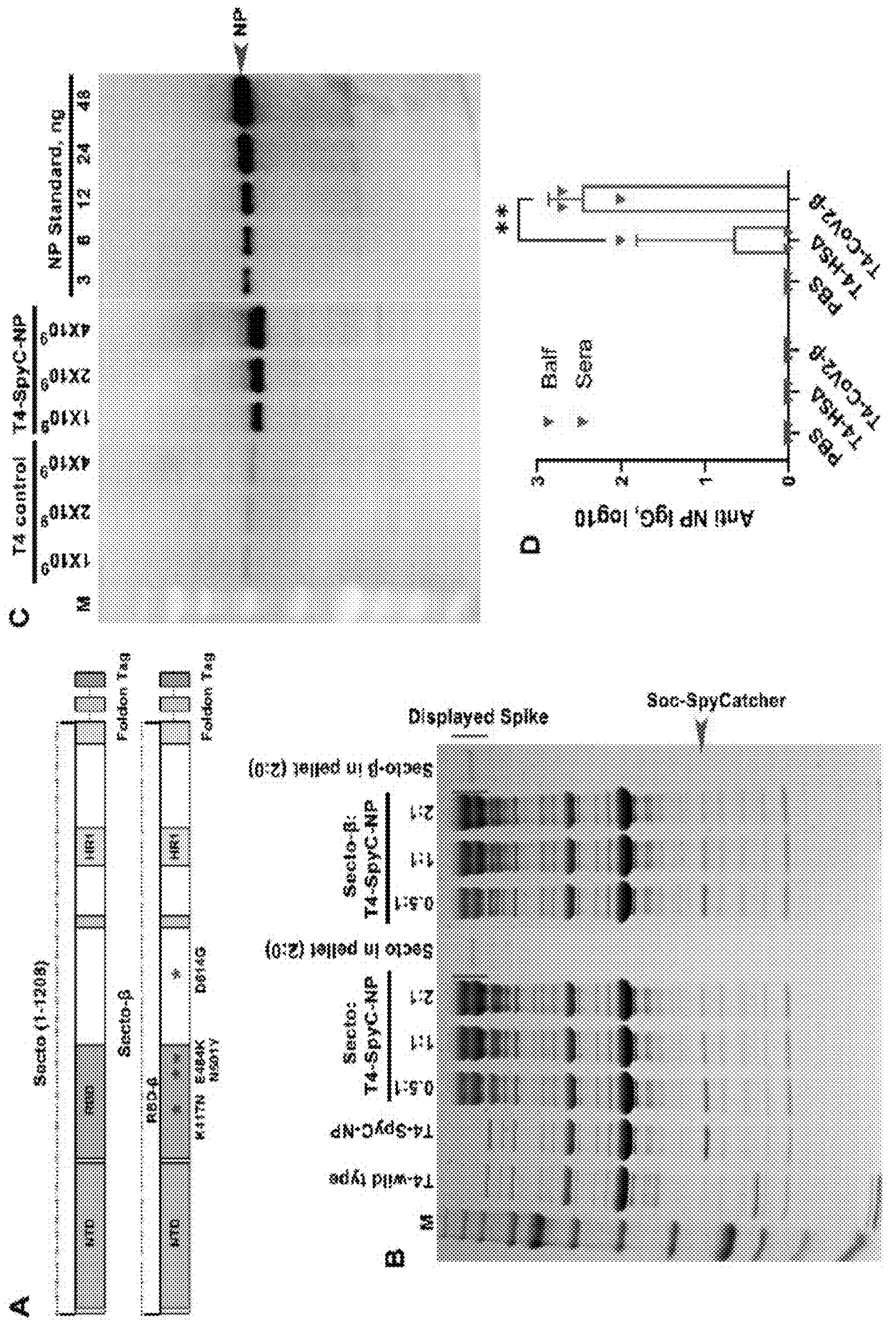
FIGS. 9A-9D illustrate Secto-β display on T4 and NP quantification.
Figures 10A, 10B, 10C, 10D, 10E, 10F, 10G, 10H:
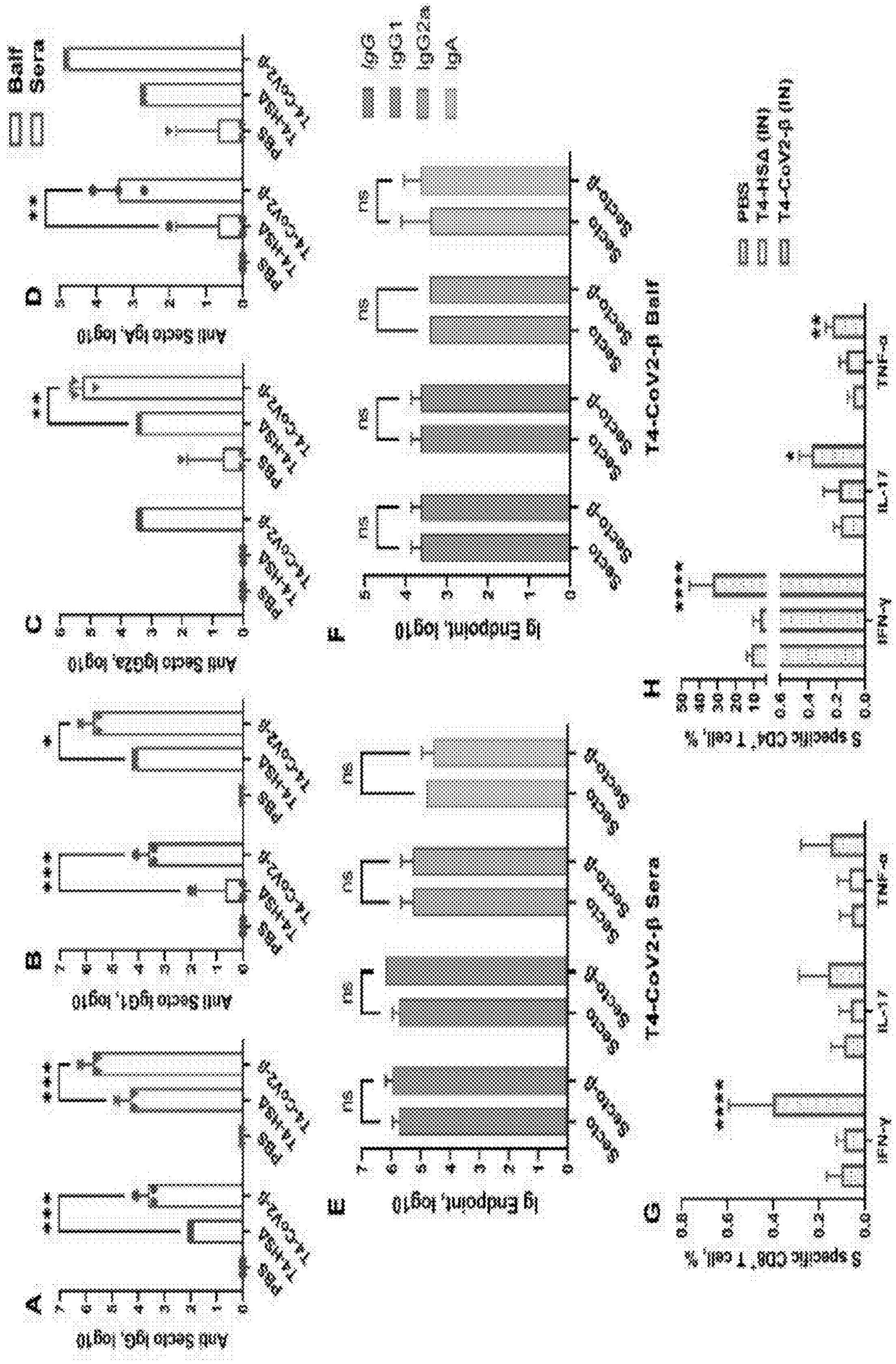
FIGS. 10A-10H illustrate no difference between S-and S-β-binding antibody in T4-CoV-2-β IN immunized mice.

A Beta-Variant Needle-Free T4-CoV-2 Vaccination Stimulates Strong Mucosal, Humoral, and Cellular Immune Responses in Human ACE2 (hACE2) Transgenic Mice To determine if the robust and diverse immune responses elicited by the T4-CoV-2 vaccine, especially the mucosal responses, could be recapitulated in highly susceptible hACE2 knock-in mice, we conducted an independent study using this model. Additionally, we constructed a beta-variant spike trimer (Secto-β) (without any affinity tags) for vaccination as this was a dominant strain at the time of the study causing a major second wave in South Africa and across the globe (31). Secto-β contained four critical mutations (K417N, E484K, N501Y, and D614G) that apparently conferred enhanced transmissibility and lethality, and also partial escape from vaccine-induced immunity (32) (FIG. 9A). The variant S-trimer was expressed in CHOExpi cells and purified by a newly designed protocol (see materials and methods). The purified Secto-β variant trimer behaved similarly as the wild-type (WT) S-trimer and was conjugated to T4 capsid as efficiently as the WT S-trimer through the Spytag-SpyCatcher system (FIG. 9B). In addition, the T4-CoV-2-β vaccine also contained ~100 copies of NP protein packaged inside the capsid since the same phage backbone was used to attach the variant trimer (FIG. 9C). Five-week-old hACE2 AC70 mice were immunized with this vaccine using the same 2-dose i.n. regimen described above (FIGS. 8A and 8B) at a high dose ($\sim 2.5 \times 10^{11}$ phage particles decorated with 20 μg of variant S-trimer) and extensive immunological analyses were performed.

Humoral immune responses: Similar to the binding antibody titers in BALB/c mice (FIGS. 2A-2U and 3A-3H), i.n. immunization with T4-CoV-2-β, but not PBS or T4-vector control, induced high levels of Spike- and RBD-specific IgG and IgA in sera of hACE2-transgenic mice (FIGS. 8C-8J), suggesting a strong systemic humoral immune response. In addition, moderate NP-specific IgG antibodies were also elicited in the T4-CoV-2-β immunized mice (FIG. 9D). Furthermore, high levels of Spike- and RBD-specific IgG and sIgA antibodies were also present in BALF of T4-CoV-2-β vaccinated mice indicating an equally robust mucosal humoral immune responses (FIGS. 8C-8J and 10A-10D). Finally, as in the case of the conventional BALB/c mice, balanced Th1 and Th2 derived IgG2a and IgG1 antibody responses were induced both in sera and BALF, in T4-CoV-2-β immunized mice (FIGS. 8D, 8E, 8G, 8H, 10B, and 10C). There was no significant difference of binding antibody titers between Secto and Secto-β as the coating antigen (FIGS. 10E and 10F), probably because they share a large number of the same epitopes. Collectively, consistent with our findings in BALB/c mice, T4-CoV-2-β i.n. vaccination stimulated strong mucosal and systemic humoral immune responses in hACE2-transgenic mice.

Figures 23A, 23B, 23C:
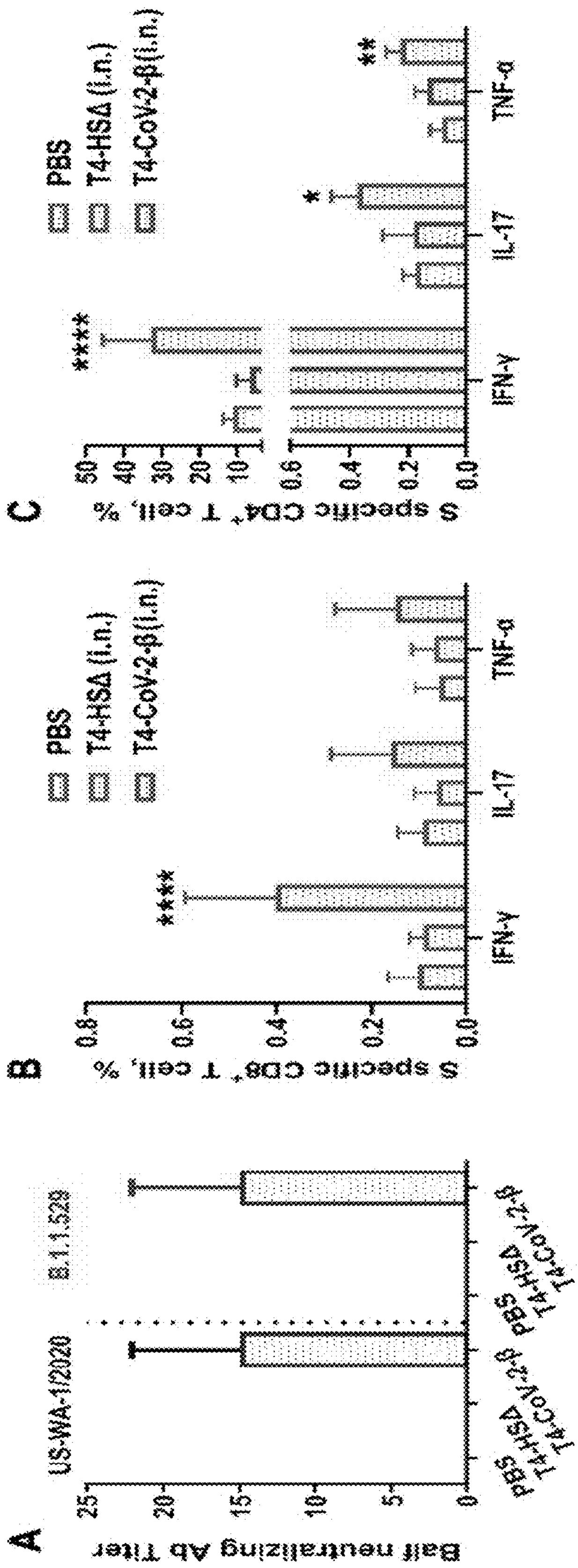
FIGS. 23A-23C illustrate virus neutralization activity in BALF and T cell immune responses in hACE2 transgenic mice.

Importantly, consistent with the broad-spectrum neutralizing activities in BALB/c mice (FIG. 1K), T4-CoV-2-β vaccine elicited comparable virus neutralizing activities to ancestral SARS-COV-2 US-WA-1/2020 and its Delta (B.1.617.2) VOC in hACE2-transgenic mice, while no detectable virus neutralizing activities were detected in PBS or T4 vector control groups (FIG. 8K). T4-CoV-2-β vaccinated sera neutralized the Omicron variant (B.1.1.529) but the titers were 6-fold lower when compared to the WA-1/2020 strain (FIG. 8K). However, neutralization of Omicron was comparable to that of WA-1/2020 in BALF (FIG. 23A), although the BALF titer appeared lower than that of sera, largely due to dilution of the lung lining fluid.

Cell-mediated immune response: As shown in FIGS. 8L and 8M, restimulation of splenocytes ex vivo with S protein showed a similar pattern of $CD8^+$ and $CD4^+$ T cell activation in hACE2 mice as with the conventional BALB/c mice (FIGS. 2L-2U). The percentages of $CD8^+$ and $CD4^+$ T cells positive for IFNγ were substantially elevated in T4-CoV-2-β immunized mice as compared to both PBS and T4 vector control groups (FIGS. 8L and 8M). Interestingly, a much higher percentage of IFNγ positive $CD4^+$ T cells was observed in hACE2 mice than those in conventional BALB/c mice, while the percentage of TNFα or IL-17A positive T cells were similar (FIGS. 10G-10H and FIGS. 23B-23C). T4-CoV-2-β i.n. immunization developed robust spike-specific CD8 and CD4 T cell responses in hACE2-transgenic mice. The substantial induction of IFNγ T cells after vaccination indicated that the T4-CoV-2-β i.n. vaccine consistently induced Th1 cellular immune responses that were shown to be important for reducing disease pathology and enhanced recovery of COVID-19 patients.

Similarly, both Th1 cytokines (IFNγ, IL-2, TNFα, and IL12-p70) (FIGS. 8N-8Q) and Th2 cytokines (IL-4, IL-5, and IL-13) (FIGS. 8R-8T) were induced in T4-CoV-2-β-immunized mice compared to the controls when splenocytes were re-treated with the variant S-trimer. Significantly, very prominent Th1 cytokines IFNγ and IL-2 were produced, indicating Th1-biased cellular immune responses induced by intranasal T4-CoV-2-β vaccine.

Figures 11A, 11B, 11C, 11D, 11E:
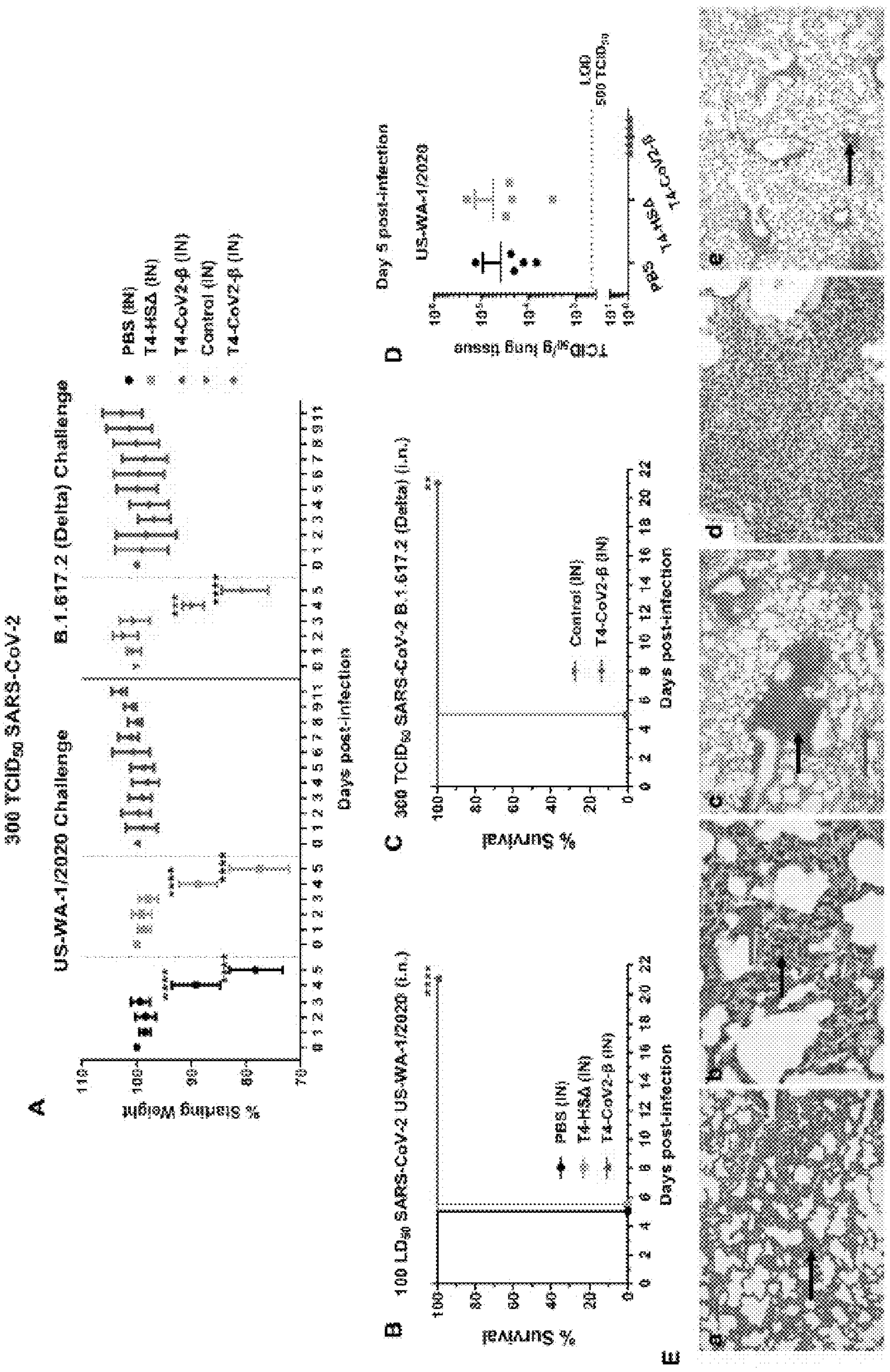
FIGS. 11A-11E illustrate needle-free T4-CoV-2-Beta vaccine provides complete protection against lethal infection by original SARS-COV-2 and delta VOC in hACE2 transgenic mice.
Figures 12A, 12B, 12C, 12D:
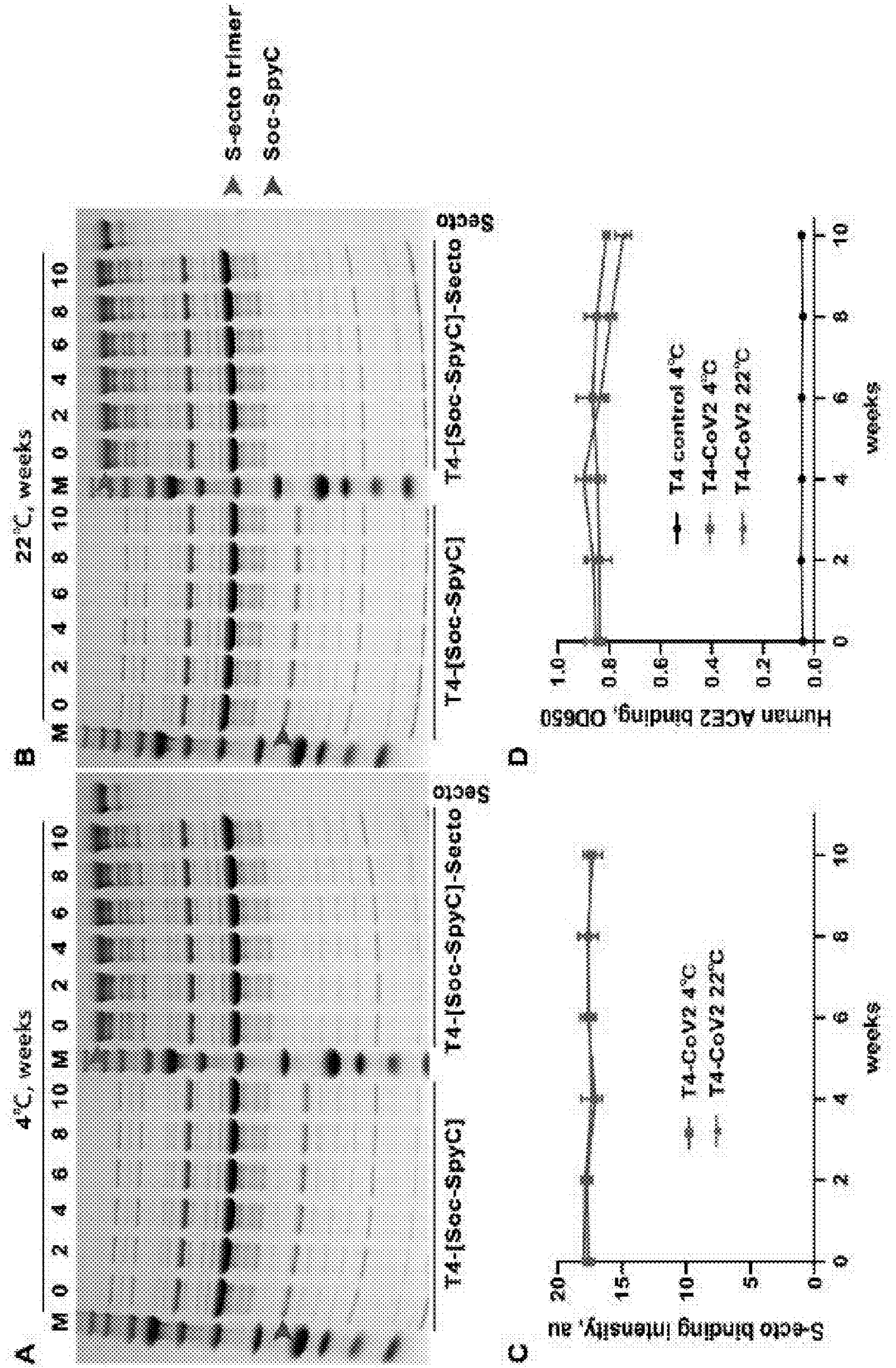
FIGS. 12A-12D illustrate stability of T4-CoV-2 vaccine at 4° C. and at 22° C.

Needle-Free T4-CoV-2-Beta Vaccine Provides Complete Protection and Apparent Sterilizing Immunity Against Lethal Infection by Both the Original SARS-COV-2 and the Delta VOC in hACE2 Transgenic Mice Animal challenge and viral load: Mice were i.n. challenged on day 49, 28-days after the boost, with either SARS-COV-2 US-WA-1/2020 strain or its Delta (B.1.617.2) variant. The highly contagious B1.617.2 shows increased transmissibility compared to the ancestral strain, and studies suggested a high risk of hospitalization compared to the original strain (33). As shown in FIG. 11A, irrespective of the challenge strains, all control animals rapidly lost weight (FIG. 11A) and succumbed to infection (FIGS. 11B and 11C) on day 4-5 post challenge. In contrast, all the T4-CoV-2-β immunized mice only had minimal to no weight loss with a 100% survival rate over the course of 21 days after the challenge. Furthermore, high viral load in the lungs was observed in all the control animals on day 5 p.i., while no live virus was detected in the lungs of T4-CoV-2-β vaccinated mice (FIG. 11D).

Histopathology: As can be seen from FIG. 11E, hACE2 transgenic mice treated with PBS and then challenged with SARS-COV-2-WA-1/2020 strain showed significant interstitial inflammation in alveolar septa (black arrow, FIG. 11Ea, 100*x*) and alveolar hemorrhage. However, there was no evidence of bronchovascular inflammatory infiltrates on day 5 p.i . . . . At 200*x*, widening of interstitium with mononuclear inflammatory infiltrates (black arrow) and septal capillary congestion was clearly visible (red arrow, FIG. 11Eb) in PBS treated and challenged mice.

Based on interstitial inflammation, animals receiving PBS or immunized with T4 vector and then challenged had similar scores of 40±7.1 (PBS group) and 46±18 (T4 vector control group) on day 5 p.i., and the data were not significantly different (p=0.5, Student's t test). Further, on comparing unvaccinated animals (PBS+vector control groups together) with animals receiving the T4-CoV-2-β vaccine, interstitial inflammation was significantly less in immunized mice (p=0.007, Mann-Whitney rank sum test, the results were expressed as median, 25%, and 75% with values of 40, 30, and 52.5 for PBS and T4 vector control immunized and challenged mice compared to 20, 20, and 30 for the T4-CoV-2-β vaccinated and challenged animals) on day 5 p.i . . . .

Importantly, although T4-CoV-2-β i.n. vaccinated and challenged animals had mild interstitial inflammation (blue arrows, FIG. 11Ec), bronchovascular inflammatory infiltrates (black arrows, FIG. 11Ec, 100*x*) were clearly visible, not noted in unvaccinated and challenged mice. The bronchovascular infiltrates were mainly composed of lymphocytes and scattered macrophages (200*x*, FIG. 11Ed). Statistically, for bronchovascular infiltrates, while PBS treated and infected animals had a score of 0.8±0.44, mice vaccinated with the T4 vector alone and challenged had a higher score of 2.2±0.44 (p=0.001, Student's t test and p=0.008 by the Mann-Whitney rank sum test). Thus, T4 vector alone could increase bronchovascular infiltrates.

Finally, when T4 vector and T4-CoV-2-β vaccinated animals (after challenge on day 5 p.i.) were compared, bronchovascular infiltrates were more (p=0.03 Mann-Whitney rank sum test) in the T4-CoV-2-β vaccinated group of mice. Importantly, however, at day 30 p.i., there was no evidence of interstitial pneumonitis and only a mild bronchovascular inflammation (black arrow, FIG. 11Ee, 40*x*) in T4-CoV-2-β vaccinated and challenged mice. These data indicated almost complete recovery of animals from the disease.

Overall, the disclosed data indicated immunological responses induced by the vaccine to clear the infection with 100% survival of the animals. T4 vector, like any other vectors, is expected to activate some non-specific and non-damaging immune responses (e.g., bronchovascular infiltrates) in the host which subside as the vaccine clears from the host.

The T4-CoV-2 Vaccine is Stable at Room Temperature

The current mRNA vaccines require sub-freezing temperatures and the adenovirus-based vaccines require cold temperatures, for storage and distribution. In addition to being costly, vaccines that require a cold chain for storage would face limitations for rapid distribution during a pandemic. Bacteriophage T4 being a resident of the gut, has evolved a stable capsid structure to survive in a hostile environment. Indeed, the T4 phage is stable at extremes of pH and at ambient temperature, properties that are particularly suitable for storage and extending the life of a vaccine (82).

In one embodiment, a protein-based vaccine is stable at ambient temperature for at least 10-weeks.

In one embodiment, a bacteriophage-based vaccine is stable at ambient temperature for at least 10-weeks.

To determine the stability of the T4-CoV-2-β, the vaccine preparations in PBS were stored at 4° C. and at room temperature (22° C.) and samples were taken at various time points and analyzed for stability and functionality. Stability was assessed by any reduction in the intact spike protein associated with phage (due to dissociation), and/or appearance of any degraded protein fragments (due to nonspecific proteolysis), whereas functionality was assessed by the ability of the displayed S-trimers to bind to hACE2 receptor. The data showed (FIGS. 12A-12D) that the T4-CoV-2-β vaccine, by any of these criteria, was completely stable and functional for at least 10-weeks of storage at 4° C. or at 22° C. No significant change was observed either in the covalently conjugated spike molecules (red arrow) or in the unconjugated spike molecules (blue arrow) suggesting that both forms are equally stable. The unconjugated spike molecules represent those subunits that were displayed on the capsid as part of the S-trimer but did not directly crosslink with the SpyCatcher. Furthermore, the backbone phage displaying the SpyCatcher domain as part of the hard-wired recombinant phage, i.e., prior to conjugation with S-trimer, also remained completely stable and functional.

The disclosed data demonstrated stability advantage of the phage T4-CoV-2-β vaccine and coupled with the needle-free intranasal route of administration, this platform provides especially useful features for rapid vaccine distribution during a pandemic.

Discussion

The disclosed studies have established a new bacteriophage T4 mucosal vaccine delivery platform that can be engineered to generate stable, needle- and adjuvant-free, multicomponent/multivalent vaccines against COVID-19 or any emerging and pandemic pathogen. A nanoparticle COVID-19 vaccine containing arrays of ~100 copies of S-trimers on T4 capsid exterior and ~100 copies of NP packaged in its interior when administered to mice intranasally stimulated all arms of the immune system, including strong mucosal immunity that most traditional vaccines do not induce.

The immune responses stimulated by the T4 based COVID-19 vaccine were broad and included: both Th1 and Th2 derived IgG antibodies, virus neutralizing antibodies, $CD4^+$ helper and effector T cells and $CD8^+$ killer T cells, Th1-biased cytokines, and mucosal IgG and sIgA antibodies in BALF. While most of these immune responses were triggered by both i.n. and i.m. routes of vaccine administration, the stimulation was considerably stronger by i.n. immunization. Strikingly, the mucosal IgA was stimulated only by i.n. vaccination. This pattern of broad responses was consistently observed for both WT as well as the beta-variant S-trimers and in conventional BALB/c mice as well as hACE2 transgenic mice. The evidence, thus, is compelling to suggest that vaccine-induced mucosal immunity is a distinctive feature of the needle-free bacteriophage T4 nanoparticle vaccine, which could be further exploited for designing vaccines against other respiratory infections.

In one embodiment, bacteriophage-based vaccine induces higher mucosal IgA and generating mucosal immune responses in addition to humoral and cellular immunities compared to an intramuscular injection.

In one embodiment, bacteriophage-based vaccine induces higher balanced Th1/Th2 antibody and cytokine responses, stronger $CD4^+$ and $CD8^+$ T cell immunity, and higher secretory IgA titers in sera and bronchoalveolar lavage with no effect on gut microbiota compared to an intramuscular injection.

The T4-CoV-2 vaccine induced similar levels of serum virus neutralizing antibody titers against the ancestral SARS-COV-2 WA strain and its two VOC (B.1.135 Beta and B.1.617.2 Delta). The vaccine also induced significant but somewhat diminished neutralizing antibody titers against the Omicron variant. Importantly, similar levels of neutralizing antibody titers were measured in BALF against both WA isolate and its Omicron variant. These data suggested that, possibly, the neutralizing sIgA in BALF might be effective at the entry point by interfering with virus acquisition and at the exit point by clearing the invaded pathogen, thus preventing viral shedding and its further transmission from infected individuals. These are critically important attributes for a vaccine to be able to effectively control the spread of a pandemic pathogen.

The innate immune cells are the first line of defense against pathogens and respond by producing cytokines that activate cells of the adaptive immune system including B and T cells. Generally, T cell immunity is not a correlate of protection after vaccination, but $CD4^+$ T cells are required to support B cell differentiation and to establish memory responses. Th1 cells and cytotoxic T lymphocytes are primarily responsible for host defense against viral infections, although the role of Th2, Th9, and Th17 cells in recruiting different types of innate immune cells to kill invading pathogens is also well documented (45). Th1 cells activate macrophages to produce IFNγ while Th17 cells play a major role in host defense by inducing cytokine release that is independent of IFNγ. Several studies have evaluated T cell responses induced by COVID-19 vaccines and provided evidence of increased production of IFNγ, TNFα, IL-2, and IL-4 in animal models (mice and hamsters) and humans (46-48). Indeed, our studies also demonstrated that both routes of immunization (i.n. and i.m.) with T4-CoV-2 vaccine induced enhanced release of pro-inflammatory/anti-inflammatory as well as Th1/Th2/Th17 cytokines in BALB/c and hACE2 transgenic mice. For example, we observed increased secretion of TNFα, IL-10, as well as IL-2, IL-4, IL-5, IL-12 (p70), IL-13, IFN-γ, and IL-17. Our results also indicated that i.n. route of immunization induced greater cytokine responses compared to i.m. route of vaccination. Overall, our data provided evidence for a balanced Th1/Th2 cell responses triggered by the T4 based COVID-19 vaccine in mice as has also been reported by others upon immunization of mice, hamsters, and macaques with COVID-19 vaccines (49-55). We also noted increased lung Th2 response (IL-12 (p40) and IL-13) and enhanced chemokine production (GM-CSF, KC, MCP-1, and RANTES) in hACE-2 transgenic mice upon immunization with T4-CoV-2 vaccine, indicating recruitment of neutrophils and monocytes to clear the invading pathogen.

Thus, a combination of producing neutralizing antibodies and activation of antigen-specific T cells may act in concert to control SARS-COV-2 infection in our mouse models. Indeed, virus-specific T cells are thought to play a major role in human SARS-COV-2 infection (56-61), and SARS-COV-2 infected macaques were shown to be protected from re-challenge (62). Since a combination of increased humoral and cellular immune responses is a hallmark of vaccine safety and efficacy (63), COVID-19 vaccines developed to date have focused on eliciting either Th1 cell-biased response or balanced Th1 cell/Th2 cell responses (55). However, our T4-CoV-2 vaccines have an added advantage of generating mucosal immune responses in addition to excellent humoral and cellular immunities.

The significance of Th17 immune responses elicited by T4-CoV-2 vaccine is worthy of discussion. Although such responses have been reported during SARS-COV-2 infections (64-65), IL-17 is a pleiotropic cytokine with both beneficial (e.g., enhancing antiviral immune responses) and detrimental functions (66). Indeed, Th17 cells are being recognized as an important T helper subset for immune-mediated protection, and unbalanced Th17 responses are implicated in the pathogenesis of several autoimmune and allergic disorders (67). Involvement of IL-17 in priming enhanced chemokine and G-CSF production in the lung during bacterial pneumonia and its ability to promote anti-microbial responses against pathogens of viral, bacterial, parasitic, and fungal etiology has been reported (66, 68-69).

Further, an accumulation of IL-17-producing T cells in the lungs of vaccinated mice after *Mycobacterium tuberculosis* challenge that preceded the corresponding IFNγ-producing population, suggested that T cells producing IL-17 responded to an infection by recruiting Th1 cells through expression of CXCL chemokines (70). Mucosal delivery of *M. tuberculosis* subunit vaccine has been shown to provide IL-17 dependent protection of mice against pulmonary tuberculosis compared to when the vaccine was delivered by the parenteral route (77). Likewise, vaccine-induced IL-17 provided protection to mice against lung infection with *Pseudomonas aeruginosa* (78) as well as against *Entamoeba histolytica* (69). Since the T4-COVID vaccine provided complete protection to mice with much reduced histopathological lesions, our data support the notion that a delicate balance of Th1/Th2/Th17 and mucosal immune responses were critical in developing COVID-19 vaccines.

It is intriguing why the immune responses to intranasal T4-CoV-2 vaccination is so broad, despite the fact that the T4 phage is non-infectious and the vaccine contains no adjuvants or stimulants. In fact, our previous studies have shown that adding adjuvants such as alum or liposomes did not significantly enhance the levels of immune responses. We speculate that this unusual breadth might be because the T4-CoV-2 vaccine displaying S-trimers mimic the repeat structures and surface molecular patterns of a natural viral pathogen that are recognized by and engage with the Toll-like receptors of the host immune system. Specific interaction with ACE2 receptors of nasal epithelial cells and presentation to resident immune cells might further aid in induction of mucosal immunity as well as strong humoral and cellular immune responses.

The T4-CoV-2 vaccine, regardless of the route of vaccination, conferred complete protection against challenge with lethal doses of SARS-COV-2 virions. Though no major differences were observed between i.n. and i.m. routes of vaccination, the former immunization route clearly protected mice from both the SARS-COV-2 US-WA-1/2020 strain and its Delta (B.1.617.2) variant, considered thus far the most lethal strain. This is consistent with similar vaccine-induced virus neutralizing activity in sera of mice against three SARS-COV-2 strains; US-WA-1/2020, Beta, and Delta variants. Further studies are needed to determine if this breadth was due to the T4 scaffold and/or the Secto-β variant trimers.

Our viral load measurements showed absence of any live virus in the lungs of T4-COVID vaccinated mice whereas the vector control mice were loaded with high levels of virus, in the range of $10^5$ to $10^7$ $TCID_{50}$/g tissue. This indicates that the vaccine might be inducing sterilizing immunity, hence minimizing live virus shedding and host-to-host transmission. This is consistent with the induction of strong mucosal immunity as evident from S-specific IgG and sIgA responses in the lungs of i.n. vaccinated mice. However, even the i.m. vaccinated mice showed sterilizing immunity suggesting that the relatively low levels of mucosal immunity due to S-specific IgG in lungs combined with the strong $CD8^+$ cytotoxic T cells might be sufficient to clear the virus-infected cells.

The effectiveness of i.n. immunization exhibited by the T4-CoV-2 vaccine is of interest for design of vaccines against numerous pathogens that enter the host through mucosal route. The sticky mucous layers in the respiratory tract are present as barriers to pathogens and also possibly interfere with the ability of vaccines to access and activate the mucosal immune system. These may account for poor immunogenicity of most injectable vaccines when administered intranasally. At present, of 96 COVID-19 vaccine candidates in clinical trials, only eight are intranasal vaccines. They are all based on engineered viruses which can efficiently infect human cells and intracellularly express S or RBD antigens from the delivered genes. These include human or chimpanzee adenoviruses (2, 34, 35), live-attenuated influenza virus (36), live-attenuated SARS-COV-2, live-attenuated Newcastle Disease Virus (37, 38), and lentivirus (16). However, these eukaryotic viral vaccines still pose a safety concern and a very low risk of reversion of live-attenuated viral vectors. T4 phage, on the other hand, is non-infectious and the presence of surface molecules such as Hoc fibers that interact with mucin glycoproteins and S-trimers that interact with ACE2 receptors might provide distinct advantages for effective intranasal delivery and presentation to host's mucosal immune system.

Finally, the T4 phage provides a safe and stable platform for vaccine design. While the current injectable mRNA and adenovirus vaccines are considered safe, they do cause side effects such as fatigue, fever and so on, and in rare instances, serious problems such as blood clots occurring alongside a low level of platelets, and heart inflammation, particularly in adolescents. These effects, at least in part, might be due to the use of adjuvants, or lipids and other chemical materials used for encapsulating mRNA vaccines, as well to the use of infectious adenoviral vectors. The long-term safety profile of these vaccines is yet unknown and currently being evaluated. In this context, a noninfectious phage T4-CoV-2 vaccine with no tropism to human cells and no use of adjuvants or chemical stimulants is an advantage. Our microbiome analyses showed no significant changes in the microbiome diversity in mice vaccinated with the T4-CoV-2 vaccine. In human clinical trials and hundreds of T4 phage vaccine immunizations over the years involving mice, rats, rabbits, and macaque animal models and diverse antigens such as anthrax, plague, and HIV did not identify any significant side effects. Furthermore, the T4 phage is one of the most stable virus scaffolds known and our stability studies showed that the T4-CoV-2 vaccine was completely stable at ambient temperature for at least 10-weeks. Therefore, the T4 vaccine that requires no cold chain provides an excellent alternative for global distribution and vaccination of still unvaccinated populations across the world.

Additionally, the T4-CoV-2 vaccine is a strong candidate as an effective booster vaccine. Before this pandemic ends, it is likely that an additional booster vaccination will be needed to protect the global population from emerging variants. None of the current licensed vaccines used worldwide are needle-free or generate significant mucosal responses, which are critically important for minimizing person-to-person transmission. The T4-CoV-2 vaccine that can boost not only the antibody and T cell immune responses but also induce strong mucosal immunity would be the most beneficial one. Furthermore, more than a billion vaccinations across the globe administered the adenovirus-based vaccines, which also stimulate strong anti-vector responses. This pre-existing immunity, particularly the adenovirus capsid neutralizing antibodies, limit the effectiveness of another booster dose using the same vaccine because vaccine delivery requires efficient infection of human cells which would be compromised by immune clearance. Since there is no significant preexisting immunity in humans for T4, the T4-CoV-2 vaccine would be an excellent alternative to boost more than a billion people who already received the adenoviral vaccines.

In conclusion, the disclosed studies have established a bacteriophage T4-based, protein vaccine platform, complementing the current mRNA and DNA vaccine platforms but with certain advantages in terms of route of administration, engineerability, breadth of immune responses, mucosal immunity, and vaccine stability. In particular, broad virus neutralization activity, both systemic and mucosal, T cell immunity, complete protection, and apparent sterilizing immunity, all induced by the same vaccine mean that the T4-CoV-2 vaccine might be able to block viral entry (host's viral acquisition) and viral exit (host's viral shedding), minimizing person to person viral transmission, a strategically critical goal now in view of the emergence of highly transmissible SARS-COV-2 variants. However, additional studies in animal models (hamsters and macaques), Phase 1 human clinical trials, and GMP manufacturing processes are needed to translate the vaccine into mass production and global distribution. These efforts are currently underway.

Figure 13:
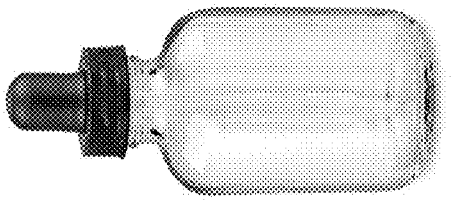
FIG. 13 illustrates a dropper/closure device for delivering a protein-based vaccine according to one embodiment of the present disclosure.
Figure 14:
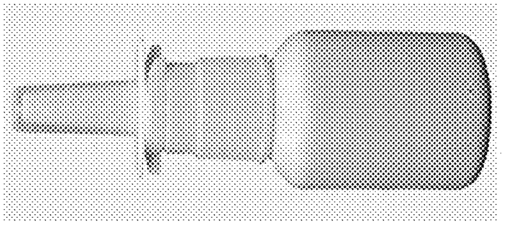
FIG. 14 illustrates a squeeze bottle pump spray device for delivering a protein-basedprotein-based vaccine according to one embodiment of the present disclosure.
Figure 15:
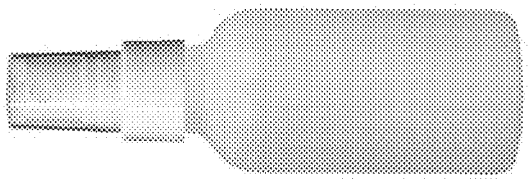
FIG. 15 illustrates an airless and preservative-free spray device for delivering a protein-basedprotein-based vaccine according to one embodiment of the present disclosure.
Figure 16:
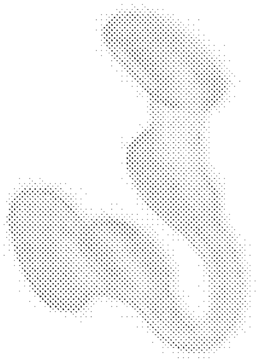
FIG. 16 illustrates a nasal insert device for delivering a protein-basedprotein-based vaccine according to one embodiment of the present disclosure.
Figure 18:
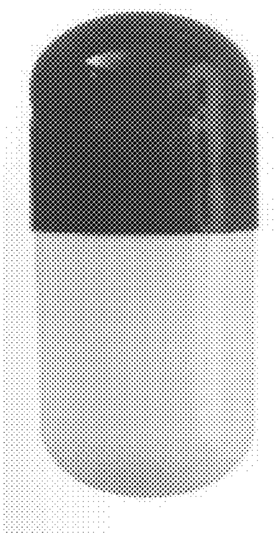
FIG. 18 illustrates a hard capsule for delivering a protein-basedprotein-based vaccine according to one embodiment of the present disclosure.
Figure 19:
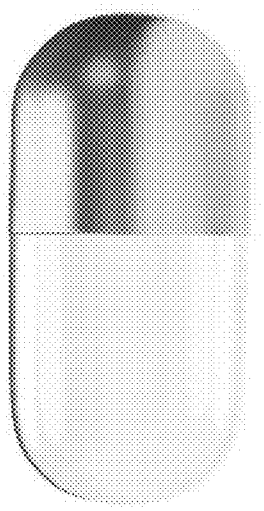
FIG. 19 illustrates a hard capsule with compounds coated differently for delivering a protein-basedprotein-based vaccine according to one embodiment of the present disclosure.
Figure 17:
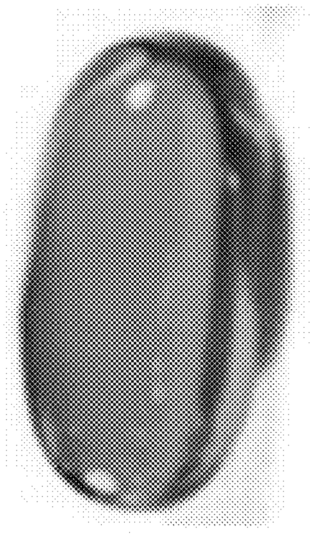
FIG. 17 illustrates a softgel for delivering a protein-basedprotein-based vaccine according to one embodiment of the present disclosure.
Figure 21:
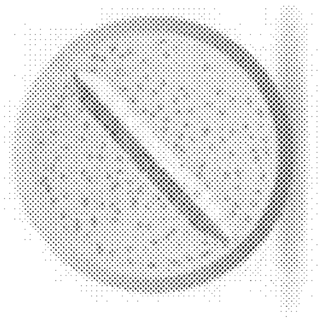
FIG. 21 illustrates a chewable tablet for delivering a protein-basedprotein-based vaccine according to one embodiment of the present disclosure.
Figure 22:
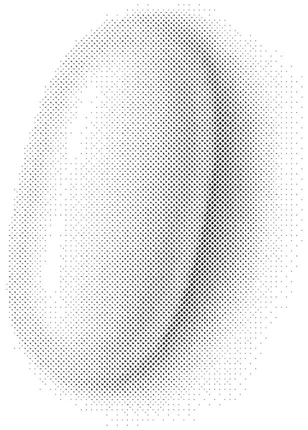
FIG. 22 is a caplet for delivering a protein-basedprotein-based vaccine according to one embodiment of the present disclosure.
Figure 20:
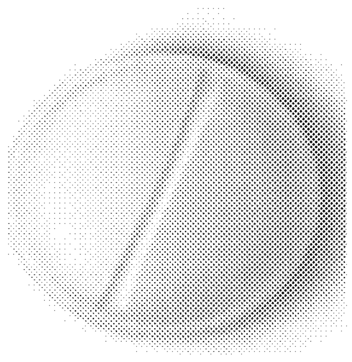
FIG. 20 illustrates a tablet for delivering a protein-basedprotein-based vaccine according to one embodiment of the present disclosure.

While preferred methods and devices of the present disclosure may include nasal administration wherein the device is selected from the group consisting of a container with a dropper/closure device (FIG. 13), a squeeze bottle pump spray (FIG. 14), an airless and preservative-free spray (FIG. 15), and a nasal insert (FIG. 16), it is readily appreciated that skilled artisans may employ other means and techniques for delivering the vaccine, for example, by softgel (FIG. 17), hard capsule (FIG. 18), hard capsule with compounds coated differently (FIG. 19), tablet (FIG. 20), chewable tablet (FIG. 21), caplet (FIG. 22), injection, sugar-coated tablet, delayed-release hard capsule, a topical gel or cream, gummy, a spray, granules, syrups, aerosols, inhalants, suppositories, solution, suspensions, implants containing the composition, a powder, or a sheet, patch or membrane, and etc.

The routes of administration may encompass oral and parenteral routes. For example, the vaccines can be administered orally, by inhalation, or by the subcutaneous, intramuscular, intravenous, transdermal, intranasal, rectal, ocular, topical, sublingual, buccal, or other routes.

The vaccine may be used at appropriate dosages defined by routine testing to obtain optimal pharmacological effect, while minimizing any potential toxic or otherwise unwanted effects.

In determining an effective amount, the dose of a vaccine, a number of factors may be considered such as subject's size, age, and general health, the degree of involvement or the severity of the infection disease, the response of the individual subject, the mode of administration, the bioavailability characteristics of the preparation administered, and etc.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Materials and Methods

T4 bacteriophages and SARS-COV-2 strains

The T4-CoV-2 vaccine is a recombinant T4 phage displaying ~70-100 copies of prefusion-stabilized SARS-COV-2 spike protein ecto-domain trimers (S-trimers) on the surface of 120×86 nm phage capsid. It also harbors SARS-COV-2 nucleocapsid protein (NP) packaged in its core and a 12-amino acid (aa) peptide of the putative external domain of E protein (Ee) on the capsid surface. The S-trimers were displayed through interaction with the small outer capsid protein (Soc) which is attached to CHO EXPi-expressed S-trimers via SpyCatcher-SpyTag conjugation. The Ee peptide was attached through fusion to the highly antigenic outer capsid protein (Hoc) (FIGS. 1A-1C). Both the NP and Ee were hard-wired into T4 genome by CRISPR engineering and incorporated into the phage nanoparticle structure during phage infection to make vaccine production easy. The T4 capsid without carrying the SARS-COV-2 components was used as a control for the study.

Mouse adapted SARS-COV-2 MA10 strain is a gift from Dr. R. Baric, University of North Carolina, Chapel Hill, NC. The first COVID-19 patient isolate SARS-COV-2 US-WA-1/2020, its South African (B.1.351) and Delta (B.1.617.2) variants were obtained through Centers for Disease Control and Prevention (CDC).

Cpf1/Cas9 Spacer

The expression vector pET28b (Novagen®, MA) was used for donor plasmid construction and protein expression plasmid construction. LbCpf1 and SpCas9 plasmids were constructed for spacer cloning (88, 89). Briefly, SpCas9 plasmids were constructed by cloning spacer sequences into the streptomycin-resistant plasmid DS-SPCas (Addgene® no. 48645). Sequences of the spacers are shown in Table 1 below. LbCpf1 plasmid was constructed by replacing Cas9 and its spacer cassette in SpCas9 plasmid with Cpf1 and spacer cassete.

TABLE 1

| Cpfl/Cas9 spacer | | | |
|---|---|---|---|
| Spacers | Sequence (5'-3') | GC, % | |
| Cpf1-39-56-sp1 | gttgcattaatcagcatcag | 40 | 39-56 11 |
| Cpf1-39-56-sp2 | cgcccttgaagttccttctg | 55 | Kbp deletion |
| Cpf1-FarP7K-sp1 | tccactccaagatgctccat | 50 | FarP 7 Kbp |
| Cpf1-FarP7K-sp2 | aaaccgttcaagagtttttg | 35 | deletion; |
| Cpf1-FarP7K-sp3 | aatttagcactcgtggagat | 40 | CAG- CD5- |
| Cpf1-FarP7K-sp4 | tcgcccgaatgaatccagtt | 50 | Sfl or |
| Cpf1-FarP7K-sp5 | ggaagaatccgttaatcgtc | 45 | CAG-CD5-Secto insertion |
| Cpf1-FarP7K-sp6 | ccagtgagttttcacacgaa | 45 | |
| Cpf1-FarP18K-sp1 | cactgatgaagaaacggtgt | 45 | FarP 18 Kbp |
| Cpf1-FarP18K-sp2 | tctactgtaatcatgtccca | 40 | deletion |
| Cpf1-FarP18K-sp3 | tcgttggttcattatacacc | 40 | |
| Cpf1-FarP18K-sp4 | gaattaatcgtgctgataca | 35 | |
| Cpf1-SegF-sp1: | ttccttctccaccctgacca | 55 | SegF |
| Cpf1-SegF-sp2: | atgcagatattagctcacgt | 40 | deletion, |
| Cpf1-SegF-sp3: | accatcgtattttataatta | 20 | CMV-RBD insertion |
| Cpf1-Hoc-sp1: | cagttgatataactcctaaa | 30 | Hoc deletion, |
| Cpf1-Hoc-sp2: | atcaataacccctgtaggtg | 45 | Ee or Ec |
| Cpf1-Hoc-sp3: | gttatgtactaaaaggacct | 35 | insertion |
| Cpf1-Hoc-sp4: | gaaactggtatcatctatac | 35 | |
| Cpf1-Soc-sp1: | agcagaaattagatggaaat | 30 | Soc deletion |
| Cpf1-Soc-sp2: | atattaacataaccgcgagt | 35 | |
| Cpf1-Soc-sp3: | cagcaatccattcagtacgt | 45 | |
| Cpf1-Soc-sp4: | tggaaagtaactggttaata | 30 | |
| Cpf1-Mrh2-sp1: | ttcattacatgtcgtgaaat | 30 | SpyCatcher or |
| Cpf1-Mrh2-sp2: | gatattatcatttcacgaca | 30 | RBD |
| Cpf1-Mrh2-sp3: | aattcgacttgcttctcacc | 45 | insertion |
| Cpf1-IPIII-sp1: | aagtcggaagcctttgtagc | 50 | IPIII deletion; |
| Cpf1-IPIII-sp2: | tgcttggcaaattcaagacc | 45 | NP insertion |
| Cpf1-IPIII-sp3: | ctgatcggtaggtccactca | 55 | |
| Cpf1-IPIII-sp4: | ctacagaagcttcggcaata | 45 | |
| Cpf1-IPII-sp1: | cttctaagttcggcatgtct | 45 | IPII deletion |
| Cpf1-IPII-sp2: | ttacggtctttatogggcaa | 45 | |
| Cas9-IPIII-sp1: | atggaaaggtcttgatgcaa | 40 | IPIII deletion; |
| Cas9-IPIII-sp2: | attatcaatgacccatttac | 30 | NP insertion |
| Cas9-IPIII-sp3: | ggcctttactacagaagctt | 45 | |

Mouse Immunizations

Disclosed embodiments followed recommendations of the National Institutes of Health (NIH) for mouse studies (the Guide for the Care and Use of Laboratory Animals). All animal experiments were approved by the Institutional Animal Care and Use Committee of the Catholic University of America (Washington, DC; Office of Laboratory Animal Welfare assurance number A4431-01) and the University of Texas Medical Branch (Galveston, TX; Office of Laboratory Animal Welfare assurance number A3314-01).

The SARS-COV-2 virus challenge studies were conducted in the animal BSL-3 (ABSL-3) suite at UTMB. 5-6 week-old female BALB/c or hACE2 transgenic mice AC70 (the Jackson laboratory) were randomly grouped (five animals per group) and allowed to acclimate for 14 days. The phage T4-CoV-2 vaccine was administered by either the i.m. or the i.n. route into the hind legs of mice or naris, respectively. For 2-dose regimen, animals received vaccination at days 0 (prime) and 21 (boost), while for 1-dose regimen, the vaccine was given at day 21. Three different number of phage particles possessing 0.8, 4.8, and 20 μg of S-trimer antigens representing ~$1.0\times10^{10}$, $6.3\times10^{10}$ and $2.5\times10^{11}$ phage particles, respectively, were used. Negative control mice received the same volume of PBS or the same amount of T4 control phage (T4 control). Blood was drawn from each animal on day 0 (pre-bleed) and day 42, the isolated sera were stored at −80° C. until further use.

ELISA Determination of IgG and IgG Subtype Antibodies

ELISA plates (Evergreen Scientific) were coated with 100 μl per well of SARS-CoV-2 S-ecto protein (1 μg/ml; Sino Biological), SARS-COV-2 RBD-untagged protein (Sino Biological), SARS-COV-2 NP (Sino Biological), or SARS-COV-2 E protein (1 to 75 amino acids) (Thermo Fisher Scientific) in coating buffer [0.05M sodium carbonate-sodium bicarbonate (pH 9.6)]. After overnight incubation at 4° C., the plates were washed twice with PBS buffer and blocked for 2 h at 37° C. with 200 μl per well of PBS-5% BSA (bovine serum albumin) buffer. Serum samples were diluted with a 5-fold dilution series beginning with an initial 100-fold dilution in PBS-1% BSA. One hundred microliters of diluted serum samples were added to each well, and the plates were incubated at 37° C. for 1 h. After washing five times with PBST (PBS+0.05% Tween 20), the secondary antibody was added at 1:10,000 dilution in PBS-1% BSA buffer (100 μl per well) using either goat anti-mouse IgG-HRP, goat anti-mouse IgG1-HRP, goat anti-mouse IgG2a-HRP (Thermo Fisher Scientific). After incubation for 1 h at 37° C. and five washes with PBST buffer, plates were developed using the TMB (3,3',5,5'-tetramethylbenzidine) Microwell Peroxidase Substrate System (KPL). After 5 to 10 min, the enzymatic reaction was stopped by adding TMB BlueSTOP (KPL) solution. The absorbance was read within 30 min at 650 nm on a VersaMax spectrophotometer. The endpoint titer was defined as the highest reciprocal dilution of serum that gives an absorbance more than twofold of the mean background of the assay.

Virus Neutralization Assay

Neutralizing antibody titers in mouse immune sera against SARS-COV-2 US-WA-1/2020 or its South African, Delta, or Omicron variants were quantified by using Vero E6 cell-based microneutralization assay in the BSL-3 suite as we previously described (7). Briefly, serially 1:2-3 downward diluted mouse sera that were decomplemented at 56° C. for 60 min in a 60 μl volume were incubated for 1 h at room temperature (RT) in duplicate wells of 96-well microtiter plates that contained 120 infectious SARS-COV-2 virus particles in 60 μl in each well. After incubation, 100 μl of the mixture in individual wells was transferred to Vero E6 cell monolayer grown in 96-well microtiter plates containing 100 μl of MEM/2% fetal bovine serum (FBS) medium in each well and was cultured for 72 h at 37° C. before assessing the presence or absence of cytopathic effect (CPE). Neutralizing antibody titers of the tested specimens were calculated as the reciprocal of the highest dilution of sera that completely inhibited virus-induced CPE in at least 50% of the wells and expressed as 50% neutralizing titer.

Bronchoalveolar Lavage and IgA Production

On day 21 after boosting, bronchoalveolar lavage fluids (BALF) were obtained from immunized and control animals by following the protocol as previously described with slight modifications (41). Briefly, the salivary glands were dissected to expose the trachea from euthanized mice (n=5/group). A small incision was made on the ventral face of the trachea and a blunt 26G needle was inserted into the trachea and secured by tying the trachea around the catheter using the floss placed underneath the trachea. An aliquot (600 μL) of PBS was loaded into a 1 mL syringe was flushed in the lungs and BALF collected. The specific sIgA antibody titers were determined by ELISA as we previously described (7).

T Cell Proliferation and Phenotypes as Well as Cytokine Analysis

To measure T-cell proliferation, bromodeoxyuridine (BrdU), a thymidine analog, incorporation method was used. Briefly, spleens were aseptically removed from 5 animals of each indicated group on day 21 after the last immunization dose. Spleens were homogenized and passed through a 70 μm cell strainer to obtain single cell suspension in RPMI 1640 cell culture medium. Splenocytes were then seeded into 24 well tissue culture plates at a density of $2.0\times10^{6}$ cells/well (4 wells/mouse) and stimulated with either SARS-COV-2 S-trimer (10-100 μg/ml) or SARA-2 PepTivator® Peptide S and NP protein Pools (10 μg/ml each, Miltenyi Biotec) for 72 h at 37° C. BrdU (BD Bioscience) was added to a final concentration of 10 μM during the last 18 h of incubation with the stimulants to be incorporated into the splenocytes (83-84). Subsequently, the BrdU-labeled splenocytes were surface stained for T-cell (CD3e-APC; eBioscience) marker after blocking with anti-mouse CD16/32 antibodies (BioLegend). Cells were then permeabilized and treated with DNase to expose BrdU epitopes followed by anti-BrdU-FITC and 7-AAD (7-amino-actinomycin D) staining by using BD Pharmingen FITC BrdU Flow Kit. The splenocytes were then subjected to flow cytometry, and data analyzed as we previously described (85-87). The percent of BrdU positive cells in CD3 positive populations were calculated using FACSDiva software.

To measure T-cell phenotypes, the above overnight stimulated splenocytes were similarly blocked with anti-mouse CD16/32 antibodies (BioLegend) and stained with Fixable Viability Dye eFluor™ 506 (eBioscience) followed by APC anti-mouse CD3e (eBioscience), PE/Dazzle 594 anti-mouse CD4 (BioLegend), FITC anti-mouse CD8 (BioLegend) for CD3, CD4 and CD8 T-cell surface markers, respectively. Cells were then permeabilized for intracellular staining with PerCP/Cy5.5 anti-mouse IFNγ, PE/Cy7 anti-mouse IL-17A (BioLegend), eFluor 450 anti-mouse TNFα (eBioscience), and analyzed by flow cytometry.

To assess cytokine production, cell supernatants were collected after stimulation with S-trimers as described above for 72 h at 37° C. Cytokines in the supernatants were then measured by using Bio-Plex Pro mouse cytokine 23-plex assay (Bio-Rad Laboratories). Likewise BALF from control and immunized mice was used to measure cytokines.

16S rRNA Gene Sequencing and Microbiome Analysis

Fecal pellets were collected from 5 animals of each indicated group on day 21 after the last immunization dose. Total genomic DNA was extracted from the fecal matter using methods previously described (42, 43). DNA samples were further purified using a DNA Clean and Concentrator kit (Zymo Research).

The above extracted microbial DNA was then subjected to amplification and sequencing of the V4 region of the 16S rRNA gene by using a NEXTflex 16S V4 Amplicon Seq kit 2.0 (PerkinElmer), and sequences were generated on the Illumina MiSeq platform (Illumina). Raw reads were filtered using the Lotus pipeline (44), followed by de novo clustering to operational taxonomic units (OTUs) at 97% sequence identity with UPARSE (79). Bacterial diversity and community composition were evaluated using QIIME v1.8 (80), and taxonomy assignment of the representative sequence for each OTU was completed using the RDP classifier algorithm and the SILVA reference database (v123) (81).

Animal Challenges

Immunized and control mice were first ear tagged and their initial weights recorded. Mice were then anesthetized and intranasally challenged with 60 μl of either SARS-COV-2 MA10 strain for conventional mice or SARS-COV-2 US-WA-1/2020 strain or the Delta variant (B.1.617.2) for hACE2 transgenic mice. The challenge dose was ~$10^5$ median tissue culture infectious dose ($TCID_{50}$). For hACE2 Tg mice, the challenge dose was 300 $TCID_{50}$. The animals were monitored for the onset of morbidity (weight loss and other signs of illness, every day) and mortality over the indicated period.

Histopathology Studies

Lung tissues were excised from euthanized animals (immunized and control) at 2-5 days post challenge and immersion fixed in 10% neutral buffered formalin. After fixation, tissues were sectioned at 5 μm, mounted on glass slides, and stained with hematoxylin and eosin (HE) and MOVAT for histopathological analysis (Department of Pathology, UTMB). Staining with MOVAT helps in better visualizing tissue architecture. Histopathological analysis of lung sections from Balb/c mice was performed based on three parameters: mononuclear inflammatory infiltrate around bronchovascular bundles, interstitial inflammation, and alveolar exudate/hemorrhage. Scores for bronchovascular infiltrates ranged from 0 (normal) to 3, as follow: 1-Occasional mononuclear infiltrates, 5-10 microns thick; 2: multifocal mononuclear infiltrates, 5-20 microns thick; and 3-Diffuse mononuclear infiltrates, >20 microns thick. The scores for interstitial inflammation were as follow: 1-occasional areas of widened alveolar septa; 2. multifocal areas of widened alveolar septa; and 3-diffused widening of alveolar septa. For alveolar exudate/hemorrhage, the scores were: 1-occasional areas of alveolar exudate/hemorrhage; 2-multifocal areas of alveolar exudate/hemorrhage; and 3-diffused areas of alveolar exudate/hemorrhage. The combined scores for the vector control group and the T4-CoV-2 vaccine group were analyzed using the Student's t-test.

For hACE2 Tg mice, histopathological analysis was performed based on these parameters: interstitial inflammation/alveolar exudate and mononuclear inflammatory infiltrate around bronchovascular (BV) bundles. Interstitial inflammation/alveolar exudates were scored based on percentage of the lung surface area involved (0-100%), while scores for BV infiltrate ranged from 0 (normal) to 3 as follow: 1-occasional mononuclear infiltrates, 5-10 microns thick; 2-multifocal mononuclear infiltrates, 5-20 microns thick; and 3-Diffused mononuclear infiltrates, >20 microns thick. The scores for the intranasal PBS control group, T4 vector control group, and the T4-CoV-2 vaccinated group were analyzed using the Student's t-test if the groups passed normality test (Shapiro-Wilk) or Mann-Whitney Rank sum test if the normality test failed.

Statistics

All in vitro and in vivo data were presented as means±SEM except where indicated. Statistical analyses were performed by GraphPad Prism 9.0 software using one-way or two-way analysis of variance (ANOVA) with Tukey's post hoc test or multiple t-test according to the generated data. We used Kaplan-Meier with log-rank (Mantel-Cox) test for animal survival studies. Significant differences between two groups were indicated by *$P<0.05$,  $P<0.01$, * $P<0.001$, and **** $P<0.0001$. ns indicates not significant.

REFERENCES

The following references are referred to above and are incorporated herein by reference:

1. Tregoning, J. S., et al. Progress of the COVID-19 vaccine effort: viruses, vaccines and variants versus efficacy, effectiveness and escape. *Nature Reviews Immunology* 21, 626-636 (2021).
2. Hassan, A. O., et al. A Single-Dose Intranasal ChAd Vaccine Protects Upper and Lower Respiratory Tracts against SARS-COV-2. *Cell* 183, 169-184 (2020).
3. Callaway, E., et al. How to redesign COVID vaccines so they protect against variants. *Nature* 590, 15-16 (2021).
4. Mercado, N. B., et al. Single-shot Ad26 vaccine protects against SARS-COV-2 in rhesus macaques. *Nature* 586, 583-588 (2020).
5. Corbett, K. S., et al. SARS-COV-2 mRNA vaccine design enabled by prototype pathogen preparedness. *Nature* 586, 567-571 (2020).
6. Tiboni, M., et al. Nasal vaccination against SARS-COV-2: Synergistic or alternative to intramuscular vaccines? *International journal of pharmaceutics* 603, 120686 (2021).
7. Zhu, J., et al. A universal bacteriophage T4 nanoparticle platform to design multiplex SARS-COV-2 vaccine candidates by CRISPR engineering. *Science advances* 7, eabh1547 (2021).
8. Keeble, A. H., et al. Approaching infinite affinity through engineering of peptide-protein interaction. *Proceedings of the National Academy of Sciences of the United States of America* 116, 26523-26533 (2019).
9. Tao, P., et al. Bacteriophage T4 nanoparticles for vaccine delivery against infectious diseases. *Advanced drug delivery reviews* 145, 57-72 (2018).
10. Yao, H., et al. Molecular Architecture of the SARS-COV-2 Virus. *Cell* 183, 730-738 (2020).
11. Hou, Y. J., et al. SARS-COV-2 Reverse Genetics Reveals a Variable Infection Gradient in the Respiratory Tract. *Cell* 182, 429-446 (2020).
12. Van Belleghem, J. D., et al. Interactions between Bacteriophage, Bacteria, and the Mammalian Immune System. *Viruses* 11, 10 (2019).
13. Barr, J. J., et al. Bacteriophage adhering to mucus provide a non-host-derived immunity. *Proceedings of the National Academy of Sciences of the United States of America* 110, 10771-10776 (2013).
14. Barr, J. J., et al. Subdiffusive motion of bacteriophage in mucosal surfaces increases the frequency of bacterial encounters. *Proceedings of the National Academy of Sciences* 112, 13675-13680 (2015).
15. Rubin, R., Trying to block SARS-COV-2 transmission with intranasal vaccines. *Jama* 326, 1661-1663 (2021).

16. Focosi, D., et al. Mucosal vaccines, sterilizing immunity, and the future of sars-cov-2 virulence. *Viruses* 14, 187 (2022).
17. Ku, M. W., et al. Intranasal vaccination with a lentiviral vector protects against SARS-COV-2 in preclinical animal models. *Cell host & microbe* 29, 236-249 (2021).
18. Afkhami, S., et al. Respiratory mucosal delivery of next-generation COVID-19 vaccine provides robust protection against both ancestral and variant strains of SARS-COV-2. *Cell* 185, 896-915 (2022).
19. Sterlin, D., et al. IgA dominates the early neutralizing antibody response to SARS-CoV-2. *Science translational medicine* 13, eabd2223 (2021).
20. Mistry, P., et al. SARS-COV-2 variants, vaccines, and host immunity. *Frontiers in immunology* 12, 5400 (2022).
21. Castro, F., et al. Interferon-gamma at the crossroads of tumor immune surveillance or evasion. *Frontiers in immunology* 9, 847 (2018).
22. Sadarangani, M., et al. Immunological mechanisms of vaccine-induced protection against COVID-19 in humans. *Nature Reviews Immunology* 21, 475-484 (2021).
23. Sette, A., et al. Adaptive immunity to SARS-COV-2 and COVID-19. *Cell* 184, 861-880 (2021).
24. Krammer, F., SARS-COV-2 vaccines in development. *Nature* 586, 516-527 (2020).
25. Macpherson, A. J., et al. The immune geography of IgA induction and function. *Mucosal immunology* 1, 11-22 (2008).
26. Su, F., et al. Induction of mucosal immunity through systemic immunization: Phantom or reality? *Human vaccines & immunotherapeutics* 12, 1070-1079 (2016).
27. Asahi-Ozaki, Y., et al. Secretory IgA antibodies provide cross-protection against infection with different strains of influenza B virus. *Journal of medical virology* 74, 328-335 (2004).
28. Renegar, K. B., et al. Role of IgA versus IgG in the Control of Influenza Viral Infection in the Murine Respiratory Tract. *The Journal of Immunology* 173, 1978-1986 (2004).
29. Lapuente, D., et al. Protective mucosal immunity against SARS-COV-2 after heterologous systemic prime-mucosal boost immunization. *Nature communications* 12, 1-14 (2021).
30. Ruck, C. E., et al. Vaccine interactions with the infant microbiome: Do they define health and disease? *Frontiers in Pediatrics* 8, 565368 (2020).
31. Chen, J., et al. The intestinal microbiota and improving the efficacy of COVID-19 vaccinations. *Journal of Functional Foods* 87, 104850 (2021).
32. Tegally, H., et al. Detection of a SARS-COV-2 variant of concern in South Africa. *Nature* 592, 438-443 (2021).
33. Ahmad, L., Implication of SARS-COV-2 immune escape spike variants on secondary and vaccine breakthrough infections. *Frontiers in immunology* 12, 4563 (2021).
34. Liu, Y., et al. The reproductive number of the Delta variant of SARS-COV-2 is far higher compared to the ancestral SARS-COV-2 virus. *Journal of Travel Medicine* 28, taab124 (2021).
35. King, R. G., et al. Single-dose intranasal administration of AdCOVID elicits systemic and mucosal immunity against SARS-COV-2 and fully protects mice from lethal challenge. *Vaccines* 9, 881 (2021).
36. Van Doremalen, N., et al. Intranasal ChAd0x1 nCOV-19/AZD1222 vaccination reduces shedding of SARS-COV-2 D614G in rhesus macaques. *BioRxiv* (2021).
37. An, D., et al. Protection of K18-hACE2 mice and ferrets against SARS-COV-2 challenge by a single-dose mucosal immunization with a parainfluenza virus 5-based COVID-19 vaccine. *Science Advances* 7, eabi5246 (2021).
38. Park, J.-G., et al. Immunogenicity and protective efficacy of an intranasal live-attenuated vaccine against SARS-COV-2. *iScience* 24, 102941 (2021).
39. Sun, W., et al. A Newcastle disease virus expressing a stabilized spike protein of SARS-CoV-2 induces protective immune responses. *Nature communications* 12, 1-14 (2021).
40. Simpson, C. R., et al. First-dose ChAd0x1 and BNT162b2 COVID-19 vaccines and thrombocytopenic, thromboembolic and hemorrhagic events in Scotland. *Nature medicine* 27, 1290-1297 (2021).
41. Van, H., et al. Bronchoalveolar lavage of murine lungs to analyze inflammatory cell infiltration. *JoVE (Journal of Visualized Experiments)* 123, e55398 (2017).
42. Salonen, A., et al. Comparative analysis of fecal DNA extraction methods with phylogenetic microarray: effective recovery of bacterial and archaeal DNA using mechanical cell lysis. *Journal of microbiological methods* 81, 127-134 (2010).
43. Yu, Z., et al. Improved extraction of PCR-quality community DNA from digesta and fecal samples. *Biotechniques* 36, 808-812 (2004).
44. Hildebrand, F., et al. LotuS: an efficient and user-friendly OTU processing pipeline. *Microbiome* 2, 1-7 (2014).
45. Sallusto, F. Heterogeneity of human CD4$^+$ T cells against microbes. *Annual review of immunology* 34, 317-334 (2016).
46. Rauch, S., et al. mRNA vaccine CVnCOV protects non-human primates from SARS-CoV-2 challenge infection. *Biorxiv* 2020-12 (2020).
47. Lipsitch, M., et al. Cross-reactive memory T cells and herd immunity to SARS-COV-2. *Nature Reviews Immunology* 20, 709-713 (2020).
48. Sahin, U., et al. COVID-19 vaccine BNT162b1 elicits human antibody and TH1 T cell responses. *Nature* 586, 594-599 (2020).
49. Vogel, A. B., et al. A prefusion SARS-COV-2 spike RNA vaccine is highly immunogenic and prevents lung infection in non-human primates. *BioRxiv* 2020-09 (2020).
50. Vogel, A. B., et al. BNT162b vaccines are immunogenic and protect non-human primates against SARS-COV-2. *bioRxiv* 2020-12 (2020).
51. Corbett, K. S., et al. SARS-COV-2 mRNA vaccine design enabled by prototype pathogen preparedness. *Nature* 586, 567-571 (2020).
52. Bos, R., et al. Ad26 vector-based COVID-19 vaccine encoding a prefusion-stabilized SARS-COV-2 Spike immunogen induces potent humoral and cellular immune responses. *npj Vaccines* 5, 91 (2020).
53. Kalnin, K. V., et al. Immunogenicity and efficacy of mRNA COVID-19 vaccine MRT5500 in preclinical animal models. *npj Vaccines* 6, 61 (2021).
54. Sadarangani, M., et al. Immunological mechanisms of vaccine-induced protection against COVID-19 in humans. *Nature Reviews Immunology* 21, 475-484 (2021).
55. DiPiazza, A. T., et al. COVID-19 vaccine mRNA-1273 elicits a protective immune profile in mice that is not associated with vaccine-enhanced disease upon SARS-COV-2 challenge. *Immunity* 54, 1869-1882 (2021).
56. Grifoni, A., et al. Targets of T cell responses to SARS-COV-2 coronavirus in humans with COVID-19 disease and unexposed individuals. *Cell* 181, 1489-1501 (2020).

57. Zheng, H-Y., et al. Elevated exhaustion levels and reduced functional diversity of T cells in peripheral blood may predict severe progression in COVID-19 patients. *Cellular & molecular immunology* 17, 541-543 (2020).
58. Zheng, H-Yi., et al. Longitudinal transcriptome analyses show robust T cell immunity during recovery from COVID-19. *Signal transduction and targeted therapy* 5, 294 (2020).
59. Chen, G., et al. Clinical and immunological features of severe and moderate coronavirus disease 2019. *The Journal of clinical investigation* 130, 2620-2629 (2020).
60. Xiong, Y., et al. Transcriptomic characteristics of bronchoalveolar lavage fluid and peripheral blood mononuclear cells in COVID-19 patients. *Emerging microbes & infections* 9, 761-770 (2020).
61. Braun, J., et al. SARS-COV-2-reactive T cells in healthy donors and patients with COVID-19. *Nature* 587, 270-274 (2020).
62. Chandrashekar, A., et al. SARS-COV-2 infection protects against rechallenge in rhesus macaques. *Science* 369, 812-817 (2020).
63. Lambert, P-H., et al. Consensus summary report for CEPI/BC Mar. 12-13, 2020 meeting: assessment of risk of disease enhancement with COVID-19 vaccines. *Vaccine* 38, 4783-4791 (2020).
64. Hotez, P. J., et al. The potential role of Th17 immune responses in coronavirus immunopathology and vaccine-induced immune enhancement. *Microbes and infection* 22, 165-167 (2020).
65. Shibabaw, T. Inflammatory cytokine: IL-17A signaling pathway in patients present with COVID-19 and current treatment strategy. *Journal of inflammation research* 673-680 (2020).
66. Ma, W-T., et al. The protective and pathogenic roles of IL-17 in viral infections: friend or foe?. *Open biology* 9, 190109 (2019).
67. Tesmer, L. A., et al. Th17 cells in human disease. *Immunological reviews* 223, 87-113 (2008).
68. Anipindi, V. C., et al. IL-17 production by γδ+ T cells is critical for inducing Th17 responses in the female genital tract and regulated by estradiol and microbiota. *ImmunoHorizons* 3, 317-330 (2019).
69. Guo, X., et al. $CD4^+$ and $CD8^+$ T cell- and IL-17-mediated protection against *Entamoeba histolytica* induced by a recombinant vaccine. *Vaccine* 29, 772-777 (2011).
70. Khader, S. A., et al. IL-23 and IL-17 in the establishment of protective pulmonary $CD4^+$ T cell responses after vaccination and during *Mycobacterium tuberculosis* challenge. *Nature immunology* 8, 369-377 (2007).
77. Counoupas, C., et al. Mucosal delivery of a multistage subunit vaccine promotes development of lung-resident memory T cells and affords interleukin-17-dependent protection against pulmonary tuberculosis. *npj Vaccines* 5, 105 (2020).
78. Priebe, G. P., et al. IL-17 is a critical component of vaccine-induced protection against lung infection by lipopolysaccharide-heterologous strains of *Pseudomonas aeruginosa. The Journal of Immunology* 181, 4965-4975 (2008).
79. Edgar, R. C. UPARSE: highly accurate OTU sequences from microbial amplicon reads. *Nature methods* 10, 996-998 (2013).
80. Caporaso, J. G., et al. QIIME allows analysis of high-throughput community sequencing data. *Nature methods* 7, 335-336 (2010).
81. Quast, C., et al. The SILVA ribosomal RNA gene database project: improved data processing and web-based tools. *Nucleic acids research* 41, D590-D596 (2012).
82. Jończyk, E., et al. The influence of external factors on bacteriophages. *Folia microbiologica* 56, 191-200 (2011).
83. Endl, E., et al. Analysis of cell cycle-related Ki-67 and p120 expression by flow cytometric BrdUrd-Hoechst/7AAD and immunolabeling technique. *Cytometry: The Journal of the International Society for Analytical Cytology* 29, 233-241 (1997).
84. Penit, C. In vivo thymocyte maturation. BUdR labeling of cycling thymocytes and phenotypic analysis of their progeny support the single lineage model. *Journal of immunology* (*Baltimore, Md.:* 1950) 137, 2115-2121 (1986).
85. Kilgore, P. B., et al. A new generation needle- and adjuvant-free trivalent plague vaccine utilizing adenovirus-5 nanoparticle platform. *npj Vaccines* 6, 21 (2021).
86. Kilgore, P. B., et al. Combinatorial Viral Vector-Based and Live Attenuated Vaccines without an Adjuvant to Generate Broader Immune Responses to Effectively Combat Pneumonic Plague. *Mbio* 12, e03223-21 (2021).
87. Tiner, B. L., et al. Immunisation of two rodent species with new live-attenuated mutants of *Yersinia pestis* CO92 induces protective long-term humoral- and cell-mediated immunity against pneumonic plague. *npj Vaccines* 1, 1-12 (2016).
88. Tao, P., et al. Engineering of Bacteriophage T4 Genome Using CRISPR-Cas9. *ACS Synthetic Biology* 6, 1952-1961 (2017).
89. Liu, Y., et al. Covalent modifications of bacteriophage genome confer a degree of resistance to bacterial CRISPR systems. *Journal of Virology* 94, e01630-20 (2020).

All documents, patents, journal articles and other materials cited in the present application are incorporated herein by reference.

While the present disclosure has been disclosed with references to certain embodiments, numerous modification, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A protein-based vaccine comprising:

a bacteriophage;

an antigen; and a nucleoprotein, wherein the antigen is attached to an outer capsid protein of the bacteriophage, wherein the nucleoprotein is packaged inner capsid protein of the bacteriophage, wherein the protein-based vaccine is a mucosal vaccine, and wherein the protein-based vaccine is needle and adjuvant-free.

2. The protein-based vaccine of claim 1, wherein the bacteriophage is selected from the group consisting of: Lambda phage, *Bacillus* phage Phi29, *Escherichia coli* phages T2, T3, T4, and T7, Enterobacteriaphage P22, and phage SPP1.

3. The protein-based vaccine of claim 2, wherein the bacteriophage is *Escherichia coli* phage T4.

4. The protein-based vaccine of claim 1, wherein the antigen is a prefusion-stabilized spike ecto-domain trimer.

5. The protein-based vaccine of claim 1, wherein the protein-based vaccine is stable at ambient temperature for at least 10-weeks.

6. The protein-based vaccine of claim 1, wherein the protein-based vaccine is administered to a subject via an intranasal route.

7. The protein-based vaccine of claim 6, wherein the subject is a human.

8. The protein-based vaccine of claim 6, wherein the subject is selected from the group consisting of: a mammal, a reptile, a bird, a fish, an amphibian, and an invertebrate.

9. The protein-based vaccine of claim 1, wherein the protein-based vaccine is administered to a subject with a pharmaceutical carrier.

10. The protein-based vaccine of claim 9, wherein the subject is a human.

11. The protein-based vaccine of claim 9, wherein the subject is selected from the group consisting of: a mammal, a reptile, a bird, a fish, an amphibian, and an invertebrate.

12. The protein-based vaccine of claim 1, wherein the protein-based vaccine is administered to a subject with a nutraceutical carrier.

13. The protein-based vaccine of claim 12, wherein the subject is a human.

14. The protein-based vaccine of claim 12, wherein the subject is selected from the group consisting of: a mammal, a reptile, a bird, a fish, an amphibian, and an invertebrate.

15. The protein-based vaccine of claim 1, wherein the protein-based vaccine is delivered to a subject with at least one selected from the group consisting of: a softgel, a hard capsule, a hard capsule with compounds coated differently, a tablet, a chewable tablet, and a caplet.

16. The protein-based vaccine of claim 15, wherein the subject is a human.

17. The protein-based vaccine of claim 15, wherein the subject is selected from the group consisting of: a mammal, a reptile, a bird, a fish, an amphibian, and an invertebrate.

18. A method of treating of a subject comprising:

administering a therapeutically effective amount of the protein-based vaccine of claim 1 to the subject.

19. The method of claim 18, wherein the subject is a human.

20. The method of claim 18, wherein the subject is selected from the group consisting of: a mammal, a reptile, a bird, a fish, an amphibian, and an invertebrate.

21. A kit comprising a therapeutically effective amount of the protein-based vaccine of claim 1, wherein the protein-based vaccine at least stops or reverses an infection disease.

22. The kit of claim 21, wherein the bacteriophage is selected from the group consisting of: Lambda phage, *Bacillus* phage Phi29, *Escherichia coli* phages T2, T3, T4, and T7, Enterobacteriaphage P22, and phage SPP1.

23. A bacteriophage-based vaccine comprising: a bacteriophage; a spike protein; and a nucleoprotein, wherein the bacteriophage is decorated with the spike protein on a surface of a capsid protein of the bacteriophage, wherein the nucleoprotein is hard-wired by human engineering and packed inner capsid protein of the bacteriophage, wherein the bacteriophage-based vaccine is a mucosal vaccine, and wherein the bacteriophage-based vaccine is needle and adjuvant-free.

24. The bacteriophage-based vaccine of claim 23, wherein the human engineering is CRISPR engineering.

25. The bacteriophage-based vaccine of claim 23, wherein the bacteriophage-based vaccine is stable at ambient temperature for at least 10-weeks.

26. The bacteriophage-based vaccine of claim 23, wherein the bacteriophage-based vaccine further comprises a peptide of an E protein.

27. The bacteriophage-based vaccine of claim 26, wherein a 12-amino acid peptide of a putative external domain of the E protein is fused to an outer capsid protein (Hoc) displayed on a capsid surface of the bacteriophage.

28. The bacteriophage-based vaccine of claim 27, wherein the nucleoprotein, the E protein, and SpyCatcher genes are hard-wired by inserting respective expressible genes into the bacteriophage genome producing packaging nucleoprotein molecules inside the capsid, the peptide of the E protein at a tip of a Hoc fiber, and a SpyCatcher as a small outer capsid protein (Soc) fusion on the capsid surface.

29. The bacteriophage-based vaccine of claim 28, wherein a Spytagged Spike Trimer purified from CHOExpi cells are conjugated to a Soc-SpyCatcher.

30. The bacteriophage-based vaccine of claim 23, wherein the bacteriophage is T4 bacteriophage, and wherein the spike protein is a prefusion-stabilized spike ecto-domain trimer.

31. The bacteriophage-based vaccine of claim 23, wherein the spike protein is covalently attached to a small outer capsid protein (Soc) of the bacteriophage through a SpyCatcher-SpyTag conjugation system.

32. The bacteriophage-based vaccine of claim 23, wherein the bacteriophage-based vaccine has repetitive and symmetrical arrays of the spike protein on a surface of the bacteriophage, resembling pathogen-associated molecular patterns present on human viral pathogens.

33. The bacteriophage-based vaccine of claim 23, wherein the bacteriophage-based vaccine induces higher virus neutralization antibody titers against multiple variants than an intramuscular injection.

34. The bacteriophage-based vaccine of claim 23, wherein the bacteriophage-based vaccine induces higher mucosal IgA and generating mucosal immune responses in addition to humoral and cellular immunities compared to an intramuscular injection.

35. The bacteriophage-based vaccine of claim 23, wherein the bacteriophage-based vaccine induces higher balanced Th1/Th2 antibody and cytokine responses, stronger $CD4^+$ and $CD8^+$ T cell immunity, and higher secretory IgA titers in sera and bronchoalveolar lavage with no effect on gut microbiota compared to an intramuscular injection.

36. A method of administering a protein-based vaccine comprising: administering a protein-based vaccine comprising recombinant phage via intranasal passageway of a subject, wherein a device comprises a therapeutically effective amount of the protein-based vaccine, wherein the protein-based vaccine at least stops or partially reverses an infection disease, wherein the protein-based vaccine comprises: a bacteriophage; an antigen; and a nucleoprotein, wherein the antigen is attached to outer capsid protein of the bacteriophage, wherein the nucleoprotein is packaged inner capsid protein of the bacteriophage, wherein the protein-based vaccine is a mucosal vaccine, and wherein the protein-based vaccine is needle and adjuvant-free.

37. The method of claim 36, wherein the bacteriophage is selected from the group consisting of Lambda phage, *Bacillus* phage Phi29, *Escherichia coli* phages T2, T3, T4, and T7, Enterobacteriaphage P22, and phage SPP1.

38. The method of claim 37, wherein the bacteriophage is *Escherichia coli* phage T4.

39. The method of claim 36, wherein the antigen is a prefusion-stabilized spike ecto-domain trimer.

40. The method of claim 36, wherein the protein-based vaccine is stable at ambient temperature for at least 10-weeks.

41. The method of claim 36, wherein the protein-based vaccine is administered to the subject twice during a period of time.

42. The method of claim 36, wherein the subject is a human.

43. The method of claim 36, wherein the subject is selected from the group consisting of a mammal, a reptile, a bird, a fish, an amphibian, and an invertebrate.

44. The method of claim 36, wherein the device is selected from the group consisting of a container with a dropper/closure device, a squeeze bottle pump spray, an airless and preservative-free spray, and a nasal insert.

* * * * *

SEQUENCE LISTING

```
Sequence total quantity: 40
SEQ ID NO: 1           moltype = DNA  length = 20
FEATURE                Location/Qualifiers
misc_feature           1..20
                       note = Synthetic: Cpf1-39-56-sp1
source                 1..20
                       mol_type = other DNA
```

```
                       organism = synthetic construct
SEQUENCE: 1
gttgcattaa tcagcatcag                                          20

SEQ ID NO: 2           moltype = DNA  length = 20
FEATURE                Location/Qualifiers
misc_feature           1..20
                       note = Synthetic: Cpf1-39-56-sp2
source                 1..20
                       mol_type = other DNA
                       organism = synthetic construct
SEQUENCE: 2
cgcccttgaa gttccttctg                                          20

SEQ ID NO: 3           moltype = DNA  length = 20
FEATURE                Location/Qualifiers
misc_feature           1..20
                       note = Synthetic: Cpf1-FarP7K-sp1
source                 1..20
                       mol_type = other DNA
                       organism = synthetic construct
SEQUENCE: 3
tccactccaa gatgctccat                                          20

SEQ ID NO: 4           moltype = DNA  length = 20
FEATURE                Location/Qualifiers
misc_feature           1..20
                       note = Synthetic: Cpf1-FarP7K-sp2
source                 1..20
                       mol_type = other DNA
                       organism = synthetic construct
SEQUENCE: 4
aaaccgttca agagtttttg                                          20

SEQ ID NO: 5           moltype = DNA  length = 20
FEATURE                Location/Qualifiers
misc_feature           1..20
                       note = Synthetic: Cpf1-FarP7K-sp3
source                 1..20
                       mol_type = other DNA
                       organism = synthetic construct
SEQUENCE: 5
aatttagcac tcgtggagat                                          20

SEQ ID NO: 6           moltype = DNA  length = 20
FEATURE                Location/Qualifiers
misc_feature           1..20
                       note = Synthetic: Cpf1-FarP7K-sp4
source                 1..20
                       mol_type = other DNA
                       organism = synthetic construct
SEQUENCE: 6
tcgcccgaat gaatccagtt                                          20

SEQ ID NO: 7           moltype = DNA  length = 20
FEATURE                Location/Qualifiers
misc_feature           1..20
                       note = Synthetic: Cpf1-FarP7K-sp5
source                 1..20
                       mol_type = other DNA
                       organism = synthetic construct
SEQUENCE: 7
ggaagaatcc gttaatcgtc                                          20

SEQ ID NO: 8           moltype = DNA  length = 20
FEATURE                Location/Qualifiers
misc_feature           1..20
                       note = Synthetic: Cpf1-FarP7K-sp6
source                 1..20
                       mol_type = other DNA
                       organism = synthetic construct
SEQUENCE: 8
ccagtgagtt ttcacacgaa                                          20

SEQ ID NO: 9           moltype = DNA  length = 20
FEATURE                Location/Qualifiers
misc_feature           1..20
                       note = Synthetic: Cpf1-FarP18K-sp1
source                 1..20
```

```
                      mol_type = other DNA
                      organism = synthetic construct
SEQUENCE: 9
cactgatgaa gaaacggtgt                                              20

SEQ ID NO: 10         moltype = DNA  length = 20
FEATURE               Location/Qualifiers
misc_feature          1..20
                      note = Synthetic: Cpf1-FarP18K-sp2
source                1..20
                      mol_type = other DNA
                      organism = synthetic construct
SEQUENCE: 10
tctactgtaa tcatgtccca                                              20

SEQ ID NO: 11         moltype = DNA  length = 20
FEATURE               Location/Qualifiers
misc_feature          1..20
                      note = Synthetic: Cpf1-FarP18K-sp3
source                1..20
                      mol_type = other DNA
                      organism = synthetic construct
SEQUENCE: 11
tcgttggttc attatacacc                                              20

SEQ ID NO: 12         moltype = DNA  length = 20
FEATURE               Location/Qualifiers
misc_feature          1..20
                      note = Synthetic: Cpf1-FarP18K-sp4
source                1..20
                      mol_type = other DNA
                      organism = synthetic construct
SEQUENCE: 12
gaattaatcg tgctgataca                                              20

SEQ ID NO: 13         moltype = DNA  length = 20
FEATURE               Location/Qualifiers
misc_feature          1..20
                      note = Synthetic: Cpf1-SegF-sp1
source                1..20
                      mol_type = other DNA
                      organism = synthetic construct
SEQUENCE: 13
ttccttctcc accctgacca                                              20

SEQ ID NO: 14         moltype = DNA  length = 20
FEATURE               Location/Qualifiers
misc_feature          1..20
                      note = Synthetic: Cpf1-SegF-sp2
source                1..20
                      mol_type = other DNA
                      organism = synthetic construct
SEQUENCE: 14
atgcagatat tagctcacgt                                              20

SEQ ID NO: 15         moltype = DNA  length = 20
FEATURE               Location/Qualifiers
misc_feature          1..20
                      note = Synthetic: Cpf1-SegF-sp3
source                1..20
                      mol_type = other DNA
                      organism = synthetic construct
SEQUENCE: 15
accatcgtat tttataatta                                              20

SEQ ID NO: 16         moltype = DNA  length = 20
FEATURE               Location/Qualifiers
misc_feature          1..20
                      note = Synthetic: Cpf1-Hoc-sp1
source                1..20
                      mol_type = other DNA
                      organism = synthetic construct
SEQUENCE: 16
cagttgatat aactcctaaa                                              20

SEQ ID NO: 17         moltype = DNA  length = 20
FEATURE               Location/Qualifiers
misc_feature          1..20
                      note = Synthetic: Cpf1-Hoc-sp2
```

```
source                  1..20
                        mol_type = other DNA
                        organism = synthetic construct
SEQUENCE: 17
atcaataacc cctgtaggtg                                             20

SEQ ID NO: 18           moltype = DNA  length = 20
FEATURE                 Location/Qualifiers
misc_feature            1..20
                        note = Synthetic: Cpf1-Hoc-sp3
source                  1..20
                        mol_type = other DNA
                        organism = synthetic construct
SEQUENCE: 18
gttatgtact aaaaggacct                                             20

SEQ ID NO: 19           moltype = DNA  length = 20
FEATURE                 Location/Qualifiers
misc_feature            1..20
                        note = Synthetic: Cpf1-Hoc-sp4
source                  1..20
                        mol_type = other DNA
                        organism = synthetic construct
SEQUENCE: 19
gaaactggta tcatctatac                                             20

SEQ ID NO: 20           moltype = DNA  length = 20
FEATURE                 Location/Qualifiers
misc_feature            1..20
                        note = Synthetic: Cpf1-Soc-sp1
source                  1..20
                        mol_type = other DNA
                        organism = synthetic construct
SEQUENCE: 20
agcagaaatt agatggaaat                                             20

SEQ ID NO: 21           moltype = DNA  length = 20
FEATURE                 Location/Qualifiers
misc_feature            1..20
                        note = Synthetic: Cpf1-Soc-sp2
source                  1..20
                        mol_type = other DNA
                        organism = synthetic construct
SEQUENCE: 21
atattaacat aaccgcgagt                                             20

SEQ ID NO: 22           moltype = DNA  length = 20
FEATURE                 Location/Qualifiers
misc_feature            1..20
                        note = Synthetic: Cpf1-Soc-sp3
source                  1..20
                        mol_type = other DNA
                        organism = synthetic construct
SEQUENCE: 22
cagcaatcca ttcagtacgt                                             20

SEQ ID NO: 23           moltype = DNA  length = 20
FEATURE                 Location/Qualifiers
misc_feature            1..20
                        note = Synthetic: Cpf1-Soc-sp4
source                  1..20
                        mol_type = other DNA
                        organism = synthetic construct
SEQUENCE: 23
tggaaagtaa ctggttaata                                             20

SEQ ID NO: 24           moltype = DNA  length = 20
FEATURE                 Location/Qualifiers
misc_feature            1..20
                        note = Synthetic: Cpf1-Mrh2-sp1
source                  1..20
                        mol_type = other DNA
                        organism = synthetic construct
SEQUENCE: 24
ttcattacat gtcgtgaaat                                             20

SEQ ID NO: 25           moltype = DNA  length = 20
FEATURE                 Location/Qualifiers
misc_feature            1..20
```

```
                         note = Synthetic: Cpf1-Mrh2-sp2
source                   1..20
                         mol_type = other DNA
                         organism = synthetic construct
SEQUENCE: 25
gatattatca tttcacgaca                                              20

SEQ ID NO: 26            moltype = DNA  length = 20
FEATURE                  Location/Qualifiers
misc_feature             1..20
                         note = Synthetic: Cpf1-Mrh2-sp3
source                   1..20
                         mol_type = other DNA
                         organism = synthetic construct
SEQUENCE: 26
aattcgactt gcttctcacc                                              20

SEQ ID NO: 27            moltype = DNA  length = 20
FEATURE                  Location/Qualifiers
misc_feature             1..20
                         note = Synthetic: Cpf1-IPIII-sp1
source                   1..20
                         mol_type = other DNA
                         organism = synthetic construct
SEQUENCE: 27
aagtcggaag cctttgtagc                                              20

SEQ ID NO: 28            moltype = DNA  length = 20
FEATURE                  Location/Qualifiers
misc_feature             1..20
                         note = Synthetic: Cpf1-IPIII-sp2
source                   1..20
                         mol_type = other DNA
                         organism = synthetic construct
SEQUENCE: 28
tgcttggcaa attcaagacc                                              20

SEQ ID NO: 29            moltype = DNA  length = 20
FEATURE                  Location/Qualifiers
misc_feature             1..20
                         note = Synthetic: Cpf1-IPIII-sp3
source                   1..20
                         mol_type = other DNA
                         organism = synthetic construct
SEQUENCE: 29
ctgatcggta ggtccactca                                              20

SEQ ID NO: 30            moltype = DNA  length = 20
FEATURE                  Location/Qualifiers
misc_feature             1..20
                         note = Synthetic: Cpf1-IPIII-sp4
source                   1..20
                         mol_type = other DNA
                         organism = synthetic construct
SEQUENCE: 30
ctacagaagc ttcggcaata                                              20

SEQ ID NO: 31            moltype = DNA  length = 20
FEATURE                  Location/Qualifiers
misc_feature             1..20
                         note = Synthetic: Cpf1-IPII-sp1
source                   1..20
                         mol_type = other DNA
                         organism = synthetic construct
SEQUENCE: 31
cttctaagtt cggcatgtct                                              20

SEQ ID NO: 32            moltype = DNA  length = 20
FEATURE                  Location/Qualifiers
misc_feature             1..20
                         note = Synthetic: Cpf1-IPII-sp2
source                   1..20
                         mol_type = other DNA
                         organism = synthetic construct
SEQUENCE: 32
ttacggtctt tatcgggcaa                                              20

SEQ ID NO: 33            moltype = DNA  length = 20
FEATURE                  Location/Qualifiers
```

```
misc_feature            1..20
                        note = Synthetic: Cas9-IPIII-sp1
source                  1..20
                        mol_type = other DNA
                        organism = synthetic construct
SEQUENCE: 33
atggaaaggt cttgatgcaa                                              20

SEQ ID NO: 34           moltype = DNA  length = 20
FEATURE                 Location/Qualifiers
misc_feature            1..20
                        note = Synthetic: Cas9-IPIII-sp2
source                  1..20
                        mol_type = other DNA
                        organism = synthetic construct
SEQUENCE: 34
attatcaatg acccatttac                                              20

SEQ ID NO: 35           moltype = DNA  length = 20
FEATURE                 Location/Qualifiers
misc_feature            1..20
                        note = Synthetic: Cas9-IPIII-sp3
source                  1..20
                        mol_type = other DNA
                        organism = synthetic construct
SEQUENCE: 35
ggcctttact acagaagctt                                              20

SEQ ID NO: 36           moltype = AA  length = 12
FEATURE                 Location/Qualifiers
REGION                  1..12
                        note = Synthetic: E12
source                  1..12
                        mol_type = protein
                        organism = synthetic construct
SEQUENCE: 36
MYSFVSEETG TL                                                      12

SEQ ID NO: 37           moltype = AA  length = 419
FEATURE                 Location/Qualifiers
REGION                  1..419
                        note = MISC_FEATURE - SARS-CoV-2 nucleoprotein
source                  1..419
                        mol_type = protein
                        organism = Severe acute respiratory syndrome-related
                         coronavirus 2
SEQUENCE: 37
MSDNGPQNQR NAPRITFGGP SDSTGSNQNG ERSGARSKQR RPQGLPNNTA SWFTALTQHG  60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTAAIKLD DKDPNFKDQV ILLNKHIDAY  360
KTFPPTEPKK DKKKKADETQ ALPQRQKKQQ TVTLLPAADL DDFSKQLQQS MSSADSTQA   419

SEQ ID NO: 38           moltype = AA  length = 1207
FEATURE                 Location/Qualifiers
REGION                  1..1207
                        note = MISC_FEATURE - SARS-CoV-2 prefusion-stabilized spike
                         ecto-domain
source                  1..1207
                        mol_type = protein
                        organism = Severe acute respiratory syndrome-related
                         coronavirus 2
SEQUENCE: 38
FVFLVLLPLV SSQCVNLTTR TQLPPAYTNS FTRGVYYPDK VFRSSVLHST QDLFLPFFSN  60
VTWFHAIHVS GTNGTKRFDN PVLPFNDGVY FASTEKSNII RGWIFGTTLD SKTQSLLIVN  120
NATNVVIKVC EFQFCNDPFL GVYYHKNNKS WMESEFRVYS SANNCTFEYV SQPFLMDLEG  180
KQGNFKNLRE FVFKNIDGYF KIYSKHTPIN LVRDLPQGFS ALEPLVDLPI GINITRFQTL  240
LALHRSYLTP GDSSSGWTAG AAAYYVGYLQ PRTFLLKYNE NGTITDAVDC ALDPLSETKC  300
TLKSFTVEKG IYQTSNFRVQ PTESIVRFPN ITNLCPFGEV FNATRFASVY AWNRKRISNC  360
VADYSVLYNS ASFSTFKCYG VSPTKLNDLC FTNVYADSFV IRGDEVRQIA PGQTGKIADY  420
NYKLPDDFTG CVIAWNSNNL DSKVGGNYNY LYRLFRKSNL KPFERDISTE IYQAGSTPCN  480
GVEGFNCYFP LQSYGFQPTN GVGYQPYRVV VLSFELLHAP ATVCGPKKST NLVKNKCVNF  540
NFNGLTGTGV LTESNKKFLP FQQFGRDIAD TTDAVRDPQT LEILDITPCS FGGVSVITPG  600
TNTSNQVAVL YQDVNCTEVP VAIHADQLTP TWRVYSTGSN VFQTRAGCLI GAEHVNNSYE  660
CDIPIGAGIC ASYQTQTNSP GSASSVASQS IIAYTMSLGA ENSVAYSNNS IAIPTNFTIS  720
VTTEILPVSM TKTSVDCTMY ICGDSTECSN LLLQYGSFCT QLNRALTGIA VEQDKNTQEV  780
FAQVKQIYKT PPIKDFGGFN FSQILPDPSK PSKRSFIEDL LFNKVTLADA GFIKQYGDCL  840
```

-continued

```
GDIAARDLIC AQKFNGLTVL PPLLTDEMIA QYTSALLAGT ITSGWTFGAG AALQIPFAMQ  900
MAYRFNGIGV TQNVLYENQK LIANQFNSAI GKIQDSLSST ASALGKLQDV VNQNAQALNT  960
LVKQLSSNFG AISSVLNDIL SRLDPPEAEV QIDRLITGRL QSLQTYVTQQ LIRAAEIRAS  1020
ANLAATKMSE CVLGQSKRVD FCGKGYHLMS FPQSAPHGVV FLHVTYVPAQ EKNFTTAPAI  1080
CHDGKAHFPR EGVFVSNGTH WFVTQRNFYE PQIITTDNTF VSGNCDVVIG IVNNTVYDPL  1140
QPELDSFKEE LDKYFKNHTS PDVDLGDISG INASVVNIQK EIDRLNEVAK NLNESLIDLQ  1200
ELGKYEQ                                                            1207

SEQ ID NO: 39          moltype = AA  length = 80
FEATURE                Location/Qualifiers
REGION                 1..80
                       note = Synthetic: T4 Soc
source                 1..80
                       mol_type = protein
                       organism = synthetic construct
SEQUENCE: 39
MASTRGYVNI KTFEQKLDGN KKIEGKEISV AFPLYSDVHK ISGAHYQTFP SEKAAYSTVY  60
EENQRTEWIA ANEDLWKVTG                                              80

SEQ ID NO: 40          moltype = AA  length = 376
FEATURE                Location/Qualifiers
REGION                 1..376
                       note = Synthetic: T4 Hoc
source                 1..376
                       mol_type = protein
                       organism = synthetic construct
SEQUENCE: 40
MTFTVDITPK TPTGVIDETK QFTATPSGQT GGGTITYAWS VDNVPQDGAE ATFSYVLKGP  60
AGQKTIKVVA TNTLSEGGPE TAEATTTITV KNKTQTTTLA VTPASPAAGV IGTPVQFTAA  120
LASQPDGASA TYQWYVDDSQ VGGETNSTFS YTPTTSGVKR IKCVAQVTAT DYDALSVTSN  180
EVSLTVNKKT MNPQVTLTPP SINVQQDASA TFTANVTGAP EEAQITYSWK KDSSPVEGST  240
NVYTVDTSSV GSQTIEVTAT VTAADYNPVT VTKTGNVTVT AKVAPEPEGE LPYVHPLPHR  300
SSAYIWCGWW VMDEIQKMTE EGKDWKTDDP DSKYYLHRYT LQKMMKDYPE VDVQESRNGY  360
IIHKTALETG IIYTYP                                                  376
```